US012734218B2

(12) United States Patent
Lee et al.

(10) Patent No.: US 12,734,218 B2

(45) **Date of Patent: *Sep. 15, 2026**

(54) USE OF TRIGONAL AGONIST HAVING ACTIVITIES TO ALL OF GLUCAGON, GLP-1, AND GIP RECEPTORS IN TREATMENT OF SEQUELAE FOLLOWING RESPIRATORY INFECTIOUS DISEASES

(71) Applicant: HANMI PHARM. CO., LTD., Hwaseong-si (KR)

(72) Inventors: Jong Suk Lee, Hwaseong-si (KR); Jung Kuk Kim, Hwaseong-si (KR); Seon Myeong Lee, Hwaseong-si (KR); Sang Hyun Lee, Hwaseong-si (KR); Jeong A Kim, Hwaseong-si (KR); Euh Lim Oh, Hwaseong-si (KR); Chong Yoon Lim, Hwaseong-si (KR)

(73) Assignee: HANMI PHARM. CO., LTD., Hwaseong-si (KR)

(*) Notice: Subject to any disclaimer, the term of this patent is extended or adjusted under 35 U.S.C. 154(b) by 680 days.

This patent is subject to a terminal disclaimer.

(21) Appl. No.: 18/031,958

(22) PCT Filed: Oct. 18, 2021

(86) PCT No.: PCT/KR2021/014485

§ 371 (c)(1),
(2) Date: Apr. 14, 2023

(87) PCT Pub. No.: WO2022/080991

PCT Pub. Date: Apr. 21, 2022

(65) Prior Publication Data

US 2023/0390362 A1 Dec. 7, 2023

(30) Foreign Application Priority Data

Oct. 16, 2020 (KR) ........................ 10-2020-0134344
Mar. 3, 2021 (KR) ........................ 10-2021-0028215

(51) Int. Cl.

| | |
|---|---|
| ***A61K 38/00*** | (2006.01) |
| ***A61K 38/26*** | (2006.01) |
| ***A61K 47/68*** | (2017.01) |
| ***A61P 11/00*** | (2006.01) |

(52) U.S. Cl.

CPC .......... *A61K 38/26* (2013.01); *A61K 47/6811* (2017.08); *A61P 11/00* (2018.01)

(58) Field of Classification Search

CPC .... A61K 38/26; A61K 47/6811; A61K 38/16; A61K 47/68; A61K 38/1796; A61P 11/00; A61P 25/00; A61P 29/00; A61P 31/12; A61P 31/14; Y02A 50/30; C07K 14/605

See application file for complete search history.

(56) References Cited

U.S. PATENT DOCUMENTS

| | | | | |
|---|---|---|---|---|
| 10,370,426 | B2 * | 8/2019 | Oh | C07K 14/47 |
| 10,400,020 | B2 | 9/2019 | Oh et al. | |
| 2015/0322129 | A1 | 11/2015 | Bossart et al. | |
| 2017/0298117 | A1 * | 10/2017 | Hwang | A61P 1/16 |

FOREIGN PATENT DOCUMENTS

| | | | |
|---|---|---|---|
| KR | 10-2017-0080522 | A | 7/2017 |
| KR | 10-2020-0038878 | A | 4/2020 |
| WO | 2017/116204 | A1 | 7/2017 |
| WO | 2017/116205 | A1 | 7/2017 |
| WO | 2021/145552 | A1 | 7/2021 |

OTHER PUBLICATIONS

Ahmad et al. (Biochim Biophys Acta Mol Basis Dis. Jun. 13, 2020; 1866(10):165878).*
Bloodworth et al. Letter to the Editor, vol. 142, Issue 2p. 683-687).*
Deependra Kumar Rai, et al., Post covid 19 pulmonary fibrosis. Is it real threat?, Elsevier, Indian Journal of Tuberculosis, 2021, pp. 330-333, vol. 68.
Hye Soon Kim, "Management of Diabetes in Coronavirus Disease 2019: Prognosis and Practical Issues", The Journal of Korean Diabetes, Sep. 2020, pp. 120-125, vol. 21, No. 3.
Ying Jie Chee, et al., "Dissecting the interaction between COVID-19 and diabetes mellitus", JDI Journal of Diabetes Investigation, Official Journal of the Asian Association for the Study of Diabetes, Sep. 5, 2020, pp. 1104-1114, vol. 11, No. 5.
International Search Report for PCT/KR2021/014485 dated Feb. 14, 2022.
Extended European Search Report issued Sep. 24, 2024 in Application No. 21880637.0.
Makarev, et al., "Common pathway signature in lung and liver fibrosis", Cell Cycle, 2016, vol. 15, No. 13, pp. 1667-1673 (7 pages).
Liu, et al., "Application of nintedanib and other potential anti-fibrotic agents in fibrotic diseases", Clin Sci (Lond), Jun. 28, 2019, vol. 133, No. 12, pp. 1309-1320 (20 pages).
im, et al., "Therapeutic effect of a novel long-acting GLP-1/GIP/Glucagon triple agonist (HM15211) in a NASH and fibrosis animal model", American Diabetes Association (ADA) 79$^{th}$ Scientific Sessions, San Francisco, CA, USA, Jun. 7-11, 2019, Retrieved from the internet: URL:https//www.hanmipharm.com/ehanmi/rnd/HM15211/13.2019_ADA_Poster_HM15211.pdf [retrieved on Nov. 21, 2022] 1 page total.
Kim, et al., "Therapeutic effect of a novel long-acting GLP-1/GIP/Glucagon triple agonist (HM15211) in NASH and fibrosis animal models", Diabetologia, 2018, vol. 61, Suppl. 1, pp. S61-S62 (2 pages).
Bai et al., "The active GLP-1 analogue liraglutide alleviates H9N2 influenza virus-induced acute lung injury in mice", Microbial Pathogenesis, 2021, vol. 150, No. 104645, pp. 1-12 (13 pages total).

(Continued)

*Primary Examiner* — Jeanette M Lieb

(74) *Attorney, Agent, or Firm* — Sughrue Mion, PLLC

(57) ABSTRACT

Provided is use of a trigonal agonist having activities to all of glucagon, GLP-1, and GIP receptors, and/or a conjugate thereof in the prevention or treatment of sequelae following respiratory infectious diseases.

16 Claims, 2 Drawing Sheets

Specification includes a Sequence Listing.

(56) References Cited

OTHER PUBLICATIONS

Fandiño et al., "GLP-1 receptor agonist ameliorates experimental lung fibrosis", Scientific Reports, 2020, vol. 10, No. 18091, pp. 1-15 (16 pages total).

* cited by examiner

[FIG. 1A]
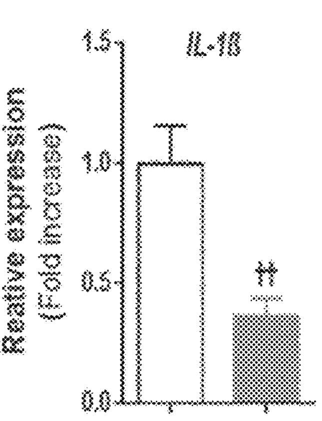
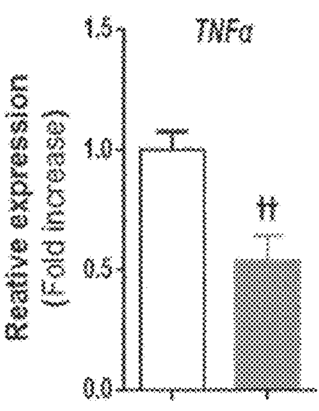
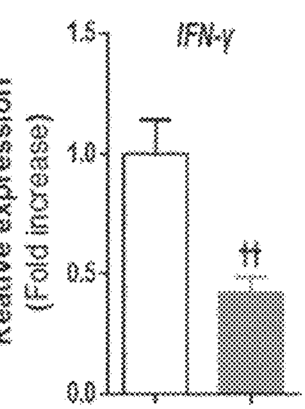
[FIG. 1B]
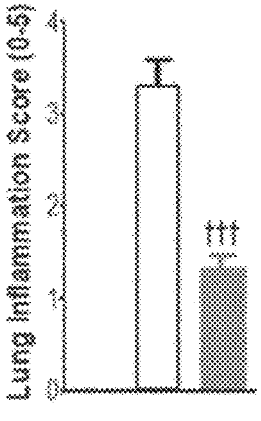
■ Non-infected, excipient control group
□ SARS-Cov-2-infected, excipient control group
▩ SARS-Cov-2-infected, long-acting conjugate of SEQ ID NO: 42 125 μg/kg, Q2D

[FIG. 2]
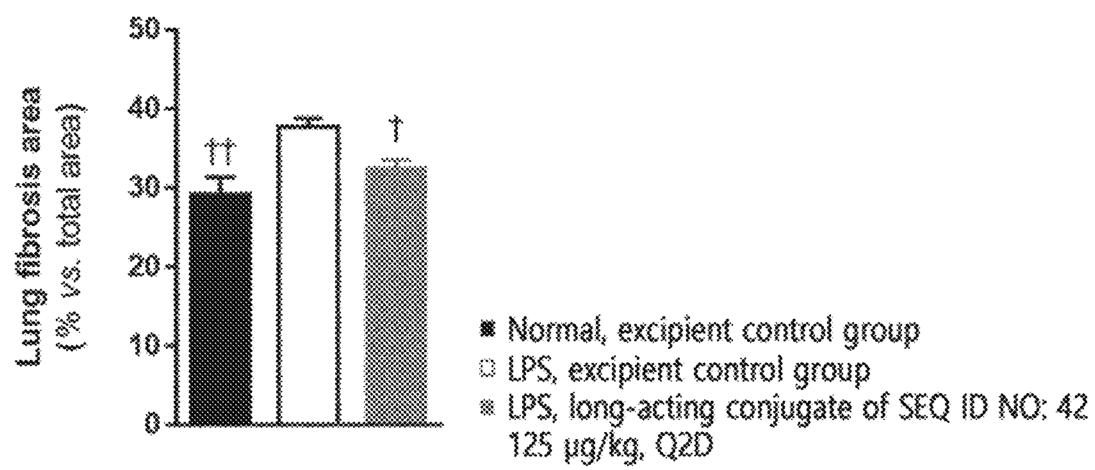

USE OF TRIGONAL AGONIST HAVING ACTIVITIES TO ALL OF GLUCAGON, GLP-1, AND GIP RECEPTORS IN TREATMENT OF SEQUELAE FOLLOWING RESPIRATORY INFECTIOUS DISEASES

CROSS REFERENCE TO RELATED APPLICATIONS

This application is a National Stage of International Application No. PCT/KR2021/014485 filed Oct. 18, 2021, claiming priority based on Korean Patent Application No. 10-2020-0134344 filed Oct. 16, 2020 and Korean Patent Application No. 10-2021-0028215 filed Mar. 3, 2021.

INCORPORATION BY REFERENCE OF SEQUENCE LISTING

The content of the electronically submitted sequence listing, file name: Q286704_Sequence_Listing_As_Filed.txt; size: 71,751 bytes; and date of creation: Apr. 6, 2023, filed herewith, is incorporated herein by reference in its entirety.

TECHNICAL FIELD

The present invention relates to use of a trigonal agonist having activities to all of glucagon, GLP-1, GIP receptors, and/or a conjugate thereof in the prevention or treatment of sequelae following respiratory infectious diseases.

BACKGROUND ART

Respiratory infectious diseases are respiratory diseases caused by infection with pathogens (viruses, bacteria, mycoplasma, fungi, etc.). Representative respiratory infectious diseases include respiratory viral infectious diseases caused by pathogenic viral infection. Respiratory infectious diseases may cause mild upper respiratory tract infections and severe lower respiratory tract infections accompanied by pneumonia and bronchitis, and may be fatal to people with impaired cardiopulmonary function.

Among respiratory viruses, a novel coronavirus (2019-nCoV or SARS-CoV-2) that causes coronavirus disease-19 (COVID-19) is highly contagious, and several variants of SARS-CoV-2 viruses with high infectiousness have also emerged, resulting in a worldwide pandemic. Since the novel coronavirus that spreads through the respiratory tract penetrates into cells through ACE2 and TMPRSS2, which are mainly expressed in type II alveolar epithelial cells, the lung is known as a major vulnerable organ. The main symptoms include fever, cough, etc., and healthy adults are more likely to recover over time. However, in some patients, an extreme immune response such as a cytokine release syndrome causes lung damage and promotes progression of pulmonary fibrosis, which may be accompanied by symptoms such as acute respiratory distress syndrome (ARDS), sepsis, etc.

In patients with respiratory infectious diseases such as novel coronavirus, sequelae remain even after complete recovery and often cause difficulties in daily life, and these sequelae may be often caused by a cytokine storm, resulting in lung damage.

With regard to SARS-CoV-2 virus, which has caused a worldwide pandemic, it has been reported that hyperimmune responses occur after infection, causing severe pneumonia and acute respiratory distress, and also leaving sequelae after complete recovery.

A representative mechanism of the hyperimmune responses is known to be the excessive secretion of pro-inflammatory cytokines by an inflammasome complex, which is a cytoplasmic multiprotein oligomer responsible for the activation of inflammatory responses due to infection with SARS-CoV-2 virus, and activated macrophages causing tissue damage while strongly exhibiting the properties of inflammatory macrophages. In addition, other major organs besides the lungs may be damaged by hyperimmune inflammatory responses caused by a cytokine storm.

Due to the hyperimmune inflammatory responses, various sequelae remain even after complete recovery from infection with the respiratory virus, and thus appropriate treatment and management are important even after treatment of respiratory infectious diseases. For example, in the case of patients with coronavirus disease-19, even after recovering, they show various sequelae such as dyspnea, coughing, stuffy chest, extreme fatigue, heart disease, loss of lung function, kidney damage, etc. In particular, it is known that as the risk of coronavirus disease-19 becomes higher or the symptoms more severe, the risk of sequelae increases (Deependra Kumar Rai et al., *Indian J Tuberc.* 2020 Nov. 10).

Post-COVID-19 pulmonary fibrosis, which is one of the sequelae experienced by the patients with coronavirus disease-19, is known to be mainly caused by lung damage due to viral infection. One of the major causes of the lung damage has been pointed out as an excessive immune response (cytokine storm) caused by viral infection.

Pulmonary fibrosis, which appears as sequelae following coronavirus disease-19, has a much faster onset and progression of symptoms than commonly observed in pulmonary fibrosis. Therefore, unlike the existing therapeutic agents for pulmonary fibrosis, which focus on relief of symptoms and delay of progression from a long-term perspective, a therapeutic approach is required that is capable of simultaneously targeting pulmonary inflammation, which is a cause of pulmonary fibrosis, and fibrosis. However, effective therapeutic agents have not yet been identified. For example, the possibility of treatment with pirfenidone or nintedanib, known as anti-fibrotic agents, has been suggested, but their efficacy is limited because they do not show relatively large effects on lung inflammation itself. In addition, since most patients with coronavirus disease-19 show liver dysfunction, and the anti-fibrotic agents, broadly classified as pirfenidone or nintedanib, are highly likely to cause hepatotoxicity, it is difficult to prescribe the commonly known anti-fibrotic agents to patients suffering from sequelae following coronavirus disease-19 (Deependra Kumar Rai et al., *Indian J Tuberc.* 2020 Nov. 10).

Ultimately, even though various therapeutic agents are being developed to treat infectious diseases caused by respiratory viruses, development of therapeutic agents to prevent or treat sequelae following respiratory infectious diseases, which are able to minimize lung damage such as pulmonary fibrosis by suppressing the inflammatory responses, is still unsatisfactory.

On the other hand, glucagon-like peptide-1 (GLP-1) and glucose-dependent insuliontropic polypeptide (GIP) are representative gastrointestinal hormones and neuronal hormones, and are materials involved in the control of blood glucose levels according to food intake. Glucagon is a peptide hormone secreted by the pancreas and is involved in controlling the blood glucose levels along with the two materials described above. Treatments are being developed using drugs that are able to act on each or all of GLP-1 receptor, GIP receptor, and glucagon receptor (U.S. Pat. Nos. 10,370,426, 10,400,020).

Until now, various studies have been conducted on sequelae following respiratory infectious diseases, but the development of practical and effective therapeutic agents is still insufficient. Accordingly, there is a need for continuous development of therapeutic agents.

DISCLOSURE

Technical Problem

It is required to develop a therapeutic agent for preventing or treating sequelae of respiratory infectious diseases.

Technical Solution

An object of the present invention is to provide a pharmaceutical composition for preventing or treating sequelae following respiratory infectious diseases, the pharmaceutical composition including a peptide having activities to a glucagon receptor, a GLP-1 receptor, and a GIP receptor, or a long-acting conjugate of the peptide.

Another object of the present invention is to provide a method of preventing or treating sequelae following respiratory infectious diseases, the method including the step of administering the composition including the peptide or the long-acting conjugate of the peptide to an individual in need thereof.

Still another object of the present invention is to provide use of the composition including the peptide or the long-acting conjugate of the peptide in the preparation of a prophylactic or therapeutic agent for sequelae following respiratory infectious diseases.

Still another object of the present invention is to provide use of the composition including the peptide or the long-acting conjugate of the peptide in the prevention or treatment of sequelae following respiratory infectious diseases.

Advantageous Effects

A trigonal agonist according to the present invention or a long-acting conjugate thereof may have activities to a glucagon receptor, a glucagon-like peptide-1 (GLP-1) receptor, and a glucose-dependent insulinotropic polypeptide (GIP) receptor, thereby exhibiting effects of preventing or treating sequelae following respiratory infectious diseases.

DESCRIPTION OF DRAWINGS

FIG. 1A shows reduced pulmonary cytokine expression in SARS-CoV-2-infected hamsters according to administration of a long-acting conjugate of SEQ ID NO: 42, and FIG. 1B shows changes in the lung inflammation score; and FIG. 2 showed changes in the pulmonary fibrotic area of cytokine storm-induced hamsters according to administration of the long-acting conjugate of SEQ ID NO: 42.

BEST MODE

One embodiment to achieve the present invention provides a pharmaceutical composition for preventing or treating sequelae following respiratory infectious diseases, the pharmaceutical composition including a peptide having activities to a glucagon receptor, a glucagon-like peptide-1 (GLP-1) receptor, and a glucose-dependent insulinotropic polypeptide (GIP) receptor.

In one specific embodiment, the pharmaceutical composition for preventing or treating sequelae following respiratory infectious diseases is characterized by including a pharmaceutically acceptable excipient and a pharmaceutically effective amount of a peptide including any one amino acid sequence of SEQ ID NOS: 1 to 102.

The pharmaceutical composition according to any one of the specific embodiments is characterized in that the peptide is in the form of a long-acting conjugate, wherein the long-acting conjugate is represented by the following Chemical Formula 1:

X-L-F [Chemical Formula 1]

wherein X is a peptide including any one amino acid sequence of SEQ ID NOS: 1 to 102;

L is a linker including ethylene glycol repeating units,

F is an immunoglobulin Fc region, and

- represents a covalent linkage between X and L, and between L and F.

The composition according to any one of the specific embodiments is characterized in that the respiratory infectious disease is a respiratory viral infectious disease.

The composition according to any one of the specific embodiments is characterized in that the respiratory viral infectious disease is an infectious disease caused by any one respiratory virus selected from the group consisting of adenovirus, vaccinia virus, herpes simplex virus, parainfluenza virus, rhinovirus, varicella zoster virus, measle virus, respiratory syncytial virus, Dengue virus, human immunodeficiency virus (HIV), influenza virus, coronavirus, severe acute respiratory syndrome associated virus (SARS-associated virus), and Middle East respiratory syndrome coronavirus (MERS-CoV).

The composition according to any one of the specific embodiments is characterized in that the coronavirus is SARS-CoV-2.

The composition according to any one of the specific embodiments is characterized in that the respiratory virus is a variant virus.

The composition according to any one of the specific embodiments is characterized in that the variant respiratory virus causes sequelae the same as those caused by the respiratory virus.

The composition according to any one of the specific embodiments is characterized in that the variant respiratory virus is any one selected from the group consisting of SARS-CoV-2 alpha variant (B.1.1.7 lineage), SARS-CoV-2 beta variant (B.1.351 lineage), SARS-CoV-2 gamma variant (P.1 lineage), and SARS-CoV-2 delta variant (B.1.617.2 lineage).

The composition according to any one of the specific embodiments is characterized in that the sequelae following respiratory infectious diseases are any one or more selected from the group consisting of fever, dyspnea, cough, pneumonia, pulmonary fibrosis, pain, myalgia, fatigue, inflammation, and nervous system disorders.

The composition according to any one of the specific embodiments is characterized in that the sequelae following respiratory infectious diseases are caused by tissue damage due to excessive cytokine secretion.

The composition according to any one of the specific embodiments is characterized in that the sequelae following respiratory infectious diseases are post-COVID-19 pulmonary fibrosis.

The composition according to any one of the specific embodiments is characterized in that the pharmaceutical composition has one or more of the following characteristics when administered:

(i) a reduction in the lung inflammation score;

(ii) a reduction in the expression or secretion of pro-inflammatory cytokines;

(iii) a reduction in the pulmonary fibrotic area; and (iv) suppressed production of inflammasome complexes.

The composition according to any one of the specific embodiments is characterized in that the cytokine is any one or more selected from the group consisting of interleukin, tumor necrosis factor, and interferon.

The composition according to any one of the specific embodiments is characterized in that the cytokine is IL-1β, TNF-α, or IFN-γ.

The composition according to any one of the specific embodiments is characterized in that the pharmaceutical composition is administered to an individual having cytokine storm syndrome, sepsis, or organ failure due to respiratory viral infection.

The composition according to any one of the specific embodiments is characterized in that the peptide is amidated at the C-terminus thereof.

The composition according to any one of the specific embodiments is characterized in that the peptide is amidated or has a free carboxylic group (—COOH) at the C-terminus thereof.

The composition according to any one of the specific embodiments is characterized in that the peptide includes an amino acid sequence selected from the group consisting of SEQ ID NOS: 21, 22, 42, 43, 50, 77, and 96.

The composition according to any one of the specific embodiments is characterized in that the peptide has a ring formed between amino acid residues.

The composition according to any one of the specific embodiments is characterized in that the peptide sequence has a ring formed between an amino acid at position 16 and an amino acid at position 20 from the N-terminus.

The composition according to any one of the specific embodiments is characterized in that the immunoglobulin Fc region is aglycosylated.

The composition according to any one of the specific embodiments is characterized in that the immunoglobulin Fc region is selected from the group consisting of (a) CH1 domain, CH2 domain, CH3 domain, and CH4 domain; (b) CH1 domain and CH2 domain; (c) CH1 domain and CH3 domain; (d) CH2 domain and CH3 domain; (e) a combination of one domain or two or more domains of CH1 domain, CH2 domain, CH3 domain, and CH4 domain and an immunoglobulin hinge region or a portion of the hinge region; and (f) a dimer of each domain of a heavy chain constant region and a light chain constant region.

The composition according to any one of the specific embodiments is characterized in that the immunoglobulin Fc region has a deletion of a region capable of forming a disulfide bond, a deletion of several amino acids at the N-terminus of a native Fc form, an addition of a methionine residue to the N-terminus of the native Fc form, a deletion of a complement-binding site, or a deletion of antibody-dependent cell-mediated cytotoxicity (ADCC) site.

The composition according to any one of the specific embodiments is characterized in that the immunoglobulin Fc region is derived from IgG, IgA, IgD, IgE, or IgM.

The composition according to any one of the specific embodiments is characterized in that the F is an IgG Fc region.

The composition according to any one of the specific embodiments is characterized in that the immunoglobulin Fc region is an IgG4 Fc region.

The composition according to any one of the specific embodiments is characterized in that the immunoglobulin Fc region is a human IgG4-derived aglycosylated Fc region.

The composition according to any one of the specific embodiments is characterized in that the immunoglobulin Fc region has a structure in which two polypeptide chains are linked via disulfide bonds, wherein they are linked via only a nitrogen atom of one chain of the two chains.

The composition according to any one of the specific embodiments is characterized in that the immunoglobulin Fc region has a dimeric form.

The composition according to any one of the specific embodiments is characterized in that the immunoglobulin Fc region includes a monomer having an amino acid sequence of SEQ ID NO: 123.

The composition according to any one of the specific embodiments is characterized in that the immunoglobulin Fc region is a homodimer of the monomer having the amino acid sequence of SEQ ID NO: 123.

The composition according to any one of the specific embodiments is characterized in that the immunoglobulin Fc region is linked via a nitrogen atom of proline at the N-terminus thereof.

The composition according to any one of the specific embodiments is characterized in that the immunoglobulin Fc region, F and X are not glycosylated. The composition according to any one of the specific embodiments is characterized in that the immunoglobulin Fc region is a domain hybrid of a different origin derived from an immunoglobulin selected from the group consisting of IgG, IgA, IgD, IgE, and IgM.

The composition according to any one of the specific embodiments is characterized in that the region F is a dimer consisting of two polypeptide chains, and one end of L is linked to only one polypeptide chain of the two polypeptide chains.

The composition according to any one of the specific embodiments is characterized in that, in the conjugate, F and X are linked to each other via covalent bonds formed by reacting one end of L with an amine group or a thiol group of F and by reacting the other end of L with an amine group or a thiol group of X, respectively.

The composition according to any one of the specific embodiments is characterized in that L is polyethylene glycol.

The composition according to any one of the specific embodiments is characterized in that the ethylene glycol repeating unit is represented by $[OCH_2CH_2]_n$, wherein n is a natural number, which is determined such that an average molecular weight, e.g., a number average molecular weight of $[OCH_2CH_2]_n$ in the peptide conjugate is 1 kDa to 100 kDa.

The composition according to any one of the specific embodiments is characterized in that the value of n is determined such that an average molecular weight, e.g., a number average molecular weight of $[OCH_2CH_2]_n$ in the peptide conjugate is 10 kDa.

The composition according to any one of the specific embodiments is characterized in that a formula weight of the ethylene glycol repeating unit in L is in the range of 1 kDa to 100 kDa.

The composition according to any one of the specific embodiments is characterized in that the peptide includes an amino acid sequence selected from the group consisting of SEQ ID NOS: 21, 22, 42, 43, 50, 77, and 96.

Another embodiment to achieve the present invention provides a method of preventing or treating sequelae following respiratory infectious diseases, the method including the step of administering the peptide, the long-acting conjugate thereof, or the composition including the same to an individual in need thereof.

Still another embodiment to achieve the present invention provides use of the peptide, the long-acting conjugate thereof, or the composition including the same in the preparation of a prophylactic or therapeutic agent for sequelae following respiratory infectious diseases.

Still another embodiment to achieve the present invention provides use of the peptide, the long-acting conjugate thereof, or the composition including the same in the prevention or treatment of sequelae following respiratory infectious diseases.

MODE FOR INVENTION

Hereinafter, the present disclosure will be described in more detail.

Meanwhile, each description and embodiment disclosed in this disclosure may also be applied to other descriptions and embodiments. That is, all combinations of various elements disclosed in this disclosure fall within the scope of the present disclosure. Further, the scope of the present disclosure is not limited by the specific description described below.

Throughout the entire specification, not only the common one-letter or three-letter codes for naturally occurring amino acids, but also those three-letter codes generally allowed for other amino acids are used, such as 2-aminoisobutyric acid (Aib), N-methylglycine (Sar), and α-methyl-glutamic acid, etc. Further, the amino acids mentioned in abbreviations herein are described according to the IUPAC-IUB rules as follows:

| | | | |
|---|---|---|---|
| Alanine | Ala, A | Arginine | Arg, R |
| Asparagine | Asn, N | Aspartic acid | Asp, D |
| Cysteine | Cys, C | Glutamic acid | Glu, E |
| Glutamine | Gln, Q | Glycine | Gly, G |
| Histidine | His, H | Isoleucine | Ile, I |
| Leucine | Leu, L | Lysine | Lys, K |
| Methionine | Met, M | Phenylalanine | Phe, F |
| Proline | Pro, P | Serine | Ser, S |
| Threonine | Thr, T | Tryptophan | Trp, W |
| Tyrosine | Tyr, Y | Valine | Val, V |

As used herein, "Aib" may be used interchangeably with "2-aminoisobutyric acid" or "aminoisobutyric acid", and 2-aminoisobutyric acid and aminoisobutyric acid may be used interchangeably with each other.

One embodiment to achieve the present invention provides a pharmaceutical composition for preventing or treating sequelae following respiratory infectious diseases, the pharmaceutical composition including a peptide having activities to a glucagon receptor, a glucagon-like peptide-1 (GLP-1) receptor, and a glucose-dependent insulinotropic polypeptide (GIP) receptor.

In one embodiment, the peptide may include any one amino acid sequence of SEQ ID NOS: 1 to 102.

In another embodiment, the pharmaceutical composition for preventing or treating sequelae following respiratory infectious diseases may be a pharmaceutical composition including a pharmaceutically acceptable excipient and a pharmaceutically effective amount of a peptide including any one amino acid sequence of SEQ ID NOS: 1 to 102. As used herein, the term "pharmaceutically effective amount" may refer to a safe administration dose in which the peptide or a long-acting conjugate thereof exhibits a therapeutic effect on sequelae following respiratory infectious diseases, but does not show toxicity or side effects to patients. Specifically, the pharmaceutically effective amount may refer to a dose capable of obtaining effects such as suppression of inflammatory responses and suppression of fibrosis through reduction of cytokine secretion and/or expression, but is not limited thereto.

The respiratory infectious diseases of the present invention may be respiratory diseases caused by infection with pathogens (viruses, bacteria, fungi, etc.), and a representative cause of the infection may include respiratory viruses. Among the respiratory infectious diseases, respiratory viral infectious diseases may refer to respiratory diseases caused by pathogenic viral infection. The respiratory viruses may include adenovirus, vaccinia virus, herpes simplex virus, parainfluenza virus, rhinovirus, varicella zoster virus, measle virus, respiratory syncytial virus, Dengue virus, human immunodeficiency virus (HIV), influenza virus, coronavirus, severe acute respiratory syndrome associated virus (SARS-associated virus), or Middle East respiratory syndrome coronavirus (MERS-CoV), but are not limited thereto. Further, in the present invention, the respiratory viruses may include variant viruses in which mutations occur in the genomic sequence or trait, but are not limited thereto. The variant viruses of the present invention may refer to viruses that may cause the same sequelae even having mutations, as compared with the respiratory virus.

Non-limiting examples of the coronavirus may include SARS-CoV-2, and SARS-CoV-2 infection may cause coronavirus disease-19 (coronavirus disease 2019, COVID-19). In the preset invention, the SARS-CoV-2 may include variant viruses, and specific examples of the variant viruses may include variant viruses such as alpha (B.1.1.7 lineage), beta (B.1.351 lineage), gamma (P.1 lineage), delta (B.1.617.2 lineage), etc., but are not limited thereto, as long as they are viruses having mutations that may exhibit a trait different from that of the SARS-CoV-2 virus, or may induce a trait different therefrom.

The pharmaceutical composition of the present invention may prevent, treat, or improve sequelae without limitation to the respiratory virus and variants thereof.

As used herein, the term "coronavirus disease-19" refers to a viral infectious disease caused by infection with a novel coronavirus (2019-nCoV or SARS-CoV-2). Although the source and mode of transmission have not been clearly identified yet, the transmission power is very strong, causing a worldwide pandemic.

The novel coronavirus (2019-nCoV or SARS-CoV-2) is a virus that is able to infect humans and various animals. It is an RNA virus with a gene size of 27 kb to 32 kb, and mainly presents respiratory symptoms such as cough with fever, dyspnea, shortness of breath, sputum, etc. The coronavirus is known to attack bronchial ciliated cells or alveolar epithelial type 2 cells, where receptors such as "ACE2", "TMPRSS2", etc., exist in large amounts, which help to penetrate into cells.

Like other viruses, coronavirus seizes host cell's resources and systems, proliferates vigorously, and is released out of infected cells. At this time, the exponentially proliferated viruses escape and rapidly infiltrate into surrounding healthy ciliated cells and Type II alveolar epithelial cells. Infected cells induce infiltration, proliferation, and activation of various inflammatory cells including macrophages capable of secreting cytokine substances that cause strong inflammation, leading to secondary symptoms (fever, cough, dyspnea, etc.).

The cytokines are proteins secreted by immune cells, and are involved in the immune responses by inducing proliferation of macrophages or promoting differentiation of secretory cells themselves. When cytokines are excessively secreted due to respiratory viral infection, they cause excessive immune responses to cause tissue or organ damage, which is called cytokine storm syndrome. Due to this cytokine storm syndrome, sequelae such as tissue damage, tissue fibrosis, and loss of tissue function remain after respiratory viral infection.

In patients with coronavirus disease-19, immune cell activation occurs in the lung tissue due to SARS-CoV-2 infection, and in particular, activated monocytes infiltrate into the lung tissue through the bloodstream, causing tissue damage due to excessive immune responses, apart from eliminating the virus. Cytokine storm syndrome may be the main cause of sequelae that remain after complete recovery from coronavirus disease-19.

The cytokines may be pro-inflammatory cytokines, and specific examples thereof may include interleukin, tumor necrosis factor, interferon, TGFβ, GM-CSF, G-CSF, etc. Non-limiting examples of the interleukin may include IL-1α, IL-1β, IL-2, IL-3, IL-4, IL-5, IL-6, IL-7, IL-8, etc., non-limiting examples of the tumor necrosis factor may include TNF-α, TNFβ, etc., and non-limiting examples of the interferon may include IFNα, IFNβ, IFNγ, etc.

As used herein, the term "sequelae following respiratory infectious diseases" refers to abnormal symptoms that appear in patients with respiratory infectious diseases independently after treatment of respiratory infectious diseases. In the present invention, the sequelae following respiratory infectious diseases may be specifically sequelae following respiratory viral infectious diseases, and more specifically sequelae following coronavirus disease-19 (COVID-19), but are not limited thereto.

The sequelae following respiratory infectious diseases of the present invention refer to pathological conditions such as tissue deformation or dysfunction remaining after the source of infection is removed, and the symptoms include fever, dyspnea, cough, pneumonia, pulmonary fibrosis, pain, myalgia, fatigue, inflammation, nervous system disorders, etc. In the present invention, the sequelae following respiratory infectious diseases may be caused by tissue damage due to excessive cytokine secretion, but are not limited thereto.

As used herein, the term "coronavirus disease-19 (COVID-19) sequelae (COVID-19 sequelae)" refer to sequelae occurring in patients after SARS-CoV-2 infection. In the case of coronavirus disease-19, patients who have been completely recovered are known to often complain about persistent symptoms such as chronic fatigue, pain, dyspnea, etc. Such coronavirus disease-19 sequelae are also called chronic coronavirus disease-19 (Long COVID), and coronavirus disease-19 as well as its sequelae are so severe that patients suffering from the coronavirus disease-19 sequelae are called "long-haulers" in the United States.

Specifically, coronavirus disease-19 sequelae may include, but are not limited to, fever, dyspnea, cough, pneumonia, pulmonary fibrosis, pain, myalgia, fatigue, inflammation, nervous system disorders, etc.

In particular, coronavirus disease-19 sequelae may be manifested by dysfunction and/or damage to the respiratory system, in particular, the lungs, but are not limited thereto. Specifically, in the lungs where inflammation and/or fibrosis is progressing, tissue damage that is difficult to recover occurs, and loss of function occurs. Reduced lung volume resulting from fibrosis may cause dyspnea, cough, pain, etc.

With respect to the objects of the present invention, the peptide or the long acting conjugate thereof according to the present invention may prevent abnormal organ damage occurring in respiratory virus-infected patients and/or may help the improvement and recovery of damaged organs, independent of the anti-viral activity, before and/or after complete recovery from respiratory viral infectious disease or coronavirus disease-19, or during the recovery.

As used herein, the term "pneumonia" refers to a condition in which inflammation occurs in the parenchymal tissue or alveoli of the lungs, and specifically refers to inflammation that occurs in patients with respiratory infectious diseases or in patients who have been recovered therefrom. With respect to the objects of the present invention, the pneumonia may refer to acute pneumonia caused by respiratory viral infection. Due to such chronic inflammation, damage and/or fibrosis symptoms may occur in the lung tissue.

As serious sequelae of coronavirus disease-19, post-COVID-19 pulmonary fibrosis is known.

Pulmonary fibrosis refers to a state in which the tissue becomes excessively fibrotic as it becomes out of normal control during the wound healing process after damage by various stresses (chemical stimuli, radiation, etc.) in the lungs. Pulmonary function may be expected to return back to normal in a person with a normal immune mechanism, but in patients with severe inflammation (pneumonia), bleeding and congestion occur in both lungs, making it difficult to restore the normal state, and fibrosis may occur due to adhesions. Particularly, in patients with respiratory infectious disease, excessive immune responses to infection occur, and fibrosis symptoms often develop as sequelae. It is known that pulmonary fibrosis along with lung damage and lung dysfunction due to excessive immune responses are more common in patients who have suffered from moderate or more severe coronavirus disease-19 symptoms.

Particularly, in patients with coronavirus disease-19, macrophages with the function of suppressing inflammation in the lungs are replaced by pro-inflammatory macrophages derived from blood mononuclear cells, and inflammasome complexes present in the lung epithelial cells or immune cells are activated, resulting in sequelae due to hyperimmune responses such as severe pneumonia and cytokine storm. Therefore, in order to reduce the sequelae of coronavirus disease-19 patients, it is important to suppress lung damage and fibrosis by suppressing the excessive immune responses.

The inflammasome complex (or inflammasome) is a multiprotein intracellular complex that activates interleukin-1b (IL-1b) and IL-18 which are pro-inflammatory cytokines, and is involved in immune responses such as inducing cell death called pyroptosis, etc. It is known that in patients with coronavirus disease-19, excessive cytokine secretion and cytokine storm occur due to the activity of the inflammasome complex, resulting in sequelae.

The peptide or the conjugate thereof according to the present invention may inhibit production of inflammasome complexes and activity thereof and may reduce secretion and/or expression of IL-1β, TNF-α, IFN-γ cytokines which are representative inflammatory factors expressed in patients with coronavirus disease-19, thereby preventing cytokine storm which occurs due to viral infection in patients with coronavirus disease-19, and also improving sequelae such as lung damage and pulmonary fibrosis. In other words, the peptide or the conjugate thereof according to the present invention may ameliorate excessive immune responses due to respiratory viral infection, thereby improving sequelae following respiratory viral infectious diseases by suppressing inflammation and fibrosis at the same time.

With respect to the objects of the present invention, the pharmaceutical composition including the peptide or the conjugate thereof according to the present invention may have one or more of the following characteristics when administered to an individual with sequelae following respiratory infectious diseases:

(i) alleviation of lung inflammation caused by coronaviral infection; and (ii) alleviation of post-COVID-19 pulmonary fibrosis accompanying pulmonary inflammation.

Specifically, the pharmaceutical composition may have one or more of the following characteristics when administered:

(i) a reduction in the lung inflammation score;

(ii) a reduction in the expression or secretion of pro-inflammatory cytokines;

(iii) a reduction in the pulmonary fibrotic area; and (iv) suppressed production of inflammasome complexes.

The characteristics of the pharmaceutical composition may include a reduction in the lung weight which has been increased due to fibrosis or a reduction in fiber deposition by the pharmaceutical composition including the peptide or the conjugate thereof according to the present invention, but are not limited thereto.

In the present invention, the cytokine may be any one or more selected from the group consisting of interleukin, tumor necrosis factor, and interferon, and specifically, the cytokine may be IL-1$\beta$, TNF-$\alpha$, or IFN-$\gamma$, but is not limited thereto.

The characteristics of the peptide (trigonal agonist) of the present invention may improve pulmonary inflammation which is a main cause of post-COVID-19 pulmonary fibrosis and may also directly improve pulmonary fibrosis (dual inhibitory action), indicating the effects of suppressing and improving post-COVID-19 pulmonary fibrosis which occurs as coronavirus disease-19 sequelae, and also indicating the prophylactic or therapeutic effects on coronavirus disease-19 sequelae.

Accordingly, the sequelae following respiratory infectious diseases may be post-COVID-19 pulmonary fibrosis, but are not limited thereto.

As used herein, the "post-COVID-19 pulmonary fibrosis", which is a pulmonary fibrosis occurring in patients with coronavirus disease-19, refers to a pathological condition involving tissue fibrosis found in the lungs of patients with coronavirus disease-19 during the convalescent phase of coronavirus disease-19. Inflammation and excessive immune responses (cytokine storm) of the lung tissue caused by viral infection and damage caused by fibrosis are assumed to be the causes thereof, but clear pathogenesis thereof has not been elucidated. Unlike common pulmonary fibrosis, which develops over months to years, post-COVID-19 pulmonary fibrosis can rapidly develop within days to months.

Meanwhile, the sequelae following respiratory infectious diseases include various neurological abnormalities such as loss of taste, change of consciousness, convulsion, stroke, cerebral hemorrhage, encephalitis, dementia, and delirium. It is also known that patients with severe infection are at the high risk of developing depression, obsessive-compulsive disorder, psychosis, Parkinson's disease, Alzheimer's disease, etc.

These neurological disorders are believed to be caused by a source of infection directly acting on the nervous system (direct infection), brain hypoxia due to decreased lung function, and damage to the nervous system due to an inflammatory response in the body.

For example, SARS-CoV-2 which is one example of the source of infection may bind to angiotensin converting enzyme 2 (ACE2) to suppress conversion of angiotensin 2 (angiotensin II) into angiotensin 1 (angiotensin I), resulting in an increase of angiotensin 2, leading to constriction of blood vessels, which may damage the kidneys, heart, brain, etc.

Alternatively, the source of infection (e.g., SARS-CoV-2) may cause excessive immune responses in the body to activate cytokines or various inflammatory substances, and typically, may induce a cytokine storm. Specifically, it has been reported that blood coagulation occurs and a blood clot is produced to cause stroke, nerve vasculitis occurs to cause nerve damage, or a cytokine storm directly damages the blood brain barrier (BBB), and various inflammatory materials pass through the damaged BBB to cause brain edema and brain damage. In other words, it is known that damage to various organs of the body, including the brain, may occur as a result of an excessive inflammatory response even if it is not a direct infection with the source of infection, and eventually, a nervous system disorder appears as sequelae following respiratory infectious diseases.

Since the pharmaceutical composition including the peptide or the conjugate thereof according to the present invention may alleviate inflammation in individuals with sequelae following respiratory infectious diseases, it may have the effect of suppressing, delaying, or restoring central nervous system damage caused by inflammation.

In the present invention, the pharmaceutical composition may be administered to an individual with a cytokine storm syndrome, sepsis, or organ failure caused by respiratory viral infection, thereby reducing cytokine secretion and/or expression and suppressing immune responses, and the pharmaceutical composition may be administered to an individual with symptoms of pneumonia and pulmonary fibrosis, after respiratory infection, but is not limited thereto.

The pharmaceutical composition of the present invention may include a pharmaceutically effective amount of a peptide having activities to a glucagon receptor, a GLP-1 receptor, and a GIP receptor, specifically a peptide including, essentially consisting of, or consisting of any one sequence of amino acid sequences of SEQ ID NOS: 1 to 102, but is not limited thereto.

The "peptide having activities to a glucagon receptor, a GLP-1 receptor, and a GIP receptor" may be used interchangeably with the term "trigonal agonist" or "peptide" as used herein.

The trigonal agonist having significant levels of activities to glucagon, GLP-1, and GIP receptors may exhibit, but is not particularly limited to, about 0.001% or more, about 0.01% or more, about 0.1% or more, about 1% or more, about 2% or more, about 3% or more, about 4% or more, about 5% or more, about 6% or more, about 7% or more, about 8% or more, about 9% or more, about 10% or more, about 20% or more, about 30% or more, about 40% or more, about 50% or more, about 60% or more, about 70% or more, about 80% or more, about 90% or more, about 100% or more, about 150% or more, about 200% or more of in vitro activities to one or more receptors, specifically two or more receptors, and more specifically all three receptors of glucagon, GLP-1, and GIP receptors, as compared with those of native ligands (native glucagon, native GLP-1, and native GIP) of the corresponding receptors. However, the range is not limited, as long as the trigonal agonist exhibits significant activities.

Here, with regard to the activities to the receptors, the in vitro activities to the receptors may be 0.001% or more, 0.01% or more, 0.1% or more, 1% or more, 2% or more, 3% or more, 4% or more, 5% or more, 6% or more, 7% or more, 8% or more, 9% or more, 10% or more, 20% or more, 30% or more, 40% or more, 50% or more, 60% or more, 70% or more, 80% or more, 90% or more, 100% or more, about 200% or more, as compared with those of the natives, but are not limited thereto.

As used herein, the term "about" includes all of the ranges including ±0.5, ±0.4, ±0.3, ±0.2, ±0.1, etc., and includes all values in a range equal to or similar to the value following the term "about", but is not limited thereto.

Meanwhile, the peptide included in the composition of the present invention is characterized by possessing one or more, two or more, and specifically all three activities of the following i) to iii), specifically significant activities:

i) activation of GLP-1 receptor; ii) activation of glucagon receptor; and iii) activation of GIP receptor.

Here, as an example of the activation of the receptor, the in vitro activities to the receptors may be about 0.1% or more, about 1% or more, about 2% or more, about 3% or more, about 4% or more, about 5% or more, about 6% or more, about 7% or more, about 8% or more, about 9% or more, about 10% or more, about 20% or more, about 30% or more, about 40% or more, about 50% or more, about 60% or more, about 70% or more, about 80% or more, about 90% or more, about 100% or more, about 150% or more, about 200% or more, as compared with those of the natives, but are not limited thereto. For a method of measuring the in vitro activity of the trigonal agonist, reference may be made to Experimental Example 1 of the present specification, but is not particularly limited thereto.

Further, the peptide may have an increased in vivo half-life, as compared to that of any of native GLP-1, native glucagon, and native GIP, but is not particularly limited thereto.

The peptide may be, but is not particularly limited to, a non-naturally occurring peptide.

In the present specification, although described as a peptide "consisting of" a specific sequence number, as long as the peptide may have an activity identical or corresponding to that of the peptide consisting of the amino acid sequence of the corresponding sequence number, addition of a meaningless sequence upstream or downstream of the amino acid sequence of the corresponding sequence number, a naturally occurring mutation, or a silent mutation therein is not excluded, and it will be apparent that those having such a sequence addition or mutation are also included in the scope of the present invention. In other words, even though there is a difference in some sequences, it may fall within the scope of the present invention as long as it exhibits homology above a predetermined level and exhibits activity to the glucagon receptor.

For example, the peptide of the present invention may include a peptide including any one amino acid sequence of SEQ ID NOS: 1 to 102, or a peptide (essentially) consisting of any one amino acid sequence of SEQ ID NOS: 1 to 102, or a peptide having at least 60% or more, 65% or more, 70% or more, 75% or more, 80% or more, 85% or more, 90% or more, 91% or more, 92% or more, 93% or more, 94% or more, or 95% or more sequence identity to any one amino acid sequence of SEQ ID NOS: 1 to 102. As long as the peptide has the effect of preventing or treating sequelae following respiratory infectious diseases, it is not limited to a particular sequence.

Examples of the trigonal agonist may include any amino acid sequence selected from the group consisting of SEQ ID NOS: 1 to 102, or may include any amino acid sequence selected from the group consisting of SEQ ID NOS: 1 to 11, 13 to 102, or may (essentially) consist of any amino acid sequence selected from the group consisting of SEQ ID NOS: 1 to 11, 13 to 102, but is not limited thereto.

In one specific embodiment, the trigonal agonist peptide may include, may essentially consist of, or may consist of any one amino acid sequence of SEQ ID NOS: 21 to 24, 28, 29, 31, 32, 37, 42, 43, 50, 51 to 54, 56, 58, 64 to 73, 75 to 79, 82, 83, 91, and 96 to 102, but is not limited thereto.

For one example, the trigonal agonist peptide may include, may essentially consist of, or may consist of any one amino acid sequence of SEQ ID NOS: 21, 22, 42, 43, 50, 64, 66, 67, 70, 71, 76, 77, 96, 97, and 100, but is not limited thereto.

For another example, the peptide may include, may essentially consist of, or may consist of any one amino acid sequence of SEQ ID NOS: 21, 22, 42, 43, 50, 66, 67, 77, 96, 97 and 100, but is not limited thereto.

In another specific embodiment, the trigonal agonist may include, may essentially consist of, or may consist of any one amino acid sequence selected from the group consisting of SEQ ID NOS: 21, 22, 27, 30 to 32, 34, 36, 37, 42, 43, 50 to 56, 58, 64 to 79, 83, 86, 91, 93, and 96 to 102, but is not limited thereto.

In still another specific embodiment, the trigonal agonist may include, may essentially consist of, or may consist of any one amino acid sequence selected from the group consisting of SEQ ID NOS: 21, 22, 31, 32, 37, 42, 43, 50, 53, 64, 65, 66, 67, 68, 69, 70, 71, 72, 73, 75, 76, 77, 79, 96, 97, 98, 99, 100, 101, and 102, but is not limited thereto.

Alternatively, the trigonal agonist may include a peptide having at least 60% or more, 65% or more, 70% or more, 75% or more, 80% or more, 85% or more, 90% or more, 91% or more, 92% or more, 93% or more, 94% or more, or 95% or more sequence identity to the above amino acid sequence. As long as the peptide has the effect of preventing or treating sequelae following respiratory infectious diseases, it is not limited to a particular sequence.

As used herein, the term "homology" or "identity" refers to the degree of relatedness between two given amino acid sequences or nucleotide sequences, and may be expressed as a percentage.

The terms "homology" and "identity" may be often used interchangeably with each other.

Whether any two peptide sequences have homology, similarity, or identity may be determined by a known computer algorithm such as the "FASTA" program using default parameters as in Pearson et al. (1988) Proc. Natl. Acad. Sci. USA 85:2444. Alternatively, it may be determined by the Needleman-Wunsch algorithm (Needleman and Wunsch, 1970, *J. Mol. Biol.* 48:443-453), which is performed using the Needleman program of the EMBOSS package (EMBOSS: The European Molecular Biology Open Software Suite, Rice et al., 2000, *Trends Genet.* 16:276-277) (version 5.0.0 or later) (GCG program package (Devereux, J., et al., *Nucleic Acids Research* 12:387 (1984)), BLASTP, BLASTN, FASTA (Atschul, S. F., et al., *J MOLEC BIOL* 215:403 (1990); *Guide to Huge Computers*, Martin J. Bishop, ed., Academic Press, San Diego, 1994, and CARILLO et al. (1988) *SIAM J Applied Math* 48:1073). For example, homology, similarity, or identity may be determined using BLAST or ClustalW of the National Center for Biotechnology Information.

The homology, similarity, or identity of peptides may be determined by comparing sequence information using, for example, the GAP computer program, such as Needleman et al. (1970), *J Mol Biol.* 48:443, as disclosed in Smith and Waterman, *Adv. Appl. Math* (1981) 2:482. In summary, the GAP program defines it as the value obtained by dividing the number of similarly aligned symbols (i.e., amino acids) by the total number of the symbols in the shorter of the two sequences. Default parameters for the GAP program may include (1) a unary comparison matrix (containing a value of 1 for identities and 0 for non-identities) and the weighted comparison matrix (or EDNAFULL (EMBOSS version of NCBI NUC4.4) substitution matrix) of Gribskov et al. (1986) *Nucl. Acids Res.* 14:6745, as disclosed in Schwartz and Dayhoff, eds., *Atlas Of Protein Sequence And Structure*, National Biomedical Research Foundation, pp. 353-358 (1979); (2) a penalty of 3.0 for each gap and an additional 0.10 penalty for each symbol in each gap (or a gap opening penalty of 10 and a gap extension penalty of 0.5); and (3) no penalty for end gaps. Accordingly, as used herein, the term "homology" or "identity" refers to the relatedness between sequences.

The peptide having activities to a glucagon receptor, a GLP-1 receptor, and a GIP receptor may include an intramolecular bridge (e.g., covalent crosslinking or non-covalent crosslinking), and specifically, it may be in a form including a ring. For example, the peptide may be in a form where a ring is formed between amino acids at positions 16 and 20 of the peptide, but it is not particularly limited thereto.

Non-limiting examples of the ring may include a lactam crosslinking (or a lactam ring).

Further, the peptide includes all of those which are modified to include an amino acid capable of forming a ring at the desired site so as to include a ring.

For example, the peptide may be a peptide, in which amino acid pairs at positions 16 and 20 of the peptide may be replaced by glutamic acid or lysine capable of forming a ring, respectively, but is not limited thereto.

The ring may be formed between side chains of amino acids within the peptide, for example, in the form of a lactam ring formed between a side chain of lysine and a side chain of a glutamic acid, but is not particularly limited thereto.

Examples of peptides prepared by a combination of these methods include a peptide having activity to a glucagon receptor, a GLP-1 receptor, and a GIP receptor, in which one or more in the amino acid sequence are different from those of the native glucagon and the alpha-carbon of the N-terminal amino acid residue has been removed, but the present invention is not limited thereto. A combination of various methods for analog preparation may be used to prepare the peptides applicable to the present invention.

Further, in the peptide of the present invention, a part of amino acids may be, but is not particularly limited to, substituted with another amino acid or a non-native compound to avoid the recognition by agonist degrading enzymes for increasing the in vivo half-life.

Specifically, the peptide may be a peptide where the in vivo half-life may be increased by avoiding the recognition by the degrading enzymes via substitution of the $2^{nd}$ amino acid sequence in the amino acid sequences of the peptide. However, any amino acid substitution or modification to avoid the recognition by in vivo degrading enzymes is included without limitation.

Further, such modification for the peptide preparation may include all of the modifications using L-type or D-type amino acids and/or non-natural amino acids; and/or a modification of native sequence, for example, a modification of a side chain functional group, an intramolecular covalent bonding, e.g., a ring formation between side chains, methylation, acylation, ubiquitination, phosphorylation, aminohexanation, biotinylation, etc.

Further, the modification may also include all of those where one or more amino acids are added to the amino and/or carboxy terminus of the trigonal agonist.

During the substitution or addition of amino acids, not only 20 amino acids commonly found in human proteins, but also atypical or non-naturally occurring amino acids may be used. Commercial sources of atypical amino acids may include Sigma-Aldrich, ChemPep Inc., and Genzyme Pharmaceuticals. The peptides including these amino acids and typical peptide sequences may be synthesized and purchased from commercial suppliers, e.g., American Peptide Company or Bachem (USA), or Anygen (Korea).

Amino acid derivatives may be obtained in the same manner, and for example, 4-imidazoacetic acid, etc. may be used.

Further, the trigonal agonist according to the present invention may be in the form of a variant where the N- and/or C-terminus, etc. thereof is chemically modified or protected by organic groups, or amino acids may be added to the terminus of the peptide, for its protection from proteases in vivo while increasing its stability.

In particular, in the case of a chemically-synthesized trigonal agonist, N- and C-termini thereof are electrically charged, and therefore, in order to remove the electric charge, the N-terminus may be acetylated and/or the C-terminus may be amidated, but the trigonal agonist is not particularly limited thereto.

Specifically, the N- or C-terminus of the peptide of the present invention may have an amine group ($-NH_2$) or a carboxyl group ($-COOH$), but is not limited thereto.

The peptide according to the present invention may include a peptide of which C-terminus may be amidated or may have a free carboxyl group ($-COOH$), or a peptide of which C-terminus may not be modified, but is not limited thereto.

In one specific embodiment, the peptide may be amidated at the C-terminus thereof, but is not limited thereto.

In one specific embodiment, the peptide may be aglycosylated, but is not limited thereto.

The peptide of the present invention may be synthesized by a solid-phase synthesis method, and may also be produced by a recombinant method, or may be prepared commercially, but is not limited thereto.

Further, the peptide of the present invention may be synthesized by a method well-known in the art, according to its length, e.g., by an automatic peptide synthesizer, and may also be produced by genetic engineering technology.

Specifically, the peptide of the present invention may be prepared by a standard synthesis method, a recombinant expression system, or any other method known in the art. Accordingly, the peptide of the present invention may be synthesized by many methods including, for example, the methods described below:

(a) a method of synthesizing a peptide by a solid-phase or liquid-phase method stepwise or by fragment assembly, followed by isolation and purification of the final peptide product; or (b) a method of expressing a nucleic acid construct encoding a peptide in a host cell and recovering the expression product from the host cell culture; or (c) a method of performing an in vitro cell-free expression of a nucleic acid construct encoding a peptide and recovering the expression product therefrom; or a method of obtaining peptide fragments by any combination of the methods (a), (b), and (c), obtaining a peptide by linking the peptide fragments, and then recovering the peptide.

These descriptions may also be applied to other specific embodiments or aspects of the present invention, but are not limited thereto.

Further, the peptide having activities to a glucagon receptor, a GLP-1 receptor, and a GIP receptor may be in the form of a long-acting conjugate, in which a biocompatible material capable of increasing the in vivo half-life thereof is linked to the peptide having activities to a glucagon receptor, a GLP-1 receptor, and a GIP receptor. In the present invention, the biocompatible material may be used interchangeably with a carrier. The peptide included in the pharmaceutical composition of the present invention may be in the form of the long-acting conjugate.

In the present invention, the conjugate of the peptide may exhibit increased durability of the efficacy, as compared with the peptide to which the carrier is not linked, and in the present invention, such a conjugate is referred to as a "long-acting conjugate" or "conjugate".

In one specific embodiment of the present invention, the long-acting conjugate may have a form, in which an immunoglobulin Fc region as a biocompatible material is linked to the peptide having activities to a glucagon receptor, a GLP-1 receptor, and a GIP receptor. Specifically, in the conjugate, the immunoglobulin Fc region is covalently linked to the peptide having activities to a glucagon receptor, a GLP-1 receptor, and a GIP receptor via a linker, but is not particularly limited thereto.

Meanwhile, the conjugate may be non-naturally occurring.

In one specific embodiment of the present invention, the long-acting conjugate may be represented by the following Chemical Formula 1, but is not limited thereto:

X-L-F [Chemical Formula 1]

wherein X is a peptide including any one amino acid sequence of SEQ ID NOS: 1 to 102;

L is a linker including ethylene glycol repeating units,

F is an immunoglobulin Fc region, and

- represents a covalent linkage between X and L, and between L and F.

X of the long-acting conjugate of Chemical Formula 1 may be the above-described peptide (trigonal agonist) having activities to a glucagon receptor, a GLP-1 receptor, and a GIP receptor, specifically a peptide including any one amino acid sequence of SEQ ID NOS: 1 to 102, or a peptide essentially consisting of or consisting of any one amino acid sequence of SEQ ID NOS: 1 to 102, but is not limited thereto.

The long-acting conjugate of Chemical Formula 1 may have a form, in which the peptide including any one amino acid sequence of SEQ ID NOS: 1 to 102 and an immunoglobulin Fc region are linked to each other via a linker, wherein the conjugate may exhibit increased durability of efficacy, as compared with the peptide including any one amino acid sequence of SEQ ID NOS: 1 to 102 which is not linked to the immunoglobulin Fc region.

The conjugate of the present invention may exhibit significant activities to a glucagon receptor, a GLP-1 receptor, and a GIP receptor even in the form of the conjugate, thereby exhibiting the effect of preventing or treating sequelae following respiratory infectious diseases.

Specifically, the conjugate of the present invention may exhibit 0.01% or more, 0.1% or more, 0.2% or more, 0.5% or more, 0.7% or more, 1% or more, 2% or more, 3% or more, 4% or more, 5% or more, 6% or more, 7% or more, 8% or more, 9% or more, 10% or more, 20% or more, 30% or more, 40% or more, 50% or more, 60% or more, 70% or more, 80% or more, 90% or more, 100% or more in vitro activity to a glucagon receptor, a GLP-1 receptor, and/or a GIP receptor, as compared to the native form thereof, but is not limited thereto.

With respect to the objects of the present invention, the peptide or the conjugate thereof may exhibit 0.1% or more, 0.2% or more, 0.5% or more, 0.7% or more, 1% or more, 2% or more, 3% or more, 4% or more, 5% or more, 10% or more, 20% or more, 30% or more, 40% or more, 50% or more, 60% or more, 70% or more, 80% or more, 90% or more, 100% or more activity to a glucagon receptor, a GLP-1 receptor, and/or a GIP receptor, as compared to the native form thereof, but is not limited thereto.

The composition of the present invention may include (i) the peptide having activities to a glucagon receptor, a GLP-1 receptor, and a GIP receptor or (ii) the long-acting conjugate of the peptide having activities to a glucagon receptor, a GLP-1 receptor, and a GIP receptor. The long-acting conjugate may exhibit the excellent prophylactic or therapeutic effect on sequelae following respiratory infectious diseases, based on the increased in vivo durability.

In the long-acting conjugate of Chemical Formula 1, the linkage between X which is the peptide including any one amino acid sequence of SEQ ID NOS: 1 to 102 and the immunoglobulin Fc region may be a physical or chemical bond, or a non-covalent or covalent bond, specifically a covalent bond, but is not limited thereto.

Further, X may be linked with F via a linker (L). More specifically, X and L, and L and F may be linked to each other via a covalent bond. In this regard, the conjugate is a conjugate, in which X, L, and F are linked via covalent bonds, respectively, as in the order of Chemical Formula 1.

F may be an immunoglobulin Fc region, and more specifically, the immunoglobulin Fc region may be derived from IgG, but is not particularly limited thereto.

In one specific embodiment of the present invention, F (immunoglobulin Fc region) is a dimer consisting of two polypeptide chains, and has a structure in which one end of L is linked to only one polypeptide chain of the two polypeptide chains, but is not limited thereto.

In the present invention, the "immunoglobulin Fc region" refers to a region including a heavy chain constant region 2(CH2) and/or a heavy chain constant region 3(CH3), excluding heavy chain and light chain variable regions of the immunoglobulin. The immunoglobulin Fc region may be an element constituting the moiety of the conjugate of the present invention.

As used herein, the Fc region encompasses not only a native sequence obtained from papain digestion of an immunoglobulin, but also derivatives thereof, for example, variants, in which one or more amino acid residues in the native sequence are converted by deletion, insertion, non-conservative or conservative substitution, or a combination thereof, and thus become different from the native sequence, etc. The above derivatives, substituents, and variants are required to retain FcRn-binding ability. In the present invention, F may be a human immunoglobulin region, but is not limited thereto. F (immunoglobulin Fc region) has a structure in which two polypeptide chains are linked to each other via a disulfide bond, only via a nitrogen atom of one chain of the two chains, but is not limited thereto. The linkage via the nitrogen atom may be linked via reductive amination to an epsilon amino group of lysine or the N-terminal amino group.

The reductive amination reaction refers to a reaction in which an amine group or an amino group of a reactant reacts with an aldehyde (i.e., a functional group capable of reductive amination) of another reactant to produce an amine, and then forms an amine bond by a reduction reaction. It is an organic synthesis reaction well known in the art.

In one specific embodiment, F may be linked via a nitrogen atom of the N-terminal proline thereof, but is not limited thereto.

The immunoglobulin Fc region may be an element constituting the moiety of the conjugate of Chemical Formula 1 of the present invention, and specifically, it may correspond to F in Chemical Formula 1.

Such an immunoglobulin Fc region may include a hinge region in the heavy chain constant region, but is not limited thereto.

In the present invention, the immunoglobulin Fc region may include a specific hinge sequence at the N-terminus.

As used herein, the term "hinge sequence" refers to a region that is located in the heavy chain and forms a dimer of the immunoglobulin Fc region through a disulfide bond (inter-disulfide bond).

In the present invention, the hinge sequence may be altered to have only one cysteine residue by deleting a part in a hinge sequence having the following amino acid sequence, but is not limited thereto:

(SEQ ID NO: 103)
Glu-Ser-Lys-Tyr-Gly-Pro-Pro-Cys-Pro-Ser-Cys-Pro.

The hinge sequence may include only one cysteine residue by deleting a cysteine residue at position 8 or 11 in the hinge sequence of SEQ ID NO: 103. The hinge sequence of the present invention may include only one cysteine residue and may consist of 3 to 12 amino acids, but is not limited thereto. More specifically, the hinge sequence of the present invention may have the following sequence:

(SEQ ID NO: 104)
Glu-Ser-Lys-Tyr-Gly-Pro-Pro-Pro-Ser-Cys-Pro, (SEQ ID NO: 105)
Glu-Ser-Lys-Tyr-Gly-Pro-Pro-Cys-Pro-Ser-Pro, (SEQ ID NO: 106)
Glu-Ser-Lys-Tyr-Gly-Pro-Pro-Cys-Pro-Ser, (SEQ ID NO: 107)
Glu-Ser-Lys-Tyr-Gly-Pro-Pro-Cys-Pro-Pro, (SEQ ID NO: 108)
Lys-Tyr-Gly-Pro-Pro-Cys-Pro-Ser, (SEQ ID NO: 109)
Glu-Ser-Lys-Tyr-Gly-Pro-Pro-Cys, (SEQ ID NO: 110)
Glu-Lys-Tyr-Gly-Pro-Pro-Cys, (SEQ ID NO: 111)
Glu-Ser-Pro-Ser-Cys-Pro,

-continued (SEQ ID NO: 112)
Glu-Pro-Ser-Cys-Pro, (SEQ ID NO: 113)
Pro-Ser-Cys-Pro, (SEQ ID NO: 114)
Glu-Ser-Lys-Tyr-Gly-Pro-Pro-Ser-Cys-Pro, (SEQ ID NO: 115)
Lys-Tyr-Gly-Pro-Pro-Pro-Ser-Cys-Pro, (SEQ ID NO: 116)
Glu-Ser-Lys-Tyr-Gly-Pro-Ser-Cys-Pro, (SEQ ID NO: 117)
Glu-Ser-Lys-Tyr-Gly-Pro-Pro-Cys, (SEQ ID NO: 118)
Lys-Tyr-Gly-Pro-Pro-Cys-Pro, (SEQ ID NO: 119)
Glu-Ser-Lys-Pro-Ser-Cys-Pro, (SEQ ID NO: 120)
Glu-Ser-Pro-Ser-Cys-Pro, (SEQ ID NO: 121)
Glu-Pro-Ser-Cys, (SEQ ID NO: 122)
Ser-Cys-Pro.

More specifically, the hinge sequence may include an amino acid sequence of SEQ ID NO: 113 (Pro-Ser-Cys-Pro) or SEQ ID NO: 122 (Ser-Cys-Pro), but is not limited thereto.

The immunoglobulin Fc region of the present invention may form a dimer by two molecules of immunoglobulin Fc chains due to the presence of the hinge sequence, and the conjugate of Chemical Formula 1 may have a form, in which one end of the linker is linked to one chain of the dimeric immunoglobulin Fc region, but is not limited thereto.

As used herein, the term "N-terminus" refers to the amino terminal of a protein or polypeptide, and may include the extreme end of the amino terminus or up to 1, 2, 3, 4, 5, 6, 7, 8, 9, or 10 or more amino acids from the extreme end. The immunoglobulin Fc region of the present invention may include the hinge sequence at the N-terminus, but is not limited thereto.

Further, the immunoglobulin Fc region of the present invention may be an extended Fc region including a part or the entirety of the heavy chain constant region 1 (CH1) and/or light chain constant region 1 (CL1), excluding the heavy chain and light chain variable regions of an immunoglobulin, as long as it has an effect substantially equivalent or improved, as compared to its native form. Further, the immunoglobulin Fc region may be a region in which a part of a significantly long amino acid sequence corresponding to CH2 and/or CH3 is removed.

For example, the immunoglobulin Fc region of the present invention may be 1) CH1 domain, CH2 domain, CH3 domain, and CH4 domain, 2) CH1 domain and CH2 domain, 3) CH1 domain, and CH3 domain, 4) CH2 domain and CH3 domain, 5) a combination between one or two or more domains among CH1 domain, CH2 domain, CH3 domain and CH4 domain, and an immunoglobulin hinge region (or a part of the hinge region), and 6) a dimer between each domain of the heavy chain constant region and the light chain constant region, but is not limited thereto.

In the present invention, the immunoglobulin Fc region may be a dimer or multimer consisting of single-chain immunoglobulins consisting of domains of the same origin, but is not limited thereto.

Further, in one specific embodiment, the immunoglobulin Fc region F is a dimer consisting of two polypeptide chains, wherein the dimeric Fc region F and X may be covalently linked to each other via one identical linker L including ethylene glycol repeating units. In a specific embodiment, X is covalently linked to only one polypeptide chain of the two polypeptide chains of the dimeric Fc region F via the linker L. In a more specific embodiment, only one molecule of X is covalently linked via L to one polypeptide chain, to which X is linked, of the two polypeptide chains of the dimeric Fc region F. In the most specific embodiment, F is a homodimer.

In another specific embodiment, the immunoglobulin Fc region F is a dimer consisting of two polypeptide chains, and one end of L is linked to only one polypeptide chain of the two polypeptide chains, but is not limited thereto.

In the long-acting conjugate of another embodiment of the present invention, it is also possible for two molecules of X to bind symmetrically to one Fc region in a dimeric form. In this regard, the immunoglobulin Fc region and X may be linked to each other via the linker (L), but are not limited to the above-described examples.

Further, the immunoglobulin Fc region of the present invention includes the native amino acid sequence as well as sequence derivatives thereof. The amino acid sequence derivative means that one or more amino acid residues in the natural amino acid sequence have a different sequence due to deletion, insertion, non-conservative or conservative substitution, or a combination thereof.

For example, amino acid residues at positions 214 to 238, 297 to 299, 318 to 322, or 327 to 331 in IgG Fc, which are known to be important for linkage, may be used as the sites suitable for variation.

Further, various types of derivatives are possible, for example, those where the site capable of forming a disulfide bond is removed, those where several N-terminal amino acids are removed from native Fc, those where a methionine residue is added to the N-terminus of native Fc, etc. Further, complement binding sites, e.g., C1q binding sites, or antibody-dependent cell-mediated cytotoxicity (ADCC) sites may be removed to remove the effector function. The techniques for preparing the sequence derivatives of the immunoglobulin Fc region are disclosed in International Publication Nos. WO 97/34631, WO 96/32478, etc.

Amino acid exchanges in a protein or peptide that do not alter the entire activity of a molecule are well known in the art (H. Neurath, R. L. Hill, The Proteins, Academic Press, New York, 1979). The most common exchanges occur between amino acid residues of Ala/Ser, Val/Ile, Asp/Glu, Thr/Ser, Ala/Gly, Ala/Thr, Ser/Asn, Ala/Val, Ser/Gly, Thy/Phe, Ala/Pro, Lys/Arg, Asp/Asn, Leu/Ile, Leu/Val, Ala/Glu, and Asp/Gly. In some cases, amino acids may be modified by phosphorylation, sulfation, acrylation, glycosylation, methylation, farnesylation, acetylation, amidation, etc.

The Fc derivatives described above may be those which exhibit the same biological activity as that of the Fc region of the present invention, and have increased structural stability of the Fc region against heat, pH, etc.

Further, such an Fc region may be obtained from a native type isolated from humans or animals such as cows, goats, pigs, mice, rabbits, hamsters, rats, guinea pigs, etc., or may be their recombinants or derivatives obtained from transformed animal cells or microorganisms. Herein, the method of obtaining from a native form is a method of isolating whole immunoglobulins from human or animal organisms and then treating them with a protease. When treated with papain, the native form is digested into Fab and Fc, and when treated with pepsin, it is cleaved into pF'c and $F(ab)_2$. Fc or pF'c may be isolated using size-exclusion chromatography, etc. In a more specific embodiment, the Fc region may be a recombinant immunoglobulin Fc region, in which a human-derived Fc region is obtained from a microorganism.

In addition, the immunoglobulin Fc region may have natural glycans or increased or decreased glycans compared to the natural type, or be in a deglycosylated form. The increase, decrease, or removal of glycans of the immunoglobulin Fc may be achieved by any methods commonly used in the art such as a chemical method, an enzymatic method, and a genetic engineering method using a microorganism. In this regard, the immunoglobulin Fc region obtained by removing glycans shows a significant decrease in binding affinity to a complement cl q and a decrease in or loss of antibody-dependent cytotoxicity or complement-dependent cytotoxicity, and thus unnecessary immune responses are not induced thereby in living organisms. Based thereon, a deglycosylated or aglycosylated immunoglobulin Fc region may be more suitable as a drug carrier in view of the objects of the present invention.

As used herein, the term "deglycosylation" refers to a Fc region from which glycan is removed using an enzyme and the term "aglycosylation" refers to an unglycosylated Fc region produced in prokaryotes, in a more specific embodiment, *E. coli*.

Meanwhile, the immunoglobulin Fc region may be derived from humans or animals including cows, goats, pigs, mice, rabbits, hamsters, rats, guinea pigs, etc., and in a more specific embodiment, it may be derived from humans.

Further, the immunoglobulin Fc region may be an Fc region derived from IgG, IgA, IgD, IgE, IgM, or a combination or hybrid thereof. In a more specific embodiment, it may be derived from IgG or IgM, which are the most abundant proteins in human blood, and in an even more specific embodiment, it may be derived from IgG, which is known to enhance the half-lives of ligand-binding proteins. In a more specific embodiment, the immunoglobulin Fc region may be an IgG4 Fc region, and in an even more specific embodiment, the immunoglobulin Fc region may be an aglycosylated Fc region derived from a human IgG4, but is not limited thereto.

Further, in one specific embodiment, the immunoglobulin Fc region is a human IgG4 Fc region, and may be in the form of a homodimer, in which two monomers are linked via disulfide bonds (inter-chain form) between cysteines which are amino acids at position 3 of each monomer. In this regard, each monomer of the homodimer has or may have independent two inner disulfide bonds (intra-chain), i.e., a disulfide bond formed between cysteines at positions 35 and 95 and a disulfide bond formed between cysteines at positions 141 and 199. The number of amino acids of each monomer may be 221 amino acids, and amino acids forming the homodimer may consist of a total of 442 amino acids, but are not limited thereto. Specifically, with regard to the immunoglobulin Fc fragment, two monomers, each having an amino acid sequence of SEQ ID NO: 123 (consisting of 221 amino acids), form a homodimer via disulfide bonds between cysteines at position 3 of each monomer, and the monomers of the homodimer may form each independently an intra-chain disulfide bond between cysteines at positions 35 and 95, and an intra-chain disulfide bond between cysteines at positions 141 and 199, but is not limited thereto.

F of Chemical Formula 1 may include a monomer of the amino acid sequence of SEQ ID NO: 123, and F may be a homodimer of the monomer of the amino acid sequence of SEQ ID NO: 123, but is not limited thereto.

For example, the immunoglobulin Fc region may be a homodimer including an amino acid sequence of SEQ ID NO: 124 (consisting of 442 amino acids), but is not limited thereto.

In one specific embodiment, the immunoglobulin Fc region and X may not be glycosylated, but are not limited thereto.

Meanwhile, as used herein, the term "combination", in connection with the immunoglobulin Fc region, means that polypeptides encoding single-chain immunoglobulin Fc regions of the same origin are linked to a single-chain polypeptide of a different origin to form a dimer or multimer. In other words, a dimer or a multimer may be prepared from two or more regions selected from the group consisting of Fc regions of IgG Fc, IgA Fc, IgM Fc, IgD Fc, and IgE.

As used herein, the term "hybrid" means that sequences corresponding to two or more immunoglobulin Fc regions of different origins are present in a single-chain immunoglobulin constant region. In the present invention, various hybrid forms are possible. In other words, the hybrid domain may be composed of one to four domains selected from the group consisting of CH1, CH2, CH3, and CH4 of IgG Fc, IgM Fc, IgA Fc, IgE Fc and IgD Fc, and may include a hinge region.

Meanwhile, IgG may be divided into the IgG1, IgG2, IgG3, and IgG4 subclasses, and the present invention may include combinations or hybrids thereof, specifically the IgG2 and IgG4 subclasses, and most specifically the Fc fragment of IgG4, which rarely has effector functions such as complement-dependent cytotoxicity (CDC).

Further, the above-described conjugate may have increased durability of efficacy, as compared with native GLP-1, GIP, glucagon, or as compared with X not modified with F, and such a conjugate may be not only in the above-described form but also in a form, in which it is encapsulated in biodegradable nanoparticles, but is not limited thereto.

Meanwhile, in Chemical Formula 1, L is a non-peptidyl linker, for example, a linker including ethylene glycol repeating units.

As used herein, the term "non-peptidyl linker" includes a biocompatible polymer in which two or more repeating units are conjugated. The repeating units are linked to each other through any covalent bond, not a peptide bond. The non-peptidyl polymer may be an element constituting the moiety of the conjugate of the present invention, and corresponds to L in Chemical Formula 1.

The non-peptidyl linker applicable in the present invention may be used without limitation as long as it is a polymer resistant to proteolytic enzymes in vivo. In the present invention, the non-peptidyl linker may be used interchangeably with a non-peptidyl polymer.

Further, the non-peptidyl linker of the present invention binding to the polypeptide corresponding to F may be one type of polymer as well as a combination of different types of polymers.

In one specific embodiment, the conjugate may be a conjugate in which F and X are covalently linked together via the non-peptidyl linker, which includes, at both ends, reactive groups capable of binding to F, specifically the immunoglobulin Fc region, and X, specifically the trigonal agonist.

Specifically, in the present invention, the non-peptidyl linker may include reactive groups at ends thereof to form a conjugate through a reaction with other components constituting the conjugate. When the non-peptidyl linker having reactive functional groups at both ends bind to X and F of Chemical Formula 1 via respective reactive groups to form the conjugate, the non-peptidyl linker or non-peptidyl polymer may be referred to as a non-peptidyl polymer linker moiety or a non-peptidyl linker moiety.

The non-peptidyl linker may be, but is not particularly limited to, a linker including ethylene glycol repeating units, for example, a polyethylene glycol linker. Derivatives thereof that are known in the art and derivatives that may be easily prepared by ordinary skill in the art are also included in the scope of the present invention.

As used herein, the "polyethylene glycol linker" includes a biocompatible polymer in which two or more ethylene glycol repeating units are bound. The repeating units are linked to each other through not a peptide bond but any covalent bond. The polyethylene glycol linker may be an element constituting the moiety of the conjugate of the present invention, and corresponds to L in Chemical Formula 1.

Specifically, L (polyethylene glycol linker) may be a linker including ethylene glycol repeating units, for example, polyethylene glycol, but is not limited thereto. As used herein, the polyethylene glycol is a term including all of an ethylene glycol homopolymer, a PEG copolymer, or a monomethyl-substituted PEG polymer (mPEG), but is not particularly limited thereto. Derivatives thereof that are known in the art and derivatives that may be easily prepared by ordinary skill in the art are also included in the scope of the present invention.

The polyethylene glycol linker may include the ethylene glycol repeating units while including, at the ends thereof, functional groups used in the preparation of a conjugate before being formed into the conjugate. In the long-acting conjugate according to the present invention, X and F may be linked to each other though the functional groups, but it is not limited thereto. In the present invention, the non-peptidyl linker may include two or three or more functional groups, wherein the respective functional groups are the same as or different from each other, but is not limited thereto.

Specifically, the linker may be polyethylene glycol (PEG) represented by the following Chemical Formula 2, but is not limited thereto:

[Chemical Formula 2]

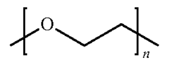

wherein n=10 to 2400, n=10 to 480, or n=50 to 250, but is not limited thereto.

In the long-acting conjugate, the PEG moiety may include a structure of $-(CH_2CH_2O)_n-$ and an oxygen atom interposed between the linking element and $-(CH_2CH_2O)_n-$, but is not limited thereto.

In one specific embodiment, the ethylene glycol repeating unit may be represented by, for example, $[OCH_2CH_2]_n$, wherein the value of n is a natural number and may be determined such that an average molecular weight, for example, a number average molecular weight of the $[OCH_2CH_2]_n$ site in the peptide conjugate is more than 0 kDa to about 100 kDa, but is not limited thereto. In another embodiment, the value of n is a natural number and may be determined such that an average molecular weight, for example, a number average molecular weight of the $[OCH_2CH_2]_n$ site in the peptide conjugate may be about 1 kDa to about 100 kDa, about 1 kDa to about 80 kDa, about 1 kDa to about 50 kDa, about 1 kDa to about 30 kDa, about 1 kDa to about 25 kDa, about 1 kDa to about 20 kDa, about 1 kDa to about 15 kDa, about 1 kDa to about 13 kDa, about 1 kDa to about 11 kDa, about 1 kDa to about 10 kDa, about 1 kDa to about 8 kDa, about 1 kDa to about 5 kDa, about 1 kDa to about 3.4 kDa, about 3 kDa to about 30 kDa, about 3 kDa to about 27 kDa, about 3 kDa to about kDa, about 3 kDa to about 22 kDa, about 3 kDa to about 20 kDa, about 3 kDa to about 18 kDa, about 3 kDa to about 16 kDa, about 3 kDa to about 15 kDa, about 3 kDa to about 13 kDa, about 3 kDa to about 11 kDa, about 3 kDa to about kDa, about 3 kDa to about 8 kDa, about 3 kDa to about 5 kDa, about 3 kDa to about 3.4 kDa, about 8 kDa to about 30 kDa, about 8 kDa to about 27 kDa, about 8 kDa to about 25 kDa, about 8 kDa to about 22 kDa, about 8 kDa to about kDa, about 8 kDa to about 18 kDa, about 8 kDa to about 16 kDa, about 8 kDa to about 15 kDa, about 8 kDa to about 13 kDa, about 8 kDa to about 11 kDa, about 8 kDa to about 10 kDa, about 9 kDa to about 15 kDa, about 9 kDa to about 14 kDa, about 9 kDa to about 13 kDa, about 9 kDa to about 12 kDa, about 9 kDa to about 11 kDa, about 9.5 kDa to about 10.5 kDa, or about 10 kDa, but is not limited thereto.

Further, in one specific embodiment, the conjugate may have a structure in which the peptide (X) and the immunoglobulin Fc region (F) are covalently linked to each other via the linker including ethylene glycol repeating units, but is not limited thereto.

Further, in one specific embodiment, the long-acting conjugate may have a structure in which the peptide (X) of the present invention and the immunoglobulin Fc region (F) are covalently linked to each other via the linker (L) including ethylene glycol repeating units, but is not limited thereto.

The non-peptidyl linker that may be used in the present invention may be used without limitation as long as it is a polymer including ethylene glycol repeating units, which is resistant to proteolytic enzymes in vivo. A molecular weight of the non-peptidyl polymer may be in the range of more than 0 kDa and about 100 kDa, in the range of about 1 kDa to about 100 kDa, specifically in the range of about 1 kDa to about 20 kDa, or in the range of about 1 kDa to about 10 kDa, but is not limited thereto. Further, the non-peptidyl linker of the present invention binding to the polypeptide corresponding to F may be one type of polymer as well as a combination of different types of polymers.

Specifically, the non-peptidyl linker may have reactive groups at both ends thereof in a state where F and X are not bound thereto, and may bind with F and X via the reactive groups.

In one specific embodiment, both ends of the linker may bind to a thiol group, an amino group, or a hydroxyl group of the immunoglobulin Fc region and a thiol group, an amino group, an azide group, or a hydroxyl group of the peptide (X), but are not limited thereto.

Specifically, the linker may include, at both ends thereof, reactive groups capable of binding to the immunoglobulin Fc region and the peptide (X), respectively, specifically reactive groups capable of binding to a thiol group of cysteine; an amino group located at the N-terminus, lysine, arginine, glutamine, and/or histidine; and/or a hydroxyl group at the C-terminus of the immunoglobulin Fc region; and a thiol group of cysteine; an amino group of lysine, arginine, glutamine, and/or histidine; an azide group of azido-lysine; and/or a hydroxyl group of the peptide (X), but is not limited thereto.

More specifically, the reactive group of the linker may be one or more selected from the group consisting of an aldehyde group, a maleimide group, and a succinimide derivative, but is not limited thereto.

In the above, examples of the aldehyde group may include a propionaldehyde group, or a butyraldehyde group, but are not limited thereto.

In the above, examples of the succinimide derivative may include succinimidyl valerate, succinimidyl methylbutanoate, succinimidyl methylpropionate, succinimidyl butanoate, succinimidyl propionate, N-hydroxysuccinimide, hydroxy succinimidyl, succinimidyl carboxymethyl, or succinimidyl carbonate, but are not limited thereto.

The linker may be linked to the immunoglobulin Fc region F and the peptide (trigonal agonist) X via the reactive groups to be converted into a linker moiety.

Further, a final product produced by reductive amination via aldehyde bonds is more stable than a linkage formed by an amide bond. The aldehyde reactive group selectively reacts with the N-terminus at low pH while forming a covalent bond with a lysine residue at high pH, e.g., at a pH of 9.0.

In addition, the reactive groups of both ends of the non-peptidyl linker may be the same as or different from each other, for example, aldehyde groups may be provided at both ends, and a maleimide group may be provided at one end and an aldehyde group, a propionaldehyde group, or a butyraldehyde group may be provided at the other end. However, the reactive groups are not particularly limited as long as F, specifically the immunoglobulin Fc region, and X may be linked to the respective ends of the non-peptidyl linker.

For example, the non-peptidyl linker may include a maleimide group at one end and an aldehyde group, a propionaldehyde group, or a butyraldehyde group at the other end, as reactive groups.

When polyethylene glycol having hydroxyl reactive groups at both ends is used as the non-peptidyl polymer, the long-acting protein conjugate according to the present invention may be prepared by activating the hydroxyl groups to various reactive groups by known chemical reactions, or using commercially available polyethylene glycol having modified reactive groups.

In a specific embodiment, the non-peptidyl polymer may be linked to a cysteine residue of X, more specifically a —SH group of cysteine, but is not limited thereto.

For example, the non-peptidyl polymer may be linked to a cysteine residue at position 10, a cysteine residue at position 13, a cysteine residue at position 15, a cysteine residue at position 17, a cysteine residue at position 19, a cysteine residue at position 21, a cysteine residue at position 24, a cysteine residue at position 28, a cysteine residue at position 29, a cysteine residue at position 30, a cysteine residue at position 31, a cysteine residue at position 40, a cysteine residue at position 41 in the peptide corresponding to X, but is not particularly limited thereto. Specifically, the reactive group of the non-peptidyl polymer may be linked to the —SH group of the cysteine residue, and all of those described above will be applied to the reactive group.

Specifically, the reactive group of the non-peptidyl polymer may be linked to the —SH group of the cysteine residue, and all of those described above will be applied to the reactive group.

Further, in the conjugate, the reactive group of the non-peptidyl polymer may be linked to —$NH_2$ located at the N-terminus of the immunoglobulin Fc region, but this is merely an example.

When maleimide-PEG-aldehyde is used, the maleimide group may be linked to the —SH group of the peptide via a thioether bond, and the aldehyde group may be linked to the —$NH_2$ group of the immunoglobulin Fc region via a reductive alkylation, but is not limited thereto. This is merely an example.

Through such reductive alkylation, the N-terminal amino group of the immunoglobulin Fc region is linked to the oxygen atom located at one end of the PEG through a linker functional group having a structure of —$CH_2CH_2CH_2$— to form a structure of -PEG-O—$CH_2CH_2CH_2NH$-immunoglobulin Fc. Through the thioether bond, a structure may be formed in which one end of the PEG is linked to the sulfur atom located in the cysteine of the peptide. The thioether bond described above may include a structure of

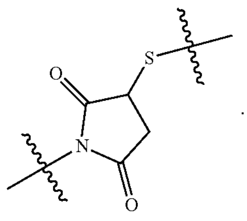 [SMILES: *SC1CC(=O)N(*)C1=O]

However, the present invention is not particularly limited to the above-described example, and this is merely an example.

Further, in the conjugate, the reactive group of the linker may be linked to —$NH_2$ located at the N-terminus of the immunoglobulin Fc region, but this is merely an example.

Further, in the conjugate, the peptide according to the present invention may be linked to the linker having reactive groups via the C-terminus, but this is merely an example.

As used herein, the term "C-terminus" refers to a carboxy terminus of the peptide, and with respect to the objects of the present invention, it refers to a site capable of binding with the linker. For example, the C-terminus may include all of an amino acid residue at the extreme end of the C-terminus and amino acid residues near the C-terminus, and specifically it may include the $1^{st}$ to $20^{th}$ amino acid residues from the extreme end, but the C-terminus is not limited thereto.

Further, the above-described conjugate may have increased durability of efficacy, as compared with X not modified with F, and such a conjugate may be not only in the above-described form but also in a form, in which it is encapsulated in biodegradable nanoparticles.

Meanwhile, with regard to the above-described trigonal agonist and the long-acting conjugate thereof, the disclosures of International Publication Nos. WO 2017/116204 and WO 2017/116205 are incorporated by reference herein in their entirety.

Unless otherwise indicated, detailed descriptions or techniques of the claims regarding the "peptide" according to the present invention or the "conjugate", in which the peptide is covalently linked to a biocompatible material, may be applied not only to the peptide or conjugate but also a salt of the peptide or conjugate (e.g., a pharmaceutically acceptable salt of the peptide), or a solvate form thereof. Thus, although only "peptide" or "conjugate" is described in the specification, descriptions thereof may also be applied to particular salts thereof, particular solvates thereof, and solvates of the particular salts. Such salts may be, for example, in the form of a pharmaceutically acceptable salt. Types of the salts are not particularly limited. However, salts may be in a safe and effective form in individuals, for example, mammals, but are not limited thereto.

Types of the salts are not particularly limited. However, salts may be in a safe and effective form in individuals, for example, mammals, but are not limited thereto.

The term, "pharmaceutically acceptable" refers to a substance that may be effectively used for the intended use within the scope of a pharmaco-medical decision without inducing excessive toxicity, irritation, allergic responses, etc.

As used herein, the term "pharmaceutically acceptable salt" refers to a salt derived from a pharmaceutically acceptable inorganic acid, organic acid, or base. Examples of a suitable acid may include hydrochloric acid, bromic acid, sulfuric acid, nitric acid, perchloric acid, fumaric acid, maleic acid, phosphoric acid, glycolic acid, lactic acid, salicylic acid, succinic acid, toluene-p-sulfonic acid, tartaric acid, acetic acid, citric acid, methanesulfonic acid, formic acid, benzoic acid, malonic acid, naphthalene-2-sulfonic acid, benzenesulfonic acid, etc. Examples of the salt derived from a suitable base may include alkali metals such as sodium, potassium, etc., alkaline earth metals such as magnesium, etc., and ammonium, etc.

In addition, as used herein, the term "solvate" refers to a complex of the peptide according to the present invention or a salt thereof and a solvent molecule.

The composition according to the present invention may include the peptide (trigonal agonist) or the conjugate thereof, specifically a pharmaceutically effective amount of the peptide or conjugate thereof. Further, the composition may further include a pharmaceutically acceptable carrier. The composition of the present invention may have prophylactic or therapeutic use for sequelae following respiratory infectious diseases.

As used herein, the term "prevention" refers to all actions intended to suppress or delay sequelae following respiratory infectious diseases by administering the peptide (e.g., the peptide itself or the long-acting conjugate formed by linking a biocompatible material thereto) or the composition including the same. In the present invention, the prevention of sequelae following respiratory infectious diseases may mean that, independently of the suppression of the source of infection, abnormal body responses (e.g., organ dysfunction or damage, etc.) that may occur in an infected individual after infection are suppressed or delayed in advance, but is not limited thereto.

As used herein, the term "treatment" refers to all actions to alleviate or beneficially change symptoms of sequelae following respiratory infectious diseases by administering the peptide (e.g., the peptide itself or the long-acting conjugate formed by linking a biocompatible material thereto) or the composition including the same. In the present invention, the treatment of sequelae following respiratory infectious diseases may mean that, independently of the suppression of the source of infection, abnormal body responses (e.g., organ dysfunction or damage, etc.) that may occur in an infected individual after infection have taken a turn for the better or been modified favorably, but is not limited thereto.

Specifically, the peptide, long-acting conjugate, or composition including the same according to the present invention may improve excessive inflammation and fibrosis, thereby preventing or treating sequelae following respiratory infectious diseases, but is not limited thereto.

In the present invention, the prevention or treatment of sequelae following respiratory infectious diseases may be performed before and/or after complete recovery from respiratory infectious diseases.

As used herein, the "administration" refers to introduction of a predetermined substance (e.g., the trigonal agonist or the long-acting conjugate thereof) into a patient by way of any appropriate method, and an administration route of the composition may be, but is not particularly limited to, any common route that enables delivery of the composition to the target in living organisms, for example, intraperitoneal administration, intravenous administration, intramuscular administration, subcutaneous administration, intradermal administration, oral administration, topical administration, intranasal administration, intrapulmonary administration, or intrarectal administration.

Use of the trigonal agonist having activities to all of glucagon, GLP-1, and GIP receptors of the present invention or the long-acting conjugate thereof has a great advantage in that it may improve the quality of life of patients by reducing the frequency of administration in chronic patients who need to be administered daily, due to a dramatic increase in the blood half-life and durability of in vivo efficacy.

The pharmaceutical composition of the present invention may further include a pharmaceutically acceptable carrier or diluent. Such a pharmaceutically acceptable carrier or diluent may be non-naturally occurring.

As used herein, the term "pharmaceutically acceptable" refers to an amount sufficient to exhibit therapeutic effects without causing side-effects, and may be easily determined by those of ordinary skill in the art, based on factors well known in the medical field such as the type of disease, a patient's age, body weight, health status, gender, and sensitivity to drug, administration route, administration method, frequency of administration, duration of treatment, and a drug used in combination or concurrently.

The pharmaceutical composition including the peptide of the present invention may include a pharmaceutically acceptable excipient. Although the excipient is not particularly limited, a binder, a lubricant, a disintegrator, a solubilizer, a dispersant, a stabilizer, a suspending agent, a coloring agent, and a flavoring agent may be used for oral administration, a buffer, a preservative, an analgesic, a solubilizer, an isotonic agent, and a stabilizer may be used in combination for injectable preparations, and a base, an excipient, a lubricant, a preservative, etc. may be used for preparation for topical administration.

The composition of the present invention may be formulated into various forms in combination with the above-mentioned pharmaceutically acceptable excipient. For example, for oral administration, the composition may be formulated into tablets, troches, capsules, elixirs, suspensions, syrups, wafers, etc. For injectable preparations, the composition may be formulated into a single-dose ampoule or multidose form. The composition may also be formulated into solutions, suspensions, tablets, pills, capsules, sustained-release preparations, etc.

Meanwhile, examples of the carrier, excipient, and diluent suitable for formulation may include lactose, dextrose, sucrose, sorbitol, mannitol, xylitol, erythritol, maltitol, starch, acacia rubber, alginate, gelatin, calcium phosphate, calcium silicate, cellulose, methyl cellulose, microcrystalline cellulose, polyvinyl pyrrolidone, water, methylhydroxy benzoate, propylhydroxy benzoate, talc, magnesium stearate, or mineral oils. Also, the composition may further include a filler, an anti-coagulant, a lubricant, a humectant, a flavoring agent, a preservative, etc.

In addition, the pharmaceutical composition of the present invention may have any one formulation selected from the group consisting of tablets, pills, powders, granules, capsules, suspensions, formulations for internal use, emulsions, syrups, sterilized aqueous solutions, non-aqueous solvents, lyophilized preparations, and suppositories.

Also, the composition may be formulated in a unit dosage form suitable for administration into a patient's body, specifically in a form useful for administration of protein medicines, according to a method commonly used in the art, and administered via an oral administration route or a parenteral administration route such as an intradermal, intravenous, intramuscular, intraarterial, intramedullary, intrathecal, intraventricular, intrapulmonary, transdermal, subcutaneous, intraperitoneal, intranasal, intestinal, topical, sublingual, vaginal, or rectal route using an administration method commonly used in the art, but is not limited thereto.

In addition, the conjugate may be used in combination with various carriers permitted as medicaments such as a saline solution or an organic solvent. As the medicaments, carbohydrates such as glucose, sucrose, or dextran, antioxidants such as ascorbic acid or glutathione, chelating agents, low-molecular-weight proteins, or other stabilizers may be used to improve stability or absorbability.

Another aspect of the present invention provides a method of preventing or treating sequelae following respiratory infectious diseases, the method including the step of administering, to an individual, the pharmaceutical composition including a pharmaceutically effective amount of the peptide including any one amino acid sequence of SEQ ID NOS: 1 to 102 or the long-acting conjugate thereof.

An administration dose and frequency of the pharmaceutical composition of the present invention may be determined depending on a type of a drug, as an active ingredient, together with various related factors such as a disease to be treated, administration route, a patient's age, gender, and body weight, and severity of the disease. Specifically, the composition of the present invention may include a pharmaceutically effective amount of the trigonal agonist or the long-acting conjugate including the same, but is not limited thereto.

The including of the pharmaceutically effective amount of the peptide or the long-acting conjugate refers to the degree to which the desired pharmacological activity (e.g., prevention, improvement, or treatment of sequelae of respiratory infections) may be obtained due to the trigonal agonist or the long-acting conjugate, and may also refer to a pharmaceutically acceptable level that causes no or an insignificant level of toxicity or side effects in an individual to be administered, but is not limited thereto. Such a pharmaceutically effective amount may be determined in consideration of the frequency of administration, a patient, a formulation, etc.

The long-acting conjugate of the present invention may be administered in an amount of about 0.01 mg, 0.02 mg, 0.03 mg, 0.04 mg, 0.05 mg, mg, 0.07 mg, 0.08 mg, 0.09 mg, 0.10 mg, 0.11 mg, 0.12 mg, 0.13 mg, mg, 0.15 mg, or more per kg, but is not limited thereto.

The pharmaceutical composition of the present invention may include, but is not particularly limited to, 0.01% to 99% weight/volume of the component (active ingredient).

The total effective dose of the composition of the present invention may be administered to a patient in a single dose or may be administered for a long period of time in multiple doses according to a fractionated treatment protocol. In the pharmaceutical composition of the present invention, the content of the active ingredient may vary depending on the disease severity. Specifically, a preferred total daily dose of the peptide or the long-acting conjugate thereof according to the present invention may be about 0.0001 mg to 500 mg per 1 kg of body weight of a patient. However, the effective dose of the peptide or the conjugate thereof is determined considering various factors including a patient's age, body weight, health conditions, gender, disease severity, diet, and excretion rate, in addition to administration route of the pharmaceutical composition and treatment frequency. In this regard, those skilled in the art may easily determine the effective dose suitable for the particular use of the pharmaceutical composition of the present invention. The pharmaceutical composition according to the present invention is not particularly limited to the formulation and administration route and mode, as long as it shows the effects of the present invention.

The pharmaceutical composition of the present invention has excellent in vivo durability and potency, and may significantly reduce the number and frequency of administration of the pharmaceutical preparation of the present invention.

For example, the pharmaceutical composition of the present invention may be administered once a week, once every 2 weeks, once every 4 weeks, or once a month, but is not limited thereto.

Still another aspect to achieve the present invention provides a method of preventing or treating sequelae following respiratory infectious diseases, the method including the step of administering the trigonal agonist (peptide) and/or the long-acting conjugate of the trigonal agonist, or the composition including the same to an individual in need thereof.

The trigonal agonist and/or the long-acting conjugate of the trigonal agonist or the composition including the same, the sequelae following respiratory infectious diseases, the preventing, and the treating are the same as described above.

In the present invention, the individual refers to an individual suspected of having the sequelae following respiratory infectious diseases, and the individual suspected of having the sequelae following respiratory infectious diseases refers to mammals such as humans, rats, livestock, etc. having respiratory infectious disease or having or at risk of having abnormal body conditions even after complete recovery from the respiratory infectious disease, but any individual that may be treated with the trigonal agonist and/or the conjugate or the composition including the same according to the present invention may be included without limitation. In addition, by administering the trigonal agonist and/or the long-acting conjugate thereof according to the present invention or the composition including the same, cytokine secretion and/or expression may be suppressed to suppress excessive immune responses (cytokine storm) and to improve pneumonia and fibrosis. Thus, the individual may be an individual having cytokine storm, sepsis, or organ failure, in particular, an individual having pneumonia and pulmonary fibrosis after respiratory infection, but is not limited thereto.

As used herein, the term "administration" refers to introduction of a predetermined substance into a patient by way of any appropriate method, and an administration route of the composition may be, but is not particularly limited to, any common route that enables delivery of the composition to the target in living organisms, for example, intraperitoneal administration, intravenous administration, intramuscular administration, subcutaneous administration, intradermal administration, oral administration, topical administration, intranasal administration, intrapulmonary administration, or intrarectal administration.

The method of the present invention may include administering a pharmaceutically effective amount of the pharmaceutical composition including the trigonal agonist or the long-acting conjugate thereof. An appropriate total daily dose may be determined by a physician within the scope of correct medical decision, and may be administered once or divided into several doses. However, with respect to the objects of the present invention, it is preferable that a specific therapeutically effective amount for a particular patient will be applied depending on various factors including the type and extent of responses to be achieved, a specific composition, including whether other agents are used in some cases, a patient's age, body weight, general health conditions, sex and diet, administration time, an administration route and an excretion rate of the composition, duration of treatment, a drug used together with or concurrently with the specific composition, and similar factors well known in the medical field.

The pharmaceutical composition of the present invention may be, but is not limited to, administered once a week, once every 2 weeks, once every 4 weeks, or once a month, but is not limited thereto.

Still another aspect to achieve the present invention provides use of the composition including the trigonal agonist or the long-acting conjugate thereof in the preparation of a prophylactic or therapeutic agent for sequelae following respiratory infectious diseases. With respect to the objects of the present invention, the trigonal agonist, the long-acting conjugate thereof, or the composition including the same may have the effect of suppressing cytokine storm, but is not limited thereto.

The trigonal agonist and/or the conjugate thereof, or the composition including the same, the sequelae following respiratory infectious diseases, the preventing, and the treating are the same as described above.

Still another aspect to achieve the present invention provides use of the trigonal agonist or the long-acting conjugate thereof or the composition including the same in the prevention or treatment of the sequelae following respiratory infectious diseases. With respect to the objects of the present invention, the trigonal agonist, the long-acting conjugate thereof, or the composition including the same may have the effect of suppressing cytokine storm, but is not limited thereto.

The trigonal agonist and/or the conjugate thereof, or the composition including the same, the sequelae following respiratory infectious diseases, the preventing, and the treating are the same as described above.

Hereinafter, the present invention will be described in more detail with reference to the following Examples.

However, these Examples are for illustrative purposes only, and the scope of the present invention is not intended to be limited by these Examples.

Example 1: Preparation of Trigonal Agonist

Trigonal agonists exhibiting activities to all of GLP-1, GIP, and glucagon receptors were prepared and sequences thereof are shown in Table 1 below.

TABLE 1

| SEQ ID NO: | Sequence | Information |
|---|---|---|
| 1 | H X Q G T F T S D V S S Y L D G Q A A K E F I A W L V K<br>G C | |
| 2 | H X Q G T F T S D V S S Y L D G Q A Q K E F I A W L V K<br>G C | |
| 3 | H X Q G T F T S D V S S Y L L G Q A A K Q F I A W L V K G<br>G G P S S G A P P P S C | |
| 4 | H X Q G T F T S D V S S Y L L G Q Q Q K E F I A W L V K<br>G C | |
| 5 | H X Q G T F T S D V S S Y L L G Q Q Q K E F I A W L V K<br>G G G P S S G A P P P S C | |
| 6 | H X Q G T F T S D V S S Y L D G Q A A K E F V A W L L K<br>G C | |
| 7 | H X Q G T F T S D V S K Y L D G Q A A K E F V A W L L K<br>G C | |
| 8 | H X Q G T F T S D V S K Y L D G Q A A Q E F V A W L L K<br>G C | |
| 9 | H X Q G T F T S D V S K Y L D G Q A A Q E F V A W L L A<br>G C | |
| 10 | H X Q G T F T S D V S K Y L D G Q A A Q E F V A W L L A<br>G G G P S S G A P P P S C | |
| 11 | C A G E G T F T S D L S K Y L D S R R Q Q L F V Q W L K<br>A G G P S S G A P P P S H G | |
| 12 | C A G E G T F I S D L S K Y M D E Q A V Q L F V E W L M A<br>G G P S S G A P P P S H G | |
| 13 | C A G E G T F I S D Y S I Q L D E I A V Q D F V E W L L A Q<br>K P S S G A P P P S H G | |
| 14 | C A G Q G T F T S D Y S I Q L D E I A V R D F V E W L K N<br>G G P S S G A P P P S H G | |
| 15 | C A G Q G T F T S D L S K Q M D E E A V R L F I E W L K N<br>G G P S S G A P P P S H G | |
| 16 | C A G Q G T F T S D L S K Q M D S E A Q Q L F I E W L K<br>N G G P S S G A P P P S H G | |
| 17 | C A G Q G T F T S D L S K Q M D E E R A R E F I E W L L A<br>Q K P S S G A P P P S H G | |
| 18 | C A G Q G T F T S D L S K Q M D S E R A R E F I E W L K<br>N T G P S S G A P P P S H G | |
| 19 | C A G Q G T F T S D L S I Q Y D S E H Q R D F I E W L K D<br>T G P S S G A P P P S H G | |
| 20 | C A G Q G T F T S D L S I Q Y E E E A Q Q D F V E W L K<br>D T G P S S G A P P P S H G | |
| 21 | Y X Q G T F T S D Y S K Y L D E C R A K E F V Q W L L D<br>H H P S S G Q P P P S | ring formed |
| 22 | Y X Q G T F T S D Y S K C L D E K R A K E F V Q W L L D<br>H H P S S G Q P P P S | ring formed |

TABLE 1-continued

| SEQ ID NO: | Sequence | Information |
|---|---|---|
| 23 | Y X Q G T F T S D Y S K Y L D E C R A K E F V Q W L L A Q K G K K N D W K H N I T | ring formed |
| 24 | Y X Q G T F T S D Y S K Y L D E C R A K E F V Q W L K N G G P S S G A P P P S | ring formed |
| 25 | H X Q G T F T S D C S K Y L D E R A A Q D F V Q W L L D G G P S S G A P P P S | |
| 26 | H X Q G T F T S D C S K Y L D S R A A Q D F V Q W L L D G G P S S G A P P P S | |
| 27 | H X Q G T F T S D Y S K Y L D E R A C Q D F V Q W L L D Q G G P S S G A P P P S | |
| 28 | H X Q G T F T S D Y S K Y L D E K R A Q E F V C W L L A Q K G K K N D W K H N I T | |
| 29 | H X Q G T F T S D Y S K Y L D E K A A K E F V Q W L L N T C | ring formed |
| 30 | H X Q G T F T S D Y S K Y L D E K A Q K E F V Q W L L D T C | ring formed |
| 31 | H X Q G T F T S D Y S K Y L D E K A C K E F V Q W L L A Q | ring formed |
| 32 | H X Q G T F T S D Y S K Y L D E K A C K D F V Q W L L D G G P S S G A P P P S | ring formed |
| 33 | H X Q G T F T S D Y S I A M D E I H Q K D F V N W L L A Q K C | ring formed |
| 34 | H X Q G T F T S D Y S K Y L D E K R Q K E F V N W L L A Q K C | ring formed |
| 35 | H X Q G T F T S D Y S I A M D E I H Q K D F V N W L L N T K C | ring formed |
| 36 | H X Q G T F T S D Y S K Y L C E K R Q K E F V Q W L L N G G P S S G A P P P S G | ring formed |
| 37 | H X Q G T F T S D Y S K Y L D E C R Q K E F V Q W L L N G G P S S G A P P P S G | ring formed |
| 38 | C A X Q G T F T S D K S S Y L D E R A A Q D F V Q W L L D G G P S S G A P P P S S | |
| 39 | H X Q G T F T S D Y S K Y L D G Q H A Q C F V A W L L A G G G P S S G A P P P S | |
| 40 | H X Q G T F T S D K S K Y L D E R A C Q D F V Q W L L D G G P S S G A P P P S | |
| 41 | H X Q G T F T S D K S K Y L D E C A A Q D F V Q W L L D G G P S S G A P P P S | |
| 42 | Y X Q G T F T S D Y S K Y L D E K R A K E F V Q W L L D H H P S S G Q P P P S C | ring formed |
| 43 | Y X Q G T F T S D Y S K Y L D E K R A K E F V Q W L L D H H C S S G Q P P P S | ring formed |
| 44 | H G Q G T F T S D C S K Q L D G Q A A Q E F V A W L L A G G P S S G A P P P S | |
| 45 | H G Q G T F T S D C S K Y M D G Q A A Q D F V A W L L A G G P S S G A P P P S | |
| 46 | H G Q G T F T S D C S K Y L D E Q H A Q E F V A W L L A G G P S S G A P P P S | |
| 47 | H G Q G T F T S D C S K Y L D G Q R A Q E F V A W L L A G G P S S G A P P P S | |

TABLE 1-continued

| SEQ ID NO: | Sequence | Information |
|---|---|---|
| 48 | H G Q G T F T S D C S K Y L D G Q R A Q D F V N W L L A G G P S S G A P P P S | |
| 49 | C A X Q G T F T S D Y S I C M D E I H Q K D F V N W L L N T K | ring formed |
| 50 | H X Q G T F T S D Y S K Y L D E K R A K E F V Q W L L D H H P S S G Q P P P S C | ring formed |
| 51 | H X Q G T F T S D Y S K Y L D E K R Q K E F V Q W L L N T C | ring formed |
| 52 | H X Q G T F T S D Y S K Y L D E K R Q K E F V Q W L L D T C | ring formed |
| 53 | H X E G T F T S D Y S I A M D E I H Q K D F V N W L L A Q C | ring formed |
| 54 | H X E G T F T S D Y S I A M D E I H Q K D F V D W L L A E C | ring formed |
| 55 | H X Q G T F T S D Y S I A M D E I H Q K D F V N W L L A Q C | ring formed |
| 56 | H X Q G T F T S D Y S K Y L D E K R Q K E F V N W L L A Q C | ring formed |
| 57 | H X Q G T F T S D Y S I A M D E I H Q K D F V N W L L N T C | ring formed |
| 58 | H X Q G T F T S D Y S K Y L D E K R Q K E F V Q W L L N T K C | ring formed |
| 59 | C A X Q G T F T S D Y S I C M D E K H Q K D F V N W L L N T K | ring formed |
| 60 | C A X Q G T F T S D Y S I A M D E K H C K D F V N W L L N T K | ring formed |
| 61 | C A X Q G T F T S D Y S I A M D E I A C K D F V N W L L N T K | ring formed |
| 62 | C A X Q G T F T S D K S K Y L D E R A A Q D F V Q W L L D G G P S S G A P P P S | — |
| 63 | C A X Q G T F T S D C S K Y L D E R A A Q D F V Q W L L D G G P S S G A P P P S | — |
| 64 | Y X Q G T F T S D Y S K Y L D E C A A K E F V Q W L L D H H P S S G Q P P P S | ring formed |
| 65 | H X Q G T F T S D Y S K C L D E K R A K E F V Q W L L D H H P S S G Q P P P S | ring formed |
| 66 | Y X Q G T F T S D Y S K Y L D E C R A K D F V Q W L L D H H P S S G Q P P P S | ring formed |
| 67 | Y X Q G T F T S D Y S K Y L D E C A A K D F V Q W L L D H H P S S G Q P P P S | ring formed |
| 68 | Y X Q G T F T S D Y S K C L D E K A A K E F V Q W L L D H H P S S G Q P P P S | ring formed |
| 69 | Y X Q G T F T S D Y S K C L D E R A A K E F V Q W L L D H H P S S G Q P P P S | ring formed |
| 70 | Y X Q G T F T S D Y S K C L D E K R A K D F V Q W L L D H H P S S G Q P P P S | ring formed |
| 71 | Y X Q G T F T S D Y S K Y L D E R A C K D F V Q W L L D H H P S S G Q P P P S | ring formed |
| 72 | Y X Q G T F T S D C S K Y L D E R A A K D F V Q W L L D H H P S S G Q P P P S | ring formed |
| 73 | C A X Q G T F T S D Y S K Y L D E C R A K E F V Q W L L D H H P S S G Q P P P S | ring formed |

TABLE 1-continued

| SEQ ID NO: | Sequence | Information |
|---|---|---|
| 74 | C A X Q G T F T S D Y S K C L D E K R A K E F V Q W L L D H H P S S G Q P P P S | ring formed |
| 75 | Y X Q G T F T S D Y S K Y L D E K A A K E F V Q W L L D H H P S S G Q P P P S C | ring formed |
| 76 | Y X Q G T F T S D Y S K Y L D E K R A K D F V Q W L L D H H P S S G Q P P P S C | ring formed |
| 77 | Y X Q G T F T S D Y S K Y L D E K A A K D F V Q W L L D H H P S S G Q P P P S C | ring formed |
| 78 | H X Q G T F T S D Y S K Y L D E K R Q K E F V Q W L L D T K C | ring formed |
| 79 | H X E G T F T S D Y S I A M D E I H Q K D F V N W L L A Q K C | ring formed |
| 80 | H X E G T F T S D Y S I A M D E I H Q K D F V D W L L A E K C | ring formed |
| 81 | C A X Q G T F T S D Y S K Y L D E K R Q K E F V Q W L L N T C | ring formed |
| 82 | C A X Q G T F T S D Y S K Y L D E K R Q K E F V Q W L L D T C | ring formed |
| 83 | C A X E G T F T S D Y S I A M D E I H Q K D F V N W L L A Q C | ring formed |
| 84 | C A X E G T F T S D Y S I A M D E I H Q K D F V D W L L A E C | ring formed |
| 85 | C A X Q G T F T S D Y S I A M D E I H Q K D F V N W L L A Q C | ring formed |
| 86 | C A X Q G T F T S D Y S K Y L D E K R Q K E F V N W L L A Q C | ring formed |
| 87 | C A X Q G T F T S D Y S I A M D E I H Q K D F V N W L L N T C | ring formed |
| 88 | C A X Q G T F T S D Y S K Y L D E K R Q K E F V Q W L L N T K C | ring formed |
| 89 | C A X Q G T F T S D Y S K Y L D E K R Q K E F V Q W L L D T K C | ring formed |
| 90 | C A X E G T F T S D Y S I A M D E I H Q K D F V N W L L A Q K C | ring formed |
| 91 | C A X E G T F T S D Y S I A M D E I H Q K D F V D W L L A E K C | ring formed |
| 92 | C A X Q G T F T S D Y S I A M D E I H Q K D F V N W L L A Q K C | ring formed |
| 93 | C A X Q G T F T S D Y S K Y L D E K R Q K E F V N W L L A Q K C | ring formed |
| 94 | C A X Q G T F T S D Y S I A M D E I H Q K D F V N W L L N T K C | ring formed |
| 95 | Y X Q G T F T S D Y S K Y L D E K R A K E F V Q W L L C H H P S S G Q P P P S | ring formed |
| 96 | Y X Q G T F T S D Y S K Y L D E K R A K E F V Q W L L D H C P S S G Q P P P S | ring formed |
| 97 | Y X Q G T F T S D Y S K Y L D E K R A K E F V Q W L L D C H P S S G Q P P P S | ring formed |
| 98 | Y X Q G T F T S D Y S K A L D E K A A K E F V N W L L D H H P S S G Q P P P S C | ring formed |

TABLE 1-continued

| SEQ ID NO: | Sequence | Information |
|---|---|---|
| 99 | Y X Q G T F T S D Y S K A L D E K A A K D F V N W L L D H H P S S G Q P P P S C | ring formed |
| 100 | Y X Q G T F T S D Y S K A L D E K A A K E F V Q W L L D Q H P S S G Q P P P S C | ring formed |
| 101 | Y X Q G T F T S D Y S K A L D E K A A K E F V N W L L D Q H P S S G Q P P P S C | ring formed |
| 102 | Y X Q G T F T S D Y S K A L D E K A A K D F V N W L L D Q H P S S G Q P P P S C | ring formed |

In the sequences described in Table 1, the amino acid indicated by X represents a non-native amino acid Aib (2-aminoisobutyric acid), and the underline means that the underlined amino acids form a ring with each other. In Table 1, CA represents 4-imidazoacetyl. The trigonal agonist peptide is used as a C-terminal amidated trigonal agonist, as needed.

Example 2: Preparation of Long-Acting Conjugate of Trigonal Agonist

For pegylation of 10 kDa PEG having a maleimide group and an aldehyde group at both ends respectively, i.e., maleimide-PEG-aldehyde (10 kDa, NOF, Japan) into a cysteine residue of each trigonal agonist (SEQ ID NO: 21, 22, 42, 43, 50, 77, and 96) of Example 1, each trigonal agonist and the maleimide-PEG-aldehyde were reacted at a molar ratio of 1:1 to 3 with a protein concentration of 1 mg/mL to 5 mg/mL at low temperature for 0.5 to 3 hours. In this case, the reaction was conducted in an environment including 50 mM Tris buffer (pH 7.5) to which 20% to 60% isopropanol was added. Upon completion of the reaction, the reaction solution was applied to SP sepharose HP (GE Healthcare, USA) to purify each trigonal agonist which was mono-pegylated on cysteine.

Next, the reaction was carried out at 4° C. to 8° C. for 12 to 18 hours, with a molar ratio of the purified mono-PEGylated trigonal agonist at 1:1 to 5 and an immunoglobulin Fc (homodimer of SEQ ID NO: 123) and the protein concentration of 10 mg/mL to 50 mg/mL. The reaction was conducted in an environment including 10 mM to 50 mM sodium cyanoborohydride, which was added as a reducing agent to a 100 mM potassium phosphate buffer (pH 6.0), and 10% to 30% isopropanol. Upon completion of the reaction, each conjugate including the trigonal agonist and the immunoglobulin Fc was purified from the reaction solution by applying to a butyl sepharose FF purification column (GE Healthcare, USA) and a Source ISO purification column (GE Healthcare, USA). This purified long-acting conjugate had a structure in which the trigonal agonist peptide, polyethylene glycol (PEG) linker, and Fc dimer were covalently linked to each other at a molar ratio of 1:1:1 in the molecule, wherein the PEG linker was linked to only one chain of the two polypeptide chains of the Fc dimer.

Meanwhile, with regard to the immunoglobulin Fc, two monomers, each having an amino acid sequence of SEQ ID NO: 123 (consisting of 221 amino acids), formed a homodimer via disulfide bonds between cysteine amino acids at position 3 of each monomer, wherein the monomers of the homodimer each independently formed intra-disulfide bonds between cysteines at positions 35 and 95, and intra-disulfide bonds between cysteines at positions 141 and 199.

After preparation, purity was 95% or more, as analyzed by reverse-phase chromatography, size-exclusion chromatography, and ion-exchange chromatography.

Here, a conjugate prepared by linking a trigonal agonist, prepared by C-terminal amidation of a trigonal agonist of SEQ ID NO: 21, with an immunoglobulin Fc via a PEG linker, was named a "conjugate including SEQ ID NO: 21 and immunoglobulin Fc" or a "long-acting conjugate of SEQ ID NO: 21", and they may be used interchangeably.

Here, a conjugate prepared by linking a trigonal agonist, prepared by C-terminal amidation of a trigonal agonist of SEQ ID NO: 22, with an immunoglobulin Fc via a PEG linker, was named a "conjugate including SEQ ID NO: 22 and immunoglobulin Fc" or a "long-acting conjugate of SEQ ID NO: 22", and they may be used interchangeably.

Here, a conjugate prepared by linking a trigonal agonist, prepared by C-terminal amidation of a trigonal agonist of SEQ ID NO: 42, with an immunoglobulin Fc via a PEG, was named a "conjugate including SEQ ID NO: 42 and immunoglobulin Fc" or a "long-acting conjugate of SEQ ID NO: 42", and they may be used interchangeably.

Here, a conjugate prepared by linking a trigonal agonist, prepared by C-terminal amidation of a trigonal agonist of SEQ ID NO: 43, with an immunoglobulin Fc via a PEG, was named a "conjugate including SEQ ID NO: 43 and immunoglobulin Fc" or a "long-acting conjugate of SEQ ID NO: 43", and they may be used interchangeably.

Here, a conjugate prepared by linking a trigonal agonist, prepared by C-terminal amidation of a trigonal agonist of SEQ ID NO: 50, with an immunoglobulin Fc via a PEG, was named a "conjugate including SEQ ID NO: 50 and immunoglobulin Fc" or a "long-acting conjugate of SEQ ID NO: 50", and they may be used interchangeably.

Here, a conjugate prepared by linking a trigonal agonist, prepared by C-terminal amidation of a trigonal agonist of SEQ ID NO: 77, with an immunoglobulin Fc via a PEG, was named a "conjugate including SEQ ID NO: 77 and immunoglobulin Fc" or a "long-acting conjugate of SEQ ID NO: 77", and they may be used interchangeably.

Here, a conjugate prepared by linking a trigonal agonist, prepared by C-terminal amidation of a trigonal agonist of SEQ ID NO: 96, with an immunoglobulin Fc via a PEG, was named a "conjugate including SEQ ID NO: 96 and immunoglobulin Fc" or a "long-acting conjugate of SEQ ID NO: 96", and they may be used interchangeably.

Experimental Example 1: Measurement of In Vitro Activity of Trigonal Agonist and Long-Acting Conjugate Thereof To measure activities of the trigonal agonists and the long-acting conjugates thereof prepared in Examples 1 and 2, cell lines each transformed with GLP-1 receptor, glucagon (GCG) receptor, and GIP receptor were used to measure cell activity in vitro.

The cell lines are those prepared by transforming CHO (Chinese hamster ovary) to express human GLP-1 receptor, human GCG receptor, and human GIP receptor genes, respectively, and they are suitable for measuring activities of GLP-1, GCG, and GIP. Therefore, each activity was measured using the transformed cell lines, respectively.

To measure GLP-1 activity of the trigonal agonists and the long-acting conjugates thereof prepared in Examples 1 and 2, human GLP-1 was subjected to a 4-fold serial dilution from 50 nM to 0.000048 nM, and the trigonal agonists and the long-acting conjugates thereof prepared in Examples 1 and 2 were subjected to a 4-fold serial dilution from 400 nM to 0.00038 nM. The culture solution was removed from the cultured CHO cells, in which the human GLP-1 receptor was expressed, and then each serially diluted material was added to the cells in an amount of 5 μL, respectively. Thereafter, 5 μL of a buffer containing a cAMP antibody was added, followed by incubation at room temperature for 15 minutes. Then, 10 μL of a detection mix containing a cell lysis buffer was added thereto to lyse the cells, and this was allowed to react at room temperature for 90 minutes. The cell lysates, in which the reaction was completed, were applied to a LANCE cAMP kit (PerkinElmer, USA) to calculate the $EC_{50}$ value via accumulated cAMP, and the values were compared with one another. The relative titers compared to human GLP-1 are shown in Tables 2 and 3 below.

To measure GCG activity of the trigonal agonists and the long-acting conjugates thereof prepared in Examples 1 and 2, human GCG was subjected to a 4-fold serial dilution from 50 nM to 0.000048 nM, and the trigonal agonists and the long-acting conjugates thereof prepared in Examples 1 and 2 were subjected to a 4-fold serial dilution from 400 nM to 0.00038 nM. The culture solution was removed from the cultured CHO cells, in which the human GCG receptor was expressed, and then each serially diluted material was added to the cells in an amount of 5 μL, respectively. Thereafter, 5 μL of a buffer containing a cAMP antibody was added, followed by incubation at room temperature for 15 minutes. Then, 10 μL of a detection mix containing a cell lysis buffer was added thereto to lyse the cells, and this was allowed to react at room temperature for 90 minutes. The cell lysates, in which the reaction was completed, were applied to a LANCE cAMP kit (PerkinElmer, USA) to calculate the $EC_{50}$ value via accumulated cAMP, and the values were compared with one another. The relative titers compared to human GCG are shown in Tables 2 and 3 below.

To measure GIP activity of the trigonal agonists and the long-acting conjugates thereof prepared in Examples 1 and 2, human GIP was subjected to a 4-fold serial dilution from 50 nM to 0.000048 nM, and the trigonal agonists and the long-acting conjugates thereof prepared in Examples 1 and 2 were subjected to a 4-fold serial dilution from 400 nM to 0.00038 nM. The culture solution was removed from the cultured CHO cells, in which the human GIP receptor was expressed, and then each serially diluted material was added to the cells in an amount of 5 μL, respectively. Thereafter, 5 μL of a buffer containing a cAMP antibody was added, followed by incubation at room temperature for 15 minutes. Then, 10 μL of a detection mix containing a cell lysis buffer was added thereto to lyse the cells, and this was allowed to react at room temperature for 90 minutes. The cell lysates, in which the reaction was completed, were applied to a LANCE cAMP kit (PerkinElmer, USA) to calculate the $EC_{50}$ value via accumulated cAMP, and the values were compared with one another. The relative titers compared to human GIP are shown in Tables 2 and 3 below.

TABLE 2

| Relative titer ratio of trigonal agonist | | | |
|---|---|---|---|
| | In vitro activity relative to native peptide (%) | | |
| SEQ ID NO: | vs. GLP-1 | vs. Glucagon | vs. GIP |
| 1 | 3.2 | <0.1 | <0.1 |
| 2 | 5.9 | <0.1 | <0.1 |
| 3 | 1.8 | <0.1 | <0.1 |
| 4 | 8.5 | <0.1 | <0.1 |
| 5 | 42.1 | <0.1 | <0.1 |
| 6 | 17.0 | <0.1 | <0.1 |
| 7 | 13.7 | <0.1 | <0.1 |
| 8 | 14.2 | 0.10 | <0.1 |
| 9 | 32.1 | 0.13 | <0.1 |
| 10 | 46.0 | <0.1 | <0.1 |
| 11 | 1.4 | <0.1 | <0.1 |
| 12 | 0.4 | <0.1 | <0.1 |
| 13 | <0.1 | <0.1 | <0.1 |
| 14 | 28.0 | <0.1 | <0.1 |
| 15 | 79.2 | <0.1 | <0.1 |
| 16 | 2.1 | <0.1 | <0.1 |
| 17 | 0.2 | <0.1 | <0.1 |
| 18 | <0.1 | <0.1 | <0.1 |
| 19 | <0.1 | <0.1 | <0.1 |
| 20 | <0.1 | <0.1 | <0.1 |
| 21 | 17.8 | 267 | 22.7 |
| 22 | 20.1 | 140 | 59.7 |
| 23 | 4.01 | 9.3 | <0.1 |
| 24 | 41.2 | 9.3 | <0.1 |
| 25 | 82.6 | 0.1 | <0.1 |
| 26 | 64.5 | 0.2 | <0.1 |
| 27 | 83.1 | 0.8 | 0.9 |
| 28 | 17.2 | 1.6 | <0.1 |
| 29 | 38.5 | 6.0 | <0.1 |
| 30 | 142 | 0.7 | 0.8 |
| 31 | 135 | 2.2 | 2.4 |
| 32 | 151 | 1.7 | 8.8 |
| 33 | 24.5 | <0.1 | 10.4 |
| 34 | 19.1 | 0.92 | 0.6 |
| 35 | 7.5 | <0.1 | 1.3 |
| 36 | 37.4 | 0.39 | 0.2 |
| 37 | 236 | 6.21 | 2.2 |
| 38 | 2.3 | — | — |
| 39 | 13.9 | 0.53 | <0.1 |
| 40 | 75.2 | <0.1 | <0.1 |
| 41 | 34.3 | <0.1 | <0.1 |
| 42 | 33.9 | 205.8 | 7.8 |
| 43 | 12.6 | 88.4 | 3.70 |
| 44 | 1.3 | <0.1 | <0.1 |
| 45 | 6.6 | <0.1 | <0.1 |
| 46 | 1.4 | <0.1 | <0.1 |
| 47 | 2.4 | <0.1 | <0.1 |
| 48 | 1.5 | <0.1 | <0.1 |
| 49 | 29.8 | <0.1 | 3.3 |
| 50 | 67.4 | 50.5 | 2.7 |
| 51 | 14.4 | 2.0 | 0.1 |
| 52 | 44.1 | 7.5 | 0.3 |
| 53 | 161 | 8.4 | 1.3 |
| 54 | 30.6 | 1.4 | 0.1 |
| 55 | 27.1 | 0.7 | 2.4 |
| 56 | 57.9 | 4.9 | 0.8 |
| 57 | 11.7 | <0.1 | 0.3 |
| 58 | 39.1 | 2.6 | 0.2 |
| 59 | 40.3 | <0.1 | 4.0 |
| 60 | 106.2 | <0.1 | 8.2 |
| 61 | 59.8 | <0.1 | 2.8 |
| 62 | 5.2 | <0.1 | <0.1 |
| 63 | 15.3 | <0.1 | <0.1 |

TABLE 2-continued

| Relative titer ratio of trigonal agonist | | | |
|---|---|---|---|
| | In vitro activity relative to native peptide (%) | | |
| SEQ ID NO: | vs. GLP-1 | vs. Glucagon | vs. GIP |
| 64 | 64.6 | 60.1 | 92.9 |
| 65 | 95.4 | 25.2 | 11.6 |
| 66 | 15.8 | 172 | 17.2 |
| 67 | 28.5 | 46.2 | 39.8 |
| 68 | 27.9 | 8.8 | 107 |
| 69 | 24.3 | 9.6 | 62.8 |
| 70 | 15.1 | 71.3 | 64.4 |
| 71 | 90.1 | 12.7 | 94.7 |
| 72 | 11.5 | 1.0 | 1.6 |
| 73 | 22.6 | 5.4 | 3.0 |
| 74 | 12.9 | 0.9 | 1.0 |
| 75 | 35.1 | 8.5 | 18.0 |
| 76 | 10.3 | 47.6 | 11.7 |
| 77 | 38.7 | 12.2 | 35.5 |
| 78 | 51.0 | 14.0 | 0.12 |
| 79 | 41.5 | 4.9 | 1.4 |
| 80 | 8.1 | 0.0 | 0.1 |
| 81 | 7.8 | 0.3 | <0.1 |
| 82 | 9.5 | 1.1 | <0.1 |
| 83 | 47.3 | 1.3 | 0.4 |
| 84 | 4.2 | <0.1 | <0.1 |
| 85 | 4.3 | <0.1 | 0.3 |
| 86 | 28.4 | 0.4 | 0.2 |
| 87 | 0.9 | <0.1 | <0.1 |
| 88 | 9.6 | 0.3 | <0.1 |
| 89 | 7.1 | 0.7 | <0.1 |
| 90 | 7.4 | <0.1 | <0.1 |
| 91 | 31.9 | 16.8 | 0.3 |
| 92 | 0.8 | <0.1 | 0.4 |
| 93 | 5.7 | 0.3 | 0.7 |
| 94 | 0.5 | <0.1 | <0.1 |
| 95 | 2.1 | 0.4 | <0.1 |
| 96 | 34.4 | 194.8 | 5.2 |
| 97 | 10.5 | 62.8 | 2.6 |
| 98 | 28.1 | 8.2 | 47.1 |
| 99 | 20.9 | 14.9 | 57.7 |
| 100 | 42.2 | 12.7 | 118.5 |
| 101 | 23.2 | 13.9 | 40.1 |
| 102 | 23.3 | 29.5 | 58.0 |

TABLE 3

| Relative titer ratio of trigonal agonist long-acting conjugate | | | |
|---|---|---|---|
| Long-acting | In vitro activity relative to native peptide (%) | | |
| conjugate | vs. GLP-1 | vs. Glucagon | vs. GIP |
| 21 | 0.1 | 1.6 | 0.2 |
| 22 | 0.1 | 0.9 | 0.5 |
| 42 | 3.1 | 23.1 | 1.2 |
| 43 | 2.1 | 13.5 | 0.6 |
| 50 | 15.4 | 6.9 | 0.7 |
| 77 | 6.7 | 1.7 | 6.6 |
| 96 | 0.3 | 4.0 | 0.3 |

The novel trigonal agonist long-acting conjugates prepared as described above have a trigonal agonist function capable of activating all of the GLP-1 receptor, GIP receptor, and glucagon receptor, and thus may be used as materials of therapeutic agents for sequelae following respiratory infectious diseases.

Experimental Example 2: Effect of Improving Acute Pulmonary Inflammation Due to Cytokine Storm Induced by SARS-CoV-2 Infection To examine the efficacy of the long-acting conjugate of SEQ ID NO: 42 prepared in the above Example on the improvement of lung inflammation caused by SARS-CoV-2 infection, a hamster model (SYRIAN HAMSTER, RjHAN: aura, Central Lab Animal) was used, in which acute lung inflammation was induced by SARS-CoV-2 infection.

First, the sub-cultured SARS-CoV-2 was prepared at $10^3$ $TCID_{50}$/mL (PBS), and 120 μL of the corresponding viral solution was instilled into the hamster nasal cavity to induce viral infection by inhalation. The SARS-CoV-2-infected hamster models were divided into an excipient control, and a group treated with the long-acting conjugate of SEQ ID NO: 42, and repeated administration was carried out every 2 days.

In a first test, a lung tissue of each hamster was taken by autopsy after repeated administration twice, and expression levels of IL-1β, TNF-α, and IFN-γ, which are pro-inflammatory cytokines, were evaluated through quantitative PCR.

As a result, it was confirmed that when the long-acting conjugate of SEQ ID NO: 42 was administered, expression of the pro-inflammatory cytokines in the lung tissue was reduced, as compared to the excipient control group (FIG. 1A, ††p<0.01 vs. SARS-CoV-2, vehicle by unpaired t-test).

In a second test, the excipient or the long-acting conjugate of SEQ ID NO: 42 was repeatedly administered to the SARS-CoV-2-infected hamster models four times, and lung tissues were taken, and the degree of inflammation of the tissues was evaluated through H&E staining. As a negative control, a SARS-CoV-2 infected group not administered with the long-acting conjugate of SEQ ID NO: 42 was used.

As a result, similar to the results of FIG. 1A, it was confirmed that when the long-acting conjugate of SEQ ID NO: 42 was administered, a significant reduction in the lung inflammation score was observed, as compared to the excipient control group (FIG. 1B, †††<0.001 vs. SARS-CoV-2, vehicle by unpaired t-test).

These results suggest that the long-acting conjugate of SEQ ID NO: 42 may lower the levels of cytokines involved in the inflammatory responses in the body, thereby improving inflammation, indicating that the long-acting conjugate according to the present invention may suppress the cytokine storm and may suppress excessive immune responses, thereby effectively improving and controlling acute lung inflammation known as COVID-19 sequelae.

Experimental Example 3: Effect of Improving Pulmonary Fibrosis Due to Cytokine Storm Induction An experiment was conducted to examine efficacy of the long-acting conjugate of SEQ ID NO: 42 on the improvement of pulmonary fibrosis using LPS (lipopolysaccharide) hamster models, in which pulmonary fibrosis was induced through excessive acute pulmonary inflammation.

First, 100 μg to 200 μg of LPS was injected into hamsters by intratracheal→intraperitoneal→intratracheal injection over Day 0→Day 1→Day 3. The LPS-injected hamsters were divided into an excipient control group and a group administered with the long-acting conjugate of SEQ ID NO: 42, and repeated administration was carried out at 2-day intervals. On day 11 after repeated administration six times, the lung tissue of each hamster was taken by autopsy, and the degree of tissue fibrosis was evaluated through Masson-trichrome (MT) staining. As a negative control group, an LPS-injected group not administered with the long-acting conjugate of SEQ ID NO: 42 was used. As a result, it was confirmed that when the long-acting conjugate of SEQ ID NO: 42 was administered, the fibrotic area in the lung tissue was significantly reduced, as compared to the excipient control group (FIG. 2, †~††p<0.05~0.01 vs. LPS, vehicle by unpaired t-test).

This result confirmed that the long-acting conjugate of SEQ ID NO: 42 may suppress pulmonary fibrosis.

Taking together the experimental results of the Examples, it was confirmed that the long-acting conjugate according to the present invention, represented by the long-acting conjugate of SEQ ID NO: 42, is able to improve the excessive lung inflammatory responses caused by SARS-CoV-2 infection, thereby effectively improving even pulmonary fibrosis, which is a representative sequela of COVID-19.

Based on the above description, it will be understood by those skilled in the art that the present disclosure may be implemented in a different specific form without changing the technical spirit or essential characteristics thereof. In this regard, it should be understood that the above embodiment is not limitative, but illustrative in all aspects. The scope of the disclosure is defined by the appended claims rather than by the description preceding them, and therefore all changes and modifications that fall within metes and bounds of the claims, or equivalents of such metes and bounds are therefore intended to be embraced by the claims.

The invention claimed is:

1. A method for treating sequelae following a respiratory infectious disease, comprising administering a pharmaceutical composition to a patient in need thereof, the pharmaceutical composition comprising a pharmaceutically acceptable excipient and a pharmaceutically effective amount of a peptide including any one amino acid sequence of SEQ ID NOS: 1 to 102.

2. The method of claim 1, wherein the peptide is in the form of a long-acting conjugate, and the long-acting conjugate is represented by the following Chemical Formula 1:

X-L-F [Chemical Formula 1]

wherein X is a peptide of any one amino acid sequence of SEQ ID NOS: 1 to 102;

L is a linker including ethylene glycol repeating units,

F is an immunoglobulin Fc region, and

- represents a covalent linkage between X and L, and between L and F.

3. The method of claim 1, wherein the respiratory infectious disease is an infectious disease caused by respiratory virus.

4. The method of claim 3, wherein the respiratory virus is any one selected from the group consisting of adenovirus, vaccinia virus, herpes simplex virus, parainfluenza virus, rhinovirus, varicella zoster virus, measle virus, respiratory syncytial virus, Dengue virus, human immunodeficiency virus (HIV), influenza virus, coronavirus, severe acute respiratory syndrome associated virus (SARS-associated virus), and Middle East respiratory syndrome coronavirus (MERS-CoV).

5. The method of claim 3, wherein the respiratory virus is SARS-CoV-2.

6. The method of claim 3, wherein the respiratory virus is a variant respiratory virus.

7. The method of claim 6, wherein the variant respiratory virus causes sequelae the same as those caused by the respiratory virus.

8. The method of claim 6, wherein the variant respiratory virus is any one selected from the group consisting of SARS-CoV-2 alpha variant (B.1.1.7 lineage), SARS-CoV-2 beta variant (B.1.351 lineage), SARS-CoV-2 gamma variant (P.1 lineage), and SARS-CoV-2 delta variant (B.1.617.2 lineage).

9. The method of claim 1, wherein the sequelae following a respiratory infectious disease is any one or more selected from the group consisting of fever, dyspnea, cough, pneumonia, pulmonary fibrosis, pain, myalgia, fatigue, inflammation, and nervous system disorders.

10. The method of claim 9, wherein the sequelae following respiratory infectious disease is caused by tissue damage due to excessive cytokine secretion.

11. The method of claim 1, wherein the sequelae following respiratory infectious disease is post-COVID-19 pulmonary fibrosis.

12. The method of claim 1, wherein the administering of the pharmaceutical composition exhibits one or more of the followings:

(i) a reduction in the lung inflammation score;

(ii) a reduction in the expression or secretion of a pro-inflammatory cytokine cytokines;

(iii) a reduction in the pulmonary fibrotic area; and (iv) suppressed production of inflammasome complexes.

13. The method of claim 12, wherein the pro-inflammatory cytokine is any one or more selected from the group consisting of interleukin, tumor necrosis factor, and interferon.

14. The method of claim 12, wherein the pro-inflammatory cytokine is IL-1β, TNF-α, or IFN-γ.

15. The method of claim 1, wherein the pharmaceutical composition is administered to an individual having cytokine storm syndrome, sepsis, or organ failure due to respiratory viral infection.

16. The method of claim 1, wherein the peptide includes an amino acid sequence selected from the group consisting of SEQ ID NOS: 21, 22, 42, 43, 50, 77, and 96.

* * * * *

```
SEQUENCE LISTING

<160> NUMBER OF SEQ ID NOS: 124

<210> SEQ ID NO 1
<211> LENGTH: 30
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (2)
<223> OTHER INFORMATION: Xaa is 2-aminoisobutyric acid (Aib)

<400> SEQUENCE: 1

His Xaa Gln Gly Thr Phe Thr Ser Asp Val Ser Ser Tyr Leu Asp Gly
1               5                   10                  15

Gln Ala Ala Lys Glu Phe Ile Ala Trp Leu Val Lys Gly Cys
            20                  25                  30


<210> SEQ ID NO 2
<211> LENGTH: 30
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (2)
<223> OTHER INFORMATION: Xaa is 2-aminoisobutyric acid (Aib)

<400> SEQUENCE: 2

His Xaa Gln Gly Thr Phe Thr Ser Asp Val Ser Ser Tyr Leu Asp Gly
1               5                   10                  15

Gln Ala Gln Lys Glu Phe Ile Ala Trp Leu Val Lys Gly Cys
            20                  25                  30


<210> SEQ ID NO 3
<211> LENGTH: 41
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (2)
<223> OTHER INFORMATION: Xaa is 2-aminoisobutyric acid (Aib)

<400> SEQUENCE: 3

His Xaa Gln Gly Thr Phe Thr Ser Asp Val Ser Ser Tyr Leu Leu Gly
1               5                   10                  15

Gln Ala Ala Lys Gln Phe Ile Ala Trp Leu Val Lys Gly Gly Gly Pro
            20                  25                  30
```

```
Ser Ser Gly Ala Pro Pro Pro Ser Cys
        35                  40


<210> SEQ ID NO 4
<211> LENGTH: 30
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (2)
<223> OTHER INFORMATION: Xaa is 2-aminoisobutyric acid (Aib)

<400> SEQUENCE: 4

His Xaa Gln Gly Thr Phe Thr Ser Asp Val Ser Ser Tyr Leu Leu Gly
1               5                   10                  15

Gln Gln Gln Lys Glu Phe Ile Ala Trp Leu Val Lys Gly Cys
            20                  25                  30


<210> SEQ ID NO 5
<211> LENGTH: 41
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (2)
<223> OTHER INFORMATION: Xaa is 2-aminoisobutyric acid (Aib)

<400> SEQUENCE: 5

His Xaa Gln Gly Thr Phe Thr Ser Asp Val Ser Ser Tyr Leu Leu Gly
1               5                   10                  15

Gln Gln Gln Lys Glu Phe Ile Ala Trp Leu Val Lys Gly Gly Gly Pro
            20                  25                  30

Ser Ser Gly Ala Pro Pro Pro Ser Cys
        35                  40


<210> SEQ ID NO 6
<211> LENGTH: 30
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (2)
<223> OTHER INFORMATION: Xaa is 2-aminoisobutyric acid (Aib)

<400> SEQUENCE: 6

His Xaa Gln Gly Thr Phe Thr Ser Asp Val Ser Ser Tyr Leu Asp Gly
1               5                   10                  15

Gln Ala Ala Lys Glu Phe Val Ala Trp Leu Leu Lys Gly Cys
            20                  25                  30


<210> SEQ ID NO 7
<211> LENGTH: 30
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (2)
<223> OTHER INFORMATION: Xaa is 2-aminoisobutyric acid (Aib)
```

-continued

<400> SEQUENCE: 7

His Xaa Gln Gly Thr Phe Thr Ser Asp Val Ser Lys Tyr Leu Asp Gly
1 5 10 15

Gln Ala Ala Lys Glu Phe Val Ala Trp Leu Leu Lys Gly Cys
20 25 30

<210> SEQ ID NO 8
<211> LENGTH: 30
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (2)
<223> OTHER INFORMATION: Xaa is 2-aminoisobutyric acid (Aib)

<400> SEQUENCE: 8

His Xaa Gln Gly Thr Phe Thr Ser Asp Val Ser Lys Tyr Leu Asp Gly
1 5 10 15

Gln Ala Ala Gln Glu Phe Val Ala Trp Leu Leu Lys Gly Cys
20 25 30

<210> SEQ ID NO 9
<211> LENGTH: 30
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (2)
<223> OTHER INFORMATION: Xaa is 2-aminoisobutyric acid (Aib)

<400> SEQUENCE: 9

His Xaa Gln Gly Thr Phe Thr Ser Asp Val Ser Lys Tyr Leu Asp Gly
1 5 10 15

Gln Ala Ala Gln Glu Phe Val Ala Trp Leu Leu Ala Gly Cys
20 25 30

<210> SEQ ID NO 10
<211> LENGTH: 41
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (2)
<223> OTHER INFORMATION: Xaa is 2-aminoisobutyric acid (Aib)

<400> SEQUENCE: 10

His Xaa Gln Gly Thr Phe Thr Ser Asp Val Ser Lys Tyr Leu Asp Gly
1 5 10 15

Gln Ala Ala Gln Glu Phe Val Ala Trp Leu Leu Ala Gly Gly Gly Pro
20 25 30

Ser Ser Gly Ala Pro Pro Pro Ser Cys
35 40

<210> SEQ ID NO 11
<211> LENGTH: 41
<212> TYPE: PRT
<213> ORGANISM: Artificial Sequence
<220> FEATURE:
<223> OTHER INFORMATION: Trigonal agonist
<220> FEATURE:

<221> NAME/KEY: MISC_FEATURE
<222> LOCATION: (1)
<223> OTHER INFORMATION: Xaa is 4-imidazoacetyl (CA)

<400> SEQUENCE: 11

```
Xaa Gly Glu Gly Thr Phe Thr Ser Asp Leu Ser Lys Tyr Leu Asp Ser
1               5                   10                  15

Arg Arg Gln Gln Leu Phe Val Gln Trp Leu Lys Ala Gly Gly Pro Ser
            20                  25                  30

Ser Gly Ala Pro Pro Pro Ser His Gly
        35                  40
```

<210> SEQ ID NO 12
<211> LENGTH: 41
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (1)
<223> OTHER INFORMATION: Xaa is 4-imidazoacetyl (CA)

<400> SEQUENCE: 12

```
Xaa Gly Glu Gly Thr Phe Ile Ser Asp Leu Ser Lys Tyr Met Asp Glu
1               5                   10                  15

Gln Ala Val Gln Leu Phe Val Glu Trp Leu Met Ala Gly Gly Pro Ser
            20                  25                  30

Ser Gly Ala Pro Pro Pro Ser His Gly
        35                  40
```

<210> SEQ ID NO 13
<211> LENGTH: 41
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (1)
<223> OTHER INFORMATION: Xaa is 4-imidazoacetyl (CA)

<400> SEQUENCE: 13

```
Xaa Gly Glu Gly Thr Phe Ile Ser Asp Tyr Ser Ile Gln Leu Asp Glu
1               5                   10                  15

Ile Ala Val Gln Asp Phe Val Glu Trp Leu Leu Ala Gln Lys Pro Ser
            20                  25                  30

Ser Gly Ala Pro Pro Pro Ser His Gly
        35                  40
```

<210> SEQ ID NO 14
<211> LENGTH: 41
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (1)
<223> OTHER INFORMATION: Xaa is 4-imidazoacetyl (CA)

<400> SEQUENCE: 14

```
Xaa Gly Gln Gly Thr Phe Thr Ser Asp Tyr Ser Ile Gln Leu Asp Glu
1               5                   10                  15
```

```
Ile Ala Val Arg Asp Phe Val Glu Trp Leu Lys Asn Gly Gly Pro Ser
            20                  25                  30

Ser Gly Ala Pro Pro Pro Ser His Gly
        35                  40


<210> SEQ ID NO 15
<211> LENGTH: 41
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (1)
<223> OTHER INFORMATION: Xaa is 4-imidazoacetyl (CA)

<400> SEQUENCE: 15

Xaa Gly Gln Gly Thr Phe Thr Ser Asp Leu Ser Lys Gln Met Asp Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser His Gly
        35                  40


<210> SEQ ID NO 16
<211> LENGTH: 41
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (1)
<223> OTHER INFORMATION: Xaa is 4-imidazoacetyl (CA)

<400> SEQUENCE: 16

Xaa Gly Gln Gly Thr Phe Thr Ser Asp Leu Ser Lys Gln Met Asp Ser
1               5                   10                  15

Glu Ala Gln Gln Leu Phe Ile Glu Trp Leu Lys Asn Gly Gly Pro Ser
            20                  25                  30

Ser Gly Ala Pro Pro Pro Ser His Gly
        35                  40


<210> SEQ ID NO 17
<211> LENGTH: 41
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (1)
<223> OTHER INFORMATION: Xaa is 4-imidazoacetyl (CA)

<400> SEQUENCE: 17

Xaa Gly Gln Gly Thr Phe Thr Ser Asp Leu Ser Lys Gln Met Asp Glu
1               5                   10                  15

Glu Arg Ala Arg Glu Phe Ile Glu Trp Leu Leu Ala Gln Lys Pro Ser
            20                  25                  30

Ser Gly Ala Pro Pro Pro Ser His Gly
        35                  40


<210> SEQ ID NO 18
<211> LENGTH: 41
```

-continued

<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (1)
<223> OTHER INFORMATION: Xaa is 4-imidazoacetyl (CA)

<400> SEQUENCE: 18

Xaa Gly Gln Gly Thr Phe Thr Ser Asp Leu Ser Lys Gln Met Asp Ser
1               5                   10                  15

Glu Arg Ala Arg Glu Phe Ile Glu Trp Leu Lys Asn Thr Gly Pro Ser
            20                  25                  30

Ser Gly Ala Pro Pro Pro Ser His Gly
        35                  40

<210> SEQ ID NO 19
<211> LENGTH: 41
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (1)
<223> OTHER INFORMATION: Xaa is 4-imidazoacetyl (CA)

<400> SEQUENCE: 19

Xaa Gly Gln Gly Thr Phe Thr Ser Asp Leu Ser Ile Gln Tyr Asp Ser
1               5                   10                  15

Glu His Gln Arg Asp Phe Ile Glu Trp Leu Lys Asp Thr Gly Pro Ser
            20                  25                  30

Ser Gly Ala Pro Pro Pro Ser His Gly
        35                  40

<210> SEQ ID NO 20
<211> LENGTH: 41
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (1)
<223> OTHER INFORMATION: Xaa is 4-imidazoacetyl (CA)

<400> SEQUENCE: 20

Xaa Gly Gln Gly Thr Phe Thr Ser Asp Leu Ser Ile Gln Tyr Glu Glu
1               5                   10                  15

Glu Ala Gln Gln Asp Phe Val Glu Trp Leu Lys Asp Thr Gly Pro Ser
            20                  25                  30

Ser Gly Ala Pro Pro Pro Ser His Gly
        35                  40

<210> SEQ ID NO 21
<211> LENGTH: 39
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (2)
<223> OTHER INFORMATION: Xaa is 2-aminoisobutyric acid (Aib)
<220> FEATURE:
<221> NAME/KEY: MISC_FEATURE -continued

```
<222> LOCATION: (16)..(20)
<223> OTHER INFORMATION: amino acids at positions 16 and 20 form a ring

<400> SEQUENCE: 21

Tyr Xaa Gln Gly Thr Phe Thr Ser Asp Tyr Ser Lys Tyr Leu Asp Glu
1               5                   10                  15

Cys Arg Ala Lys Glu Phe Val Gln Trp Leu Leu Asp His His Pro Ser
            20                  25                  30

Ser Gly Gln Pro Pro Pro Ser
        35


<210> SEQ ID NO 22
<211> LENGTH: 39
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (2)
<223> OTHER INFORMATION: Xaa is 2-aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 22

Tyr Xaa Gln Gly Thr Phe Thr Ser Asp Tyr Ser Lys Cys Leu Asp Glu
1               5                   10                  15

Lys Arg Ala Lys Glu Phe Val Gln Trp Leu Leu Asp His His Pro Ser
            20                  25                  30

Ser Gly Gln Pro Pro Pro Ser
        35


<210> SEQ ID NO 23
<211> LENGTH: 41
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (2)
<223> OTHER INFORMATION: Xaa is 2-aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 23

Tyr Xaa Gln Gly Thr Phe Thr Ser Asp Tyr Ser Lys Tyr Leu Asp Glu
1               5                   10                  15

Cys Arg Ala Lys Glu Phe Val Gln Trp Leu Leu Ala Gln Lys Gly Lys
            20                  25                  30

Lys Asn Asp Trp Lys His Asn Ile Thr
        35                  40


<210> SEQ ID NO 24
<211> LENGTH: 39
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (2)
<223> OTHER INFORMATION: Xaa is 2-aminoisobutyric acid (Aib)
```

<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 24

Tyr Xaa Gln Gly Thr Phe Thr Ser Asp Tyr Ser Lys Tyr Leu Asp Glu
1 5 10 15

Cys Arg Ala Lys Glu Phe Val Gln Trp Leu Lys Asn Gly Gly Pro Ser
20 25 30

Ser Gly Ala Pro Pro Pro Ser
35

<210> SEQ ID NO 25
<211> LENGTH: 39
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (2)
<223> OTHER INFORMATION: Xaa is 2-aminoisobutyric acid (Aib)

<400> SEQUENCE: 25

His Xaa Gln Gly Thr Phe Thr Ser Asp Cys Ser Lys Tyr Leu Asp Glu
1 5 10 15

Arg Ala Ala Gln Asp Phe Val Gln Trp Leu Leu Asp Gly Gly Pro Ser
20 25 30

Ser Gly Ala Pro Pro Pro Ser
35

<210> SEQ ID NO 26
<211> LENGTH: 39
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (2)
<223> OTHER INFORMATION: Xaa is 2-aminoisobutyric acid (Aib)

<400> SEQUENCE: 26

His Xaa Gln Gly Thr Phe Thr Ser Asp Cys Ser Lys Tyr Leu Asp Ser
1 5 10 15

Arg Ala Ala Gln Asp Phe Val Gln Trp Leu Leu Asp Gly Gly Pro Ser
20 25 30

Ser Gly Ala Pro Pro Pro Ser
35

<210> SEQ ID NO 27
<211> LENGTH: 40
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (2)
<223> OTHER INFORMATION: Xaa is 2-aminoisobutyric acid (Aib)

<400> SEQUENCE: 27

His Xaa Gln Gly Thr Phe Thr Ser Asp Tyr Ser Lys Tyr Leu Asp Glu
1 5 10 15

-continued

```
Arg Ala Cys Gln Asp Phe Val Gln Trp Leu Leu Asp Gln Gly Gly Pro
            20                  25                  30

Ser Ser Gly Ala Pro Pro Pro Ser
        35                  40


<210> SEQ ID NO 28
<211> LENGTH: 41
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (2)
<223> OTHER INFORMATION: Xaa is 2-aminoisobutyric acid (Aib)

<400> SEQUENCE: 28

His Xaa Gln Gly Thr Phe Thr Ser Asp Tyr Ser Lys Tyr Leu Asp Glu
1               5                   10                  15

Lys Arg Ala Gln Glu Phe Val Cys Trp Leu Leu Ala Gln Lys Gly Lys
            20                  25                  30

Lys Asn Asp Trp Lys His Asn Ile Thr
        35                  40


<210> SEQ ID NO 29
<211> LENGTH: 30
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (2)
<223> OTHER INFORMATION: Xaa is 2-aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 29

His Xaa Gln Gly Thr Phe Thr Ser Asp Tyr Ser Lys Tyr Leu Asp Glu
1               5                   10                  15

Lys Ala Ala Lys Glu Phe Val Gln Trp Leu Leu Asn Thr Cys
            20                  25                  30


<210> SEQ ID NO 30
<211> LENGTH: 30
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (2)
<223> OTHER INFORMATION: Xaa is 2-aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 30

His Xaa Gln Gly Thr Phe Thr Ser Asp Tyr Ser Lys Tyr Leu Asp Glu
1               5                   10                  15

Lys Ala Gln Lys Glu Phe Val Gln Trp Leu Leu Asp Thr Cys
            20                  25                  30


<210> SEQ ID NO 31
```

-continued

```
<211> LENGTH: 29
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (2)
<223> OTHER INFORMATION: Xaa is 2-aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 31

His Xaa Gln Gly Thr Phe Thr Ser Asp Tyr Ser Lys Tyr Leu Asp Glu
1               5                   10                  15

Lys Ala Cys Lys Glu Phe Val Gln Trp Leu Leu Ala Gln
            20                  25


<210> SEQ ID NO 32
<211> LENGTH: 39
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (2)
<223> OTHER INFORMATION: Xaa is 2-aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 32

His Xaa Gln Gly Thr Phe Thr Ser Asp Tyr Ser Lys Tyr Leu Asp Glu
1               5                   10                  15

Lys Ala Cys Lys Asp Phe Val Gln Trp Leu Leu Asp Gly Gly Pro Ser
            20                  25                  30

Ser Gly Ala Pro Pro Pro Ser
        35


<210> SEQ ID NO 33
<211> LENGTH: 31
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (2)
<223> OTHER INFORMATION: Xaa is 2-aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 33

His Xaa Gln Gly Thr Phe Thr Ser Asp Tyr Ser Ile Ala Met Asp Glu
1               5                   10                  15

Ile His Gln Lys Asp Phe Val Asn Trp Leu Leu Ala Gln Lys Cys
            20                  25                  30


<210> SEQ ID NO 34
<211> LENGTH: 31
<212> TYPE: PRT
<213> ORGANISM: Artificial Sequence
<220> FEATURE:
```

<223> OTHER INFORMATION: Trigonal agonist
<220> FEATURE:
<221> NAME/KEY: MISC_FEATURE
<222> LOCATION: (2)
<223> OTHER INFORMATION: Xaa is 2-aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 34

```
His Xaa Gln Gly Thr Phe Thr Ser Asp Tyr Ser Lys Tyr Leu Asp Glu
1               5                   10                  15

Lys Arg Gln Lys Glu Phe Val Asn Trp Leu Leu Ala Gln Lys Cys
            20                  25                  30
```

<210> SEQ ID NO 35
<211> LENGTH: 31
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (2)
<223> OTHER INFORMATION: Xaa is 2-aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 35

```
His Xaa Gln Gly Thr Phe Thr Ser Asp Tyr Ser Ile Ala Met Asp Glu
1               5                   10                  15

Ile His Gln Lys Asp Phe Val Asn Trp Leu Leu Asn Thr Lys Cys
            20                  25                  30
```

<210> SEQ ID NO 36
<211> LENGTH: 40
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (2)
<223> OTHER INFORMATION: Xaa is 2-aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 36

```
His Xaa Gln Gly Thr Phe Thr Ser Asp Tyr Ser Lys Tyr Leu Cys Glu
1               5                   10                  15

Lys Arg Gln Lys Glu Phe Val Gln Trp Leu Leu Asn Gly Gly Pro Ser
            20                  25                  30

Ser Gly Ala Pro Pro Pro Ser Gly
        35                  40
```

<210> SEQ ID NO 37
<211> LENGTH: 40
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (2)

<223> OTHER INFORMATION: Xaa is 2-aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 37

```
His Xaa Gln Gly Thr Phe Thr Ser Asp Tyr Ser Lys Tyr Leu Asp Glu
1               5                   10                  15

Cys Arg Gln Lys Glu Phe Val Gln Trp Leu Leu Asn Gly Gly Pro Ser
            20                  25                  30

Ser Gly Ala Pro Pro Pro Ser Gly
        35                  40
```

<210> SEQ ID NO 38
<211> LENGTH: 40
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (1)
<223> OTHER INFORMATION: Xaa is 4-imidazoacetyl (CA)
<220> FEATURE:
<221> NAME/KEY: MISC_FEATURE
<222> LOCATION: (2)
<223> OTHER INFORMATION: Xaa is 2-aminoisobutyric acid (Aib)

<400> SEQUENCE: 38

```
Xaa Xaa Gln Gly Thr Phe Thr Ser Asp Lys Ser Ser Tyr Leu Asp Glu
1               5                   10                  15

Arg Ala Ala Gln Asp Phe Val Gln Trp Leu Leu Asp Gly Gly Pro Ser
            20                  25                  30

Ser Gly Ala Pro Pro Pro Ser Ser
        35                  40
```

<210> SEQ ID NO 39
<211> LENGTH: 40
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (2)
<223> OTHER INFORMATION: Xaa is 2-aminoisobutyric acid (Aib)

<400> SEQUENCE: 39

```
His Xaa Gln Gly Thr Phe Thr Ser Asp Tyr Ser Lys Tyr Leu Asp Gly
1               5                   10                  15

Gln His Ala Gln Cys Phe Val Ala Trp Leu Leu Ala Gly Gly Gly Pro
            20                  25                  30

Ser Ser Gly Ala Pro Pro Pro Ser
        35                  40
```

<210> SEQ ID NO 40
<211> LENGTH: 39
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (2)
<223> OTHER INFORMATION: Xaa is 2-aminoisobutyric acid (Aib)

<400> SEQUENCE: 40

```
His Xaa Gln Gly Thr Phe Thr Ser Asp Lys Ser Lys Tyr Leu Asp Glu
1               5                   10                  15

Arg Ala Cys Gln Asp Phe Val Gln Trp Leu Leu Asp Gly Gly Pro Ser
            20                  25                  30

Ser Gly Ala Pro Pro Pro Ser
        35
```

<210> SEQ ID NO 41
<211> LENGTH: 39
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (2)
<223> OTHER INFORMATION: Xaa is 2-aminoisobutyric acid (Aib)

<400> SEQUENCE: 41

```
His Xaa Gln Gly Thr Phe Thr Ser Asp Lys Ser Lys Tyr Leu Asp Glu
1               5                   10                  15

Cys Ala Ala Gln Asp Phe Val Gln Trp Leu Leu Asp Gly Gly Pro Ser
            20                  25                  30

Ser Gly Ala Pro Pro Pro Ser
        35
```

<210> SEQ ID NO 42
<211> LENGTH: 40
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (2)
<223> OTHER INFORMATION: Xaa is 2-aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 42

```
Tyr Xaa Gln Gly Thr Phe Thr Ser Asp Tyr Ser Lys Tyr Leu Asp Glu
1               5                   10                  15

Lys Arg Ala Lys Glu Phe Val Gln Trp Leu Leu Asp His His Pro Ser
            20                  25                  30

Ser Gly Gln Pro Pro Pro Ser Cys
        35                  40
```

<210> SEQ ID NO 43
<211> LENGTH: 39
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (2)
<223> OTHER INFORMATION: Xaa is 2-aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 43

Tyr Xaa Gln Gly Thr Phe Thr Ser Asp Tyr Ser Lys Tyr Leu Asp Glu
1               5                   10                  15

Lys Arg Ala Lys Glu Phe Val Gln Trp Leu Leu Asp His His Cys Ser
            20                  25                  30

Ser Gly Gln Pro Pro Pro Ser
        35

<210> SEQ ID NO 44
<211> LENGTH: 39
<212> TYPE: PRT
<213> ORGANISM: Artificial Sequence
<220> FEATURE:
<223> OTHER INFORMATION: Trigonal agonist

<400> SEQUENCE: 44

His Gly Gln Gly Thr Phe Thr Ser Asp Cys Ser Lys Gln Leu Asp Gly
1               5                   10                  15

Gln Ala Ala Gln Glu Phe Val Ala Trp Leu Leu Ala Gly Gly Pro Ser
            20                  25                  30

Ser Gly Ala Pro Pro Pro Ser
        35

<210> SEQ ID NO 45
<211> LENGTH: 39
<212> TYPE: PRT
<213> ORGANISM: Artificial Sequence
<220> FEATURE:
<223> OTHER INFORMATION: Trigonal agonist

<400> SEQUENCE: 45

His Gly Gln Gly Thr Phe Thr Ser Asp Cys Ser Lys Tyr Met Asp Gly
1               5                   10                  15

Gln Ala Ala Gln Asp Phe Val Ala Trp Leu Leu Ala Gly Gly Pro Ser
            20                  25                  30

Ser Gly Ala Pro Pro Pro Ser
        35

<210> SEQ ID NO 46
<211> LENGTH: 39
<212> TYPE: PRT
<213> ORGANISM: Artificial Sequence
<220> FEATURE:
<223> OTHER INFORMATION: Trigonal agonist

<400> SEQUENCE: 46

His Gly Gln Gly Thr Phe Thr Ser Asp Cys Ser Lys Tyr Leu Asp Glu
1               5                   10                  15

Gln His Ala Gln Glu Phe Val Ala Trp Leu Leu Ala Gly Gly Pro Ser
            20                  25                  30

Ser Gly Ala Pro Pro Pro Ser
        35

<210> SEQ ID NO 47
<211> LENGTH: 39
<212> TYPE: PRT
<213> ORGANISM: Artificial Sequence
<220> FEATURE:
<223> OTHER INFORMATION: Trigonal agonist

<400> SEQUENCE: 47

His Gly Gln Gly Thr Phe Thr Ser Asp Cys Ser Lys Tyr Leu Asp Gly
1 5 10 15

Gln Arg Ala Gln Glu Phe Val Ala Trp Leu Leu Ala Gly Gly Pro Ser
20 25 30

Ser Gly Ala Pro Pro Pro Ser
35

<210> SEQ ID NO 48
<211> LENGTH: 39
<212> TYPE: PRT
<213> ORGANISM: Artificial Sequence
<220> FEATURE:
<223> OTHER INFORMATION: Trigonal agonist

<400> SEQUENCE: 48

His Gly Gln Gly Thr Phe Thr Ser Asp Cys Ser Lys Tyr Leu Asp Gly
1 5 10 15

Gln Arg Ala Gln Asp Phe Val Asn Trp Leu Leu Ala Gly Gly Pro Ser
20 25 30

Ser Gly Ala Pro Pro Pro Ser
35

<210> SEQ ID NO 49
<211> LENGTH: 30
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (1)
<223> OTHER INFORMATION: Xaa is 4-imidazoacetyl (CA)
<220> FEATURE:
<221> NAME/KEY: MISC_FEATURE
<222> LOCATION: (2)
<223> OTHER INFORMATION: Xaa is 2-aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 49

Xaa Xaa Gln Gly Thr Phe Thr Ser Asp Tyr Ser Ile Cys Met Asp Glu
1 5 10 15

Ile His Gln Lys Asp Phe Val Asn Trp Leu Leu Asn Thr Lys
20 25 30

<210> SEQ ID NO 50
<211> LENGTH: 40
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (2)
<223> OTHER INFORMATION: Xaa is 2-aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 50

His Xaa Gln Gly Thr Phe Thr Ser Asp Tyr Ser Lys Tyr Leu Asp Glu
1 5 10 15

```
Lys Arg Ala Lys Glu Phe Val Gln Trp Leu Leu Asp His His Pro Ser
            20                  25                  30

Ser Gly Gln Pro Pro Pro Ser Cys
        35                  40


<210> SEQ ID NO 51
<211> LENGTH: 30
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (2)
<223> OTHER INFORMATION: Xaa is 2-aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 51

His Xaa Gln Gly Thr Phe Thr Ser Asp Tyr Ser Lys Tyr Leu Asp Glu
1               5                   10                  15

Lys Arg Gln Lys Glu Phe Val Gln Trp Leu Leu Asn Thr Cys
            20                  25                  30


<210> SEQ ID NO 52
<211> LENGTH: 30
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (2)
<223> OTHER INFORMATION: Xaa is 2-aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 52

His Xaa Gln Gly Thr Phe Thr Ser Asp Tyr Ser Lys Tyr Leu Asp Glu
1               5                   10                  15

Lys Arg Gln Lys Glu Phe Val Gln Trp Leu Leu Asp Thr Cys
            20                  25                  30


<210> SEQ ID NO 53
<211> LENGTH: 30
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (2)
<223> OTHER INFORMATION: Xaa is 2-aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 53

His Xaa Glu Gly Thr Phe Thr Ser Asp Tyr Ser Ile Ala Met Asp Glu
1               5                   10                  15

Ile His Gln Lys Asp Phe Val Asn Trp Leu Leu Ala Gln Cys
            20                  25                  30
```

<210> SEQ ID NO 54
<211> LENGTH: 30
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (2)
<223> OTHER INFORMATION: Xaa is 2-aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 54

His Xaa Glu Gly Thr Phe Thr Ser Asp Tyr Ser Ile Ala Met Asp Glu
1               5                   10                  15

Ile His Gln Lys Asp Phe Val Asp Trp Leu Leu Ala Glu Cys
            20                  25                  30

<210> SEQ ID NO 55
<211> LENGTH: 30
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (2)
<223> OTHER INFORMATION: Xaa is 2-aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 55

His Xaa Gln Gly Thr Phe Thr Ser Asp Tyr Ser Ile Ala Met Asp Glu
1               5                   10                  15

Ile His Gln Lys Asp Phe Val Asn Trp Leu Leu Ala Gln Cys
            20                  25                  30

<210> SEQ ID NO 56
<211> LENGTH: 30
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (2)
<223> OTHER INFORMATION: Xaa is 2-aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 56

His Xaa Gln Gly Thr Phe Thr Ser Asp Tyr Ser Lys Tyr Leu Asp Glu
1               5                   10                  15

Lys Arg Gln Lys Glu Phe Val Asn Trp Leu Leu Ala Gln Cys
            20                  25                  30

<210> SEQ ID NO 57
<211> LENGTH: 30
<212> TYPE: PRT
<213> ORGANISM: Artificial Sequence
<220> FEATURE:
<223> OTHER INFORMATION: Trigonal agonist -continued
<220> FEATURE:
<221> NAME/KEY: MISC_FEATURE
<222> LOCATION: (2)
<223> OTHER INFORMATION: Xaa is 2-aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 57

His Xaa Gln Gly Thr Phe Thr Ser Asp Tyr Ser Ile Ala Met Asp Glu
1 5 10 15

Ile His Gln Lys Asp Phe Val Asn Trp Leu Leu Asn Thr Cys
20 25 30

<210> SEQ ID NO 58
<211> LENGTH: 31
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (2)
<223> OTHER INFORMATION: Xaa is 2-aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 58

His Xaa Gln Gly Thr Phe Thr Ser Asp Tyr Ser Lys Tyr Leu Asp Glu
1 5 10 15

Lys Arg Gln Lys Glu Phe Val Gln Trp Leu Leu Asn Thr Lys Cys
20 25 30

<210> SEQ ID NO 59
<211> LENGTH: 30
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (1)
<223> OTHER INFORMATION: Xaa is 4-imidazoacetyl (CA)
<220> FEATURE:
<221> NAME/KEY: MISC_FEATURE
<222> LOCATION: (2)
<223> OTHER INFORMATION: Xaa is 2-aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 59

Xaa Xaa Gln Gly Thr Phe Thr Ser Asp Tyr Ser Ile Cys Met Asp Glu
1 5 10 15

Lys His Gln Lys Asp Phe Val Asn Trp Leu Leu Asn Thr Lys
20 25 30

<210> SEQ ID NO 60
<211> LENGTH: 30
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (1)

<223> OTHER INFORMATION: Xaa is 4-imidazoacetyl (CA)
<220> FEATURE:
<221> NAME/KEY: MISC_FEATURE
<222> LOCATION: (2)
<223> OTHER INFORMATION: Xaa is 2-aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 60

```
Xaa Xaa Gln Gly Thr Phe Thr Ser Asp Tyr Ser Ile Ala Met Asp Glu
1               5                   10                  15

Lys His Cys Lys Asp Phe Val Asn Trp Leu Leu Asn Thr Lys
            20                  25                  30
```

<210> SEQ ID NO 61
<211> LENGTH: 30
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (1)
<223> OTHER INFORMATION: Xaa is 4-imidazoacetyl (CA)
<220> FEATURE:
<221> NAME/KEY: MISC_FEATURE
<222> LOCATION: (2)
<223> OTHER INFORMATION: Xaa is 2-aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 61

```
Xaa Xaa Gln Gly Thr Phe Thr Ser Asp Tyr Ser Ile Ala Met Asp Glu
1               5                   10                  15

Ile Ala Cys Lys Asp Phe Val Asn Trp Leu Leu Asn Thr Lys
            20                  25                  30
```

<210> SEQ ID NO 62
<211> LENGTH: 39
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (1)
<223> OTHER INFORMATION: Xaa is 4-imidazoacetyl (CA)
<220> FEATURE:
<221> NAME/KEY: MISC_FEATURE
<222> LOCATION: (2)
<223> OTHER INFORMATION: Xaa is 2-aminoisobutyric acid (Aib)

<400> SEQUENCE: 62

```
Xaa Xaa Gln Gly Thr Phe Thr Ser Asp Lys Ser Lys Tyr Leu Asp Glu
1               5                   10                  15

Arg Ala Ala Gln Asp Phe Val Gln Trp Leu Leu Asp Gly Gly Pro Ser
            20                  25                  30

Ser Gly Ala Pro Pro Pro Ser
        35
```

<210> SEQ ID NO 63
<211> LENGTH: 39
<212> TYPE: PRT
<213> ORGANISM: Artificial Sequence
<220> FEATURE:

<223> OTHER INFORMATION: Trigonal agonist
<220> FEATURE:
<221> NAME/KEY: MISC_FEATURE
<222> LOCATION: (1)
<223> OTHER INFORMATION: Xaa is 4-imidazoacetyl (CA)
<220> FEATURE:
<221> NAME/KEY: MISC_FEATURE
<222> LOCATION: (2)
<223> OTHER INFORMATION: Xaa is 2-aminoisobutyric acid (Aib)

<400> SEQUENCE: 63

```
Xaa Xaa Gln Gly Thr Phe Thr Ser Asp Cys Ser Lys Tyr Leu Asp Glu
1               5                   10                  15

Arg Ala Ala Gln Asp Phe Val Gln Trp Leu Leu Asp Gly Gly Pro Ser
            20                  25                  30

Ser Gly Ala Pro Pro Pro Ser
        35
```

<210> SEQ ID NO 64
<211> LENGTH: 39
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (2)
<223> OTHER INFORMATION: Xaa is 2-aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 64

```
Tyr Xaa Gln Gly Thr Phe Thr Ser Asp Tyr Ser Lys Tyr Leu Asp Glu
1               5                   10                  15

Cys Ala Ala Lys Glu Phe Val Gln Trp Leu Leu Asp His His Pro Ser
            20                  25                  30

Ser Gly Gln Pro Pro Pro Ser
        35
```

<210> SEQ ID NO 65
<211> LENGTH: 39
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (2)
<223> OTHER INFORMATION: Xaa is 2-aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 65

```
His Xaa Gln Gly Thr Phe Thr Ser Asp Tyr Ser Lys Cys Leu Asp Glu
1               5                   10                  15

Lys Arg Ala Lys Glu Phe Val Gln Trp Leu Leu Asp His His Pro Ser
            20                  25                  30

Ser Gly Gln Pro Pro Pro Ser
        35
```

<210> SEQ ID NO 66
<211> LENGTH: 39
<212> TYPE: PRT

-continued

<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (2)
<223> OTHER INFORMATION: Xaa is 2-aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 66

```
Tyr Xaa Gln Gly Thr Phe Thr Ser Asp Tyr Ser Lys Tyr Leu Asp Glu
1               5                   10                  15

Cys Arg Ala Lys Asp Phe Val Gln Trp Leu Leu Asp His His Pro Ser
            20                  25                  30

Ser Gly Gln Pro Pro Pro Ser
        35
```

<210> SEQ ID NO 67
<211> LENGTH: 39
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (2)
<223> OTHER INFORMATION: Xaa is 2-aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 67

```
Tyr Xaa Gln Gly Thr Phe Thr Ser Asp Tyr Ser Lys Tyr Leu Asp Glu
1               5                   10                  15

Cys Ala Ala Lys Asp Phe Val Gln Trp Leu Leu Asp His His Pro Ser
            20                  25                  30

Ser Gly Gln Pro Pro Pro Ser
        35
```

<210> SEQ ID NO 68
<211> LENGTH: 39
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (2)
<223> OTHER INFORMATION: Xaa is 2-aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 68

```
Tyr Xaa Gln Gly Thr Phe Thr Ser Asp Tyr Ser Lys Cys Leu Asp Glu
1               5                   10                  15

Lys Ala Ala Lys Glu Phe Val Gln Trp Leu Leu Asp His His Pro Ser
            20                  25                  30

Ser Gly Gln Pro Pro Pro Ser
        35
```

<210> SEQ ID NO 69

<211> LENGTH: 39
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (2)
<223> OTHER INFORMATION: Xaa is 2-aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 69

```
Tyr Xaa Gln Gly Thr Phe Thr Ser Asp Tyr Ser Lys Cys Leu Asp Glu
1               5                   10                  15

Arg Ala Ala Lys Glu Phe Val Gln Trp Leu Leu Asp His His Pro Ser
            20                  25                  30

Ser Gly Gln Pro Pro Pro Ser
        35
```

<210> SEQ ID NO 70
<211> LENGTH: 39
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (2)
<223> OTHER INFORMATION: Xaa is 2-aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 70

```
Tyr Xaa Gln Gly Thr Phe Thr Ser Asp Tyr Ser Lys Cys Leu Asp Glu
1               5                   10                  15

Lys Arg Ala Lys Asp Phe Val Gln Trp Leu Leu Asp His His Pro Ser
            20                  25                  30

Ser Gly Gln Pro Pro Pro Ser
        35
```

<210> SEQ ID NO 71
<211> LENGTH: 39
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (2)
<223> OTHER INFORMATION: Xaa is 2-aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 71

```
Tyr Xaa Gln Gly Thr Phe Thr Ser Asp Tyr Ser Lys Tyr Leu Asp Glu
1               5                   10                  15

Arg Ala Cys Lys Asp Phe Val Gln Trp Leu Leu Asp His His Pro Ser
            20                  25                  30

Ser Gly Gln Pro Pro Pro Ser
        35
```

<210> SEQ ID NO 72
<211> LENGTH: 39
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (2)
<223> OTHER INFORMATION: Xaa is 2-aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 72

```
Tyr Xaa Gln Gly Thr Phe Thr Ser Asp Cys Ser Lys Tyr Leu Asp Glu
1               5                   10                  15

Arg Ala Ala Lys Asp Phe Val Gln Trp Leu Leu Asp His His Pro Ser
            20                  25                  30

Ser Gly Gln Pro Pro Pro Ser
        35
```

<210> SEQ ID NO 73
<211> LENGTH: 39
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (1)
<223> OTHER INFORMATION: Xaa is 4-imidazoacetyl (CA)
<220> FEATURE:
<221> NAME/KEY: MISC_FEATURE
<222> LOCATION: (2)
<223> OTHER INFORMATION: Xaa is 2-aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 73

```
Xaa Xaa Gln Gly Thr Phe Thr Ser Asp Tyr Ser Lys Tyr Leu Asp Glu
1               5                   10                  15

Cys Arg Ala Lys Glu Phe Val Gln Trp Leu Leu Asp His His Pro Ser
            20                  25                  30

Ser Gly Gln Pro Pro Pro Ser
        35
```

<210> SEQ ID NO 74
<211> LENGTH: 39
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (1)
<223> OTHER INFORMATION: Xaa is 4-imidazoacetyl (CA)
<220> FEATURE:
<221> NAME/KEY: MISC_FEATURE
<222> LOCATION: (2)
<223> OTHER INFORMATION: Xaa is 2-aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 74

Xaa Xaa Gln Gly Thr Phe Thr Ser Asp Tyr Ser Lys Cys Leu Asp Glu
1               5                   10                  15

Lys Arg Ala Lys Glu Phe Val Gln Trp Leu Leu Asp His His Pro Ser
            20                  25                  30

Ser Gly Gln Pro Pro Pro Ser
        35

<210> SEQ ID NO 75
<211> LENGTH: 40
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (2)
<223> OTHER INFORMATION: Xaa is 2-aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 75

Tyr Xaa Gln Gly Thr Phe Thr Ser Asp Tyr Ser Lys Tyr Leu Asp Glu
1               5                   10                  15

Lys Ala Ala Lys Glu Phe Val Gln Trp Leu Leu Asp His His Pro Ser
            20                  25                  30

Ser Gly Gln Pro Pro Pro Ser Cys
        35                  40

<210> SEQ ID NO 76
<211> LENGTH: 40
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (2)
<223> OTHER INFORMATION: Xaa is 2-aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 76

Tyr Xaa Gln Gly Thr Phe Thr Ser Asp Tyr Ser Lys Tyr Leu Asp Glu
1               5                   10                  15

Lys Arg Ala Lys Asp Phe Val Gln Trp Leu Leu Asp His His Pro Ser
            20                  25                  30

Ser Gly Gln Pro Pro Pro Ser Cys
        35                  40

<210> SEQ ID NO 77
<211> LENGTH: 40
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (2)
<223> OTHER INFORMATION: Xaa is 2-aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 77

Tyr Xaa Gln Gly Thr Phe Thr Ser Asp Tyr Ser Lys Tyr Leu Asp Glu
1 5 10 15

Lys Ala Ala Lys Asp Phe Val Gln Trp Leu Leu Asp His His Pro Ser
20 25 30

Ser Gly Gln Pro Pro Pro Ser Cys
35 40

<210> SEQ ID NO 78
<211> LENGTH: 31
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (2)
<223> OTHER INFORMATION: Xaa is 2-aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 78

His Xaa Gln Gly Thr Phe Thr Ser Asp Tyr Ser Lys Tyr Leu Asp Glu
1 5 10 15

Lys Arg Gln Lys Glu Phe Val Gln Trp Leu Leu Asp Thr Lys Cys
20 25 30

<210> SEQ ID NO 79
<211> LENGTH: 31
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (2)
<223> OTHER INFORMATION: Xaa is 2-aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 79

His Xaa Glu Gly Thr Phe Thr Ser Asp Tyr Ser Ile Ala Met Asp Glu
1 5 10 15

Ile His Gln Lys Asp Phe Val Asn Trp Leu Leu Ala Gln Lys Cys
20 25 30

<210> SEQ ID NO 80
<211> LENGTH: 31
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (2)
<223> OTHER INFORMATION: Xaa is 2-aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 80

His Xaa Glu Gly Thr Phe Thr Ser Asp Tyr Ser Ile Ala Met Asp Glu
1 5 10 15

Ile His Gln Lys Asp Phe Val Asp Trp Leu Leu Ala Glu Lys Cys
20 25 30

<210> SEQ ID NO 81
<211> LENGTH: 30
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (1)
<223> OTHER INFORMATION: Xaa is 4-imidazoacetyl (CA)
<220> FEATURE:
<221> NAME/KEY: MISC_FEATURE
<222> LOCATION: (2)
<223> OTHER INFORMATION: Xaa is 2-aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 81

Xaa Xaa Gln Gly Thr Phe Thr Ser Asp Tyr Ser Lys Tyr Leu Asp Glu
1 5 10 15

Lys Arg Gln Lys Glu Phe Val Gln Trp Leu Leu Asn Thr Cys
20 25 30

<210> SEQ ID NO 82
<211> LENGTH: 30
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (1)
<223> OTHER INFORMATION: Xaa is 4-imidazoacetyl (CA)
<220> FEATURE:
<221> NAME/KEY: MISC_FEATURE
<222> LOCATION: (2)
<223> OTHER INFORMATION: Xaa is 2-aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 82

Xaa Xaa Gln Gly Thr Phe Thr Ser Asp Tyr Ser Lys Tyr Leu Asp Glu
1 5 10 15

Lys Arg Gln Lys Glu Phe Val Gln Trp Leu Leu Asp Thr Cys
20 25 30

<210> SEQ ID NO 83
<211> LENGTH: 30
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (1)
<223> OTHER INFORMATION: Xaa is 4-imidazoacetyl (CA)
<220> FEATURE:
<221> NAME/KEY: MISC_FEATURE
<222> LOCATION: (2)

<223> OTHER INFORMATION: Xaa is 2-aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 83

```
Xaa Xaa Glu Gly Thr Phe Thr Ser Asp Tyr Ser Ile Ala Met Asp Glu
1               5                   10                  15

Ile His Gln Lys Asp Phe Val Asn Trp Leu Leu Ala Gln Cys
            20                  25                  30
```

<210> SEQ ID NO 84
<211> LENGTH: 30
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (1)
<223> OTHER INFORMATION: Xaa is 4-imidazoacetyl (CA)
<220> FEATURE:
<221> NAME/KEY: MISC_FEATURE
<222> LOCATION: (2)
<223> OTHER INFORMATION: Xaa is 2-aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 84

```
Xaa Xaa Glu Gly Thr Phe Thr Ser Asp Tyr Ser Ile Ala Met Asp Glu
1               5                   10                  15

Ile His Gln Lys Asp Phe Val Asp Trp Leu Leu Ala Glu Cys
            20                  25                  30
```

<210> SEQ ID NO 85
<211> LENGTH: 30
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (1)
<223> OTHER INFORMATION: Xaa is 4-imidazoacetyl (CA)
<220> FEATURE:
<221> NAME/KEY: MISC_FEATURE
<222> LOCATION: (2)
<223> OTHER INFORMATION: Xaa is 2-aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 85

```
Xaa Xaa Gln Gly Thr Phe Thr Ser Asp Tyr Ser Ile Ala Met Asp Glu
1               5                   10                  15

Ile His Gln Lys Asp Phe Val Asn Trp Leu Leu Ala Gln Cys
            20                  25                  30
```

<210> SEQ ID NO 86
<211> LENGTH: 30
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (1)
<223> OTHER INFORMATION: Xaa is 4-imidazoacetyl (CA)
<220> FEATURE:
<221> NAME/KEY: MISC_FEATURE
<222> LOCATION: (2)
<223> OTHER INFORMATION: Xaa is 2-aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 86

```
Xaa Xaa Gln Gly Thr Phe Thr Ser Asp Tyr Ser Lys Tyr Leu Asp Glu
1               5                   10                  15

Lys Arg Gln Lys Glu Phe Val Asn Trp Leu Leu Ala Gln Cys
            20                  25                  30
```

<210> SEQ ID NO 87
<211> LENGTH: 30
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (1)
<223> OTHER INFORMATION: Xaa is 4-imidazoacetyl (CA)
<220> FEATURE:
<221> NAME/KEY: MISC_FEATURE
<222> LOCATION: (2)
<223> OTHER INFORMATION: Xaa is 2-aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 87

```
Xaa Xaa Gln Gly Thr Phe Thr Ser Asp Tyr Ser Ile Ala Met Asp Glu
1               5                   10                  15

Ile His Gln Lys Asp Phe Val Asn Trp Leu Leu Asn Thr Cys
            20                  25                  30
```

<210> SEQ ID NO 88
<211> LENGTH: 31
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (1)
<223> OTHER INFORMATION: Xaa is 4-imidazoacetyl (CA)
<220> FEATURE:
<221> NAME/KEY: MISC_FEATURE
<222> LOCATION: (2)
<223> OTHER INFORMATION: Xaa is 2-aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 88

```
Xaa Xaa Gln Gly Thr Phe Thr Ser Asp Tyr Ser Lys Tyr Leu Asp Glu
1               5                   10                  15

Lys Arg Gln Lys Glu Phe Val Gln Trp Leu Leu Asn Thr Lys Cys
            20                  25                  30
```

<210> SEQ ID NO 89
<211> LENGTH: 31
<212> TYPE: PRT

<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (1)
<223> OTHER INFORMATION: Xaa is 4-imidazoacetyl (CA)
<220> FEATURE:
<221> NAME/KEY: MISC_FEATURE
<222> LOCATION: (2)
<223> OTHER INFORMATION: Xaa is 2-aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 89

```
Xaa Xaa Gln Gly Thr Phe Thr Ser Asp Tyr Ser Lys Tyr Leu Asp Glu
1               5                   10                  15

Lys Arg Gln Lys Glu Phe Val Gln Trp Leu Leu Asp Thr Lys Cys
            20                  25                  30
```

<210> SEQ ID NO 90
<211> LENGTH: 31
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (1)
<223> OTHER INFORMATION: Xaa is 4-imidazoacetyl (CA)
<220> FEATURE:
<221> NAME/KEY: MISC_FEATURE
<222> LOCATION: (2)
<223> OTHER INFORMATION: Xaa is 2-aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 90

```
Xaa Xaa Glu Gly Thr Phe Thr Ser Asp Tyr Ser Ile Ala Met Asp Glu
1               5                   10                  15

Ile His Gln Lys Asp Phe Val Asn Trp Leu Leu Ala Gln Lys Cys
            20                  25                  30
```

<210> SEQ ID NO 91
<211> LENGTH: 31
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (1)
<223> OTHER INFORMATION: Xaa is 4-imidazoacetyl (CA)
<220> FEATURE:
<221> NAME/KEY: MISC_FEATURE
<222> LOCATION: (2)
<223> OTHER INFORMATION: Xaa is 2-aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 91

```
Xaa Xaa Glu Gly Thr Phe Thr Ser Asp Tyr Ser Ile Ala Met Asp Glu
1               5                   10                  15

Ile His Gln Lys Asp Phe Val Asp Trp Leu Leu Ala Glu Lys Cys
            20                  25                  30
```

<210> SEQ ID NO 92
<211> LENGTH: 31
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (1)
<223> OTHER INFORMATION: Xaa is 4-imidazoacetyl (CA)
<220> FEATURE:
<221> NAME/KEY: MISC_FEATURE
<222> LOCATION: (2)
<223> OTHER INFORMATION: Xaa is 2-aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 92

```
Xaa Xaa Gln Gly Thr Phe Thr Ser Asp Tyr Ser Ile Ala Met Asp Glu
1               5                   10                  15

Ile His Gln Lys Asp Phe Val Asn Trp Leu Leu Ala Gln Lys Cys
            20                  25                  30
```

<210> SEQ ID NO 93
<211> LENGTH: 31
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (1)
<223> OTHER INFORMATION: Xaa is 4-imidazoacetyl (CA)
<220> FEATURE:
<221> NAME/KEY: MISC_FEATURE
<222> LOCATION: (2)
<223> OTHER INFORMATION: Xaa is 2-aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 93

```
Xaa Xaa Gln Gly Thr Phe Thr Ser Asp Tyr Ser Lys Tyr Leu Asp Glu
1               5                   10                  15

Lys Arg Gln Lys Glu Phe Val Asn Trp Leu Leu Ala Gln Lys Cys
            20                  25                  30
```

<210> SEQ ID NO 94
<211> LENGTH: 31
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (1)
<223> OTHER INFORMATION: Xaa is 4-imidazoacetyl (CA)
<220> FEATURE:
<221> NAME/KEY: MISC_FEATURE
<222> LOCATION: (2)
<223> OTHER INFORMATION: Xaa is 2-aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 94

Xaa Xaa Gln Gly Thr Phe Thr Ser Asp Tyr Ser Ile Ala Met Asp Glu
1 5 10 15

Ile His Gln Lys Asp Phe Val Asn Trp Leu Leu Asn Thr Lys Cys
20 25 30

<210> SEQ ID NO 95
<211> LENGTH: 39
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (2)
<223> OTHER INFORMATION: Xaa is 2-aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 95

Tyr Xaa Gln Gly Thr Phe Thr Ser Asp Tyr Ser Lys Tyr Leu Asp Glu
1 5 10 15

Lys Arg Ala Lys Glu Phe Val Gln Trp Leu Leu Cys His His Pro Ser
20 25 30

Ser Gly Gln Pro Pro Pro Ser
35

<210> SEQ ID NO 96
<211> LENGTH: 39
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (2)
<223> OTHER INFORMATION: Xaa is 2-aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 96

Tyr Xaa Gln Gly Thr Phe Thr Ser Asp Tyr Ser Lys Tyr Leu Asp Glu
1 5 10 15

Lys Arg Ala Lys Glu Phe Val Gln Trp Leu Leu Asp His Cys Pro Ser
20 25 30

Ser Gly Gln Pro Pro Pro Ser
35

<210> SEQ ID NO 97
<211> LENGTH: 39
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (2)
<223> OTHER INFORMATION: Xaa is 2-aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 97

Tyr Xaa Gln Gly Thr Phe Thr Ser Asp Tyr Ser Lys Tyr Leu Asp Glu
1               5                   10                  15

Lys Arg Ala Lys Glu Phe Val Gln Trp Leu Leu Asp Cys His Pro Ser
            20                  25                  30

Ser Gly Gln Pro Pro Pro Ser
        35

<210> SEQ ID NO 98
<211> LENGTH: 40
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (2)
<223> OTHER INFORMATION: Xaa is 2-aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 98

Tyr Xaa Gln Gly Thr Phe Thr Ser Asp Tyr Ser Lys Ala Leu Asp Glu
1               5                   10                  15

Lys Ala Ala Lys Glu Phe Val Asn Trp Leu Leu Asp His His Pro Ser
            20                  25                  30

Ser Gly Gln Pro Pro Pro Ser Cys
        35                  40

<210> SEQ ID NO 99
<211> LENGTH: 40
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (2)
<223> OTHER INFORMATION: Xaa is 2-aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 99

Tyr Xaa Gln Gly Thr Phe Thr Ser Asp Tyr Ser Lys Ala Leu Asp Glu
1               5                   10                  15

Lys Ala Ala Lys Asp Phe Val Asn Trp Leu Leu Asp His His Pro Ser
            20                  25                  30

Ser Gly Gln Pro Pro Pro Ser Cys
        35                  40

<210> SEQ ID NO 100
<211> LENGTH: 40
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (2)
<223> OTHER INFORMATION: Xaa is 2-aminoisobutyric acid (Aib)
<220> FEATURE:
<221> NAME/KEY: MISC_FEATURE
<222> LOCATION: (16)..(20)

<223> OTHER INFORMATION: amino acids at positions 16 and 20 form a ring

<400> SEQUENCE: 100

Tyr Xaa Gln Gly Thr Phe Thr Ser Asp Tyr Ser Lys Ala Leu Asp Glu
1               5                   10                  15

Lys Ala Ala Lys Glu Phe Val Gln Trp Leu Leu Asp Gln His Pro Ser
            20                  25                  30

Ser Gly Gln Pro Pro Pro Ser Cys
        35                  40

<210> SEQ ID NO 101
<211> LENGTH: 40
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (2)
<223> OTHER INFORMATION: Xaa is 2-aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 101

Tyr Xaa Gln Gly Thr Phe Thr Ser Asp Tyr Ser Lys Ala Leu Asp Glu
1               5                   10                  15

Lys Ala Ala Lys Glu Phe Val Asn Trp Leu Leu Asp Gln His Pro Ser
            20                  25                  30

Ser Gly Gln Pro Pro Pro Ser Cys
        35                  40

<210> SEQ ID NO 102
<211> LENGTH: 40
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (2)
<223> OTHER INFORMATION: Xaa is 2-aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 102

Tyr Xaa Gln Gly Thr Phe Thr Ser Asp Tyr Ser Lys Ala Leu Asp Glu
1               5                   10                  15

Lys Ala Ala Lys Asp Phe Val Asn Trp Leu Leu Asp Gln His Pro Ser
            20                  25                  30

Ser Gly Gln Pro Pro Pro Ser Cys
        35                  40

<210> SEQ ID NO 103
<211> LENGTH: 12
<212> TYPE: PRT
<213> ORGANISM: HOMO SAPIENS

<400> SEQUENCE: 103

Glu Ser Lys Tyr Gly Pro Pro Cys Pro Ser Cys Pro
1               5                   10

<210> SEQ ID NO 104
<211> LENGTH: 11
<212> TYPE: PRT
<213> ORGANISM: Artificial Sequence
<220> FEATURE:
<223> OTHER INFORMATION: Variant of hinge region

<400> SEQUENCE: 104

```
Glu Ser Lys Tyr Gly Pro Pro Pro Ser Cys Pro
1               5                   10
```

<210> SEQ ID NO 105
<211> LENGTH: 11
<212> TYPE: PRT
<213> ORGANISM: Artificial Sequence
<220> FEATURE:
<223> OTHER INFORMATION: Variant of hinge region

<400> SEQUENCE: 105

```
Glu Ser Lys Tyr Gly Pro Pro Cys Pro Ser Pro
1               5                   10
```

<210> SEQ ID NO 106
<211> LENGTH: 10
<212> TYPE: PRT
<213> ORGANISM: Artificial Sequence
<220> FEATURE:
<223> OTHER INFORMATION: Variant of hinge region

<400> SEQUENCE: 106

```
Glu Ser Lys Tyr Gly Pro Pro Cys Pro Ser
1               5                   10
```

<210> SEQ ID NO 107
<211> LENGTH: 10
<212> TYPE: PRT
<213> ORGANISM: Artificial Sequence
<220> FEATURE:
<223> OTHER INFORMATION: Variant of hinge region

<400> SEQUENCE: 107

```
Glu Ser Lys Tyr Gly Pro Pro Cys Pro Pro
1               5                   10
```

<210> SEQ ID NO 108
<211> LENGTH: 8
<212> TYPE: PRT
<213> ORGANISM: Artificial Sequence
<220> FEATURE:
<223> OTHER INFORMATION: Variant of hinge region

<400> SEQUENCE: 108

```
Lys Tyr Gly Pro Pro Cys Pro Ser
1               5
```

<210> SEQ ID NO 109
<211> LENGTH: 8
<212> TYPE: PRT
<213> ORGANISM: Artificial Sequence
<220> FEATURE:
<223> OTHER INFORMATION: Variant of hinge region

<400> SEQUENCE: 109

```
Glu Ser Lys Tyr Gly Pro Pro Cys
1               5
```

<210> SEQ ID NO 110

<211> LENGTH: 7
<212> TYPE: PRT
<213> ORGANISM: Artificial Sequence
<220> FEATURE:
<223> OTHER INFORMATION: Variant of hinge region

<400> SEQUENCE: 110

Glu Lys Tyr Gly Pro Pro Cys
1 5

<210> SEQ ID NO 111
<211> LENGTH: 6
<212> TYPE: PRT
<213> ORGANISM: Artificial Sequence
<220> FEATURE:
<223> OTHER INFORMATION: Variant of hinge region

<400> SEQUENCE: 111

Glu Ser Pro Ser Cys Pro
1 5

<210> SEQ ID NO 112
<211> LENGTH: 5
<212> TYPE: PRT
<213> ORGANISM: Artificial Sequence
<220> FEATURE:
<223> OTHER INFORMATION: Variant of hinge region

<400> SEQUENCE: 112

Glu Pro Ser Cys Pro
1 5

<210> SEQ ID NO 113
<211> LENGTH: 4
<212> TYPE: PRT
<213> ORGANISM: Artificial Sequence
<220> FEATURE:
<223> OTHER INFORMATION: Variant of hinge region

<400> SEQUENCE: 113

Pro Ser Cys Pro
1

<210> SEQ ID NO 114
<211> LENGTH: 10
<212> TYPE: PRT
<213> ORGANISM: Artificial Sequence
<220> FEATURE:
<223> OTHER INFORMATION: Variant of hinge region

<400> SEQUENCE: 114

Glu Ser Lys Tyr Gly Pro Pro Ser Cys Pro
1 5 10

<210> SEQ ID NO 115
<211> LENGTH: 9
<212> TYPE: PRT
<213> ORGANISM: Artificial Sequence
<220> FEATURE:
<223> OTHER INFORMATION: Variant of hinge region

<400> SEQUENCE: 115

Lys Tyr Gly Pro Pro Pro Ser Cys Pro
1 5

<210> SEQ ID NO 116
<211> LENGTH: 9

<212> TYPE: PRT
<213> ORGANISM: Artificial Sequence
<220> FEATURE:
<223> OTHER INFORMATION: Variant of hinge region

<400> SEQUENCE: 116

Glu Ser Lys Tyr Gly Pro Ser Cys Pro
1               5

<210> SEQ ID NO 117
<211> LENGTH: 8
<212> TYPE: PRT
<213> ORGANISM: Artificial Sequence
<220> FEATURE:
<223> OTHER INFORMATION: Variant of hinge region

<400> SEQUENCE: 117

Glu Ser Lys Tyr Gly Pro Pro Cys
1               5

<210> SEQ ID NO 118
<211> LENGTH: 7
<212> TYPE: PRT
<213> ORGANISM: Artificial Sequence
<220> FEATURE:
<223> OTHER INFORMATION: Variant of hinge region

<400> SEQUENCE: 118

Lys Tyr Gly Pro Pro Cys Pro
1               5

<210> SEQ ID NO 119
<211> LENGTH: 7
<212> TYPE: PRT
<213> ORGANISM: Artificial Sequence
<220> FEATURE:
<223> OTHER INFORMATION: Variant of hinge region

<400> SEQUENCE: 119

Glu Ser Lys Pro Ser Cys Pro
1               5

<210> SEQ ID NO 120
<211> LENGTH: 6
<212> TYPE: PRT
<213> ORGANISM: Artificial Sequence
<220> FEATURE:
<223> OTHER INFORMATION: Variant of hinge region

<400> SEQUENCE: 120

Glu Ser Pro Ser Cys Pro
1               5

<210> SEQ ID NO 121
<211> LENGTH: 4
<212> TYPE: PRT
<213> ORGANISM: Artificial Sequence
<220> FEATURE:
<223> OTHER INFORMATION: Variant of hinge region

<400> SEQUENCE: 121

Glu Pro Ser Cys
1

<210> SEQ ID NO 122
<211> LENGTH: 3
<212> TYPE: PRT

<213> ORGANISM: Artificial Sequence
<220> FEATURE:
<223> OTHER INFORMATION: Variant of hinge region

<400> SEQUENCE: 122

Ser Cys Pro
1

<210> SEQ ID NO 123
<211> LENGTH: 221
<212> TYPE: PRT
<213> ORGANISM: homo sapiens

<400> SEQUENCE: 123

```
Pro Ser Cys Pro Ala Pro Glu Phe Leu Gly Gly Pro Ser Val Phe Leu
1               5                   10                  15

Phe Pro Pro Lys Pro Lys Asp Thr Leu Met Ile Ser Arg Thr Pro Glu
            20                  25                  30

Val Thr Cys Val Val Val Asp Val Ser Gln Glu Asp Pro Glu Val Gln
        35                  40                  45

Phe Asn Trp Tyr Val Asp Gly Val Glu Val His Asn Ala Lys Thr Lys
    50                  55                  60

Pro Arg Glu Glu Gln Phe Asn Ser Thr Tyr Arg Val Val Ser Val Leu
65                  70                  75                  80

Thr Val Leu His Gln Asp Trp Leu Asn Gly Lys Glu Tyr Lys Cys Lys
                85                  90                  95

Val Ser Asn Lys Gly Leu Pro Ser Ser Ile Glu Lys Thr Ile Ser Lys
            100                 105                 110

Ala Lys Gly Gln Pro Arg Glu Pro Gln Val Tyr Thr Leu Pro Pro Ser
        115                 120                 125

Gln Glu Glu Met Thr Lys Asn Gln Val Ser Leu Thr Cys Leu Val Lys
    130                 135                 140

Gly Phe Tyr Pro Ser Asp Ile Ala Val Glu Trp Glu Ser Asn Gly Gln
145                 150                 155                 160

Pro Glu Asn Asn Tyr Lys Thr Thr Pro Pro Val Leu Asp Ser Asp Gly
                165                 170                 175

Ser Phe Phe Leu Tyr Ser Arg Leu Thr Val Asp Lys Ser Arg Trp Gln
            180                 185                 190

Glu Gly Asn Val Phe Ser Cys Ser Val Met His Glu Ala Leu His Asn
        195                 200                 205

His Tyr Thr Gln Lys Ser Leu Ser Leu Ser Leu Gly Lys
    210                 215                 220
```

<210> SEQ ID NO 124
<211> LENGTH: 442
<212> TYPE: PRT
<213> ORGANISM: Homo sapiens
<220> FEATURE:
<221> NAME/KEY: MISC_FEATURE
<222> LOCATION: (1)..(442)
<223> OTHER INFORMATION: Amino acids at position 1 to 442 form Human Immunoglobulin G4 Fc Fragment (homodimer)
<220> FEATURE:
<221> NAME/KEY: MISC_FEATURE
<222> LOCATION: (1)..(221)
<223> OTHER INFORMATION: Amino acids at position 1 to 221 form one monomer
<220> FEATURE:
<221> NAME/KEY: MISC_FEATURE
<222> LOCATION: (222)..(442)
<223> OTHER INFORMATION: Amino acids at position 222 to 442 form one monomer
<220> FEATURE:
<221> NAME/KEY: DISULFID
<222> LOCATION: (3)..(224)
<223> OTHER INFORMATION: Amino acids at position 3 and position 224 form an inter-disulfide bond
<220> FEATURE:
<221> NAME/KEY: DISULFID
<222> LOCATION: (35)..(95)
<223> OTHER INFORMATION: Amino acids at position 35 and position 95 form an intra-chain disulfide bond
<220> FEATURE:
<221> NAME/KEY: DISULFID
<222> LOCATION: (141)..(199)
<223> OTHER INFORMATION: Amino acids at position 141 and position 199 form an intra-chain disulfide bond
<220> FEATURE:
<221> NAME/KEY: DISULFID
<222> LOCATION: (256)..(316)
<223> OTHER INFORMATION: Amino acids at position 256 and position 316 form an intra-chain disulfide bond
<220> FEATURE:
<221> NAME/KEY: DISULFID
<222> LOCATION: (362)..(420)
<223> OTHER INFORMATION: Amino acids at position 362 and position 420 form an intra-chain disulfide bond

<400> SEQUENCE: 124

```
Pro Ser Cys Pro Ala Pro Glu Phe Leu Gly Gly Pro Ser Val Phe Leu
1               5                   10                  15

Phe Pro Pro Lys Pro Lys Asp Thr Leu Met Ile Ser Arg Thr Pro Glu
            20                  25                  30

Val Thr Cys Val Val Val Asp Val Ser Gln Glu Asp Pro Glu Val Gln
        35                  40                  45

Phe Asn Trp Tyr Val Asp Gly Val Glu Val His Asn Ala Lys Thr Lys
    50                  55                  60

Pro Arg Glu Glu Gln Phe Asn Ser Thr Tyr Arg Val Val Ser Val Leu
65                  70                  75                  80

Thr Val Leu His Gln Asp Trp Leu Asn Gly Lys Glu Tyr Lys Cys Lys
                85                  90                  95

Val Ser Asn Lys Gly Leu Pro Ser Ser Ile Glu Lys Thr Ile Ser Lys
            100                 105                 110

Ala Lys Gly Gln Pro Arg Glu Pro Gln Val Tyr Thr Leu Pro Pro Ser
        115                 120                 125

Gln Glu Glu Met Thr Lys Asn Gln Val Ser Leu Thr Cys Leu Val Lys
    130                 135                 140

Gly Phe Tyr Pro Ser Asp Ile Ala Val Glu Trp Glu Ser Asn Gly Gln
145                 150                 155                 160

Pro Glu Asn Asn Tyr Lys Thr Thr Pro Pro Val Leu Asp Ser Asp Gly
                165                 170                 175

Ser Phe Phe Leu Tyr Ser Arg Leu Thr Val Asp Lys Ser Arg Trp Gln
            180                 185                 190

Glu Gly Asn Val Phe Ser Cys Ser Val Met His Glu Ala Leu His Asn
        195                 200                 205

His Tyr Thr Gln Lys Ser Leu Ser Leu Ser Leu Gly Lys Pro Ser Cys
    210                 215                 220

Pro Ala Pro Glu Phe Leu Gly Gly Pro Ser Val Phe Leu Phe Pro Pro
225                 230                 235                 240

Lys Pro Lys Asp Thr Leu Met Ile Ser Arg Thr Pro Glu Val Thr Cys
                245                 250                 255

Val Val Val Asp Val Ser Gln Glu Asp Pro Glu Val Gln Phe Asn Trp
            260                 265                 270
```

-continued

```
Tyr Val Asp Gly Val Glu Val His Asn Ala Lys Thr Lys Pro Arg Glu
        275                 280                 285

Glu Gln Phe Asn Ser Thr Tyr Arg Val Val Ser Val Leu Thr Val Leu
    290                 295                 300

His Gln Asp Trp Leu Asn Gly Lys Glu Tyr Lys Cys Lys Val Ser Asn
305                 310                 315                 320

Lys Gly Leu Pro Ser Ser Ile Glu Lys Thr Ile Ser Lys Ala Lys Gly
                325                 330                 335

Gln Pro Arg Glu Pro Gln Val Tyr Thr Leu Pro Pro Ser Gln Glu Glu
            340                 345                 350

Met Thr Lys Asn Gln Val Ser Leu Thr Cys Leu Val Lys Gly Phe Tyr
        355                 360                 365

Pro Ser Asp Ile Ala Val Glu Trp Glu Ser Asn Gly Gln Pro Glu Asn
    370                 375                 380

Asn Tyr Lys Thr Thr Pro Pro Val Leu Asp Ser Asp Gly Ser Phe Phe
385                 390                 395                 400

Leu Tyr Ser Arg Leu Thr Val Asp Lys Ser Arg Trp Gln Glu Gly Asn
                405                 410                 415

Val Phe Ser Cys Ser Val Met His Glu Ala Leu His Asn His Tyr Thr
            420                 425                 430

Gln Lys Ser Leu Ser Leu Ser Leu Gly Lys
        435                 440
```